(12) United States Patent
Oh et al.

(10) Patent No.: US 12,186,379 B2
(45) Date of Patent: Jan. 7, 2025

(54) DENDRITIC CELL ASGPR TARGETING IMMUNOTHERAPEUTICS FOR MULTIPLE SCLEROSIS

(71) Applicant: BAYLOR RESEARCH INSTITUTE, Dallas, TX (US)

(72) Inventors: Sangkon Oh, Baltimore, MD (US); Gerard Zurawski, Midlothian, TX (US)

( * ) Notice: Subject to any disclaimer, the term of this patent is extended or adjusted under 35 U.S.C. 154(b) by 273 days.

(21) Appl. No.: 17/447,607

(22) Filed: Sep. 14, 2021

(65) Prior Publication Data

US 2022/0054609 A1 Feb. 24, 2022

Related U.S. Application Data

(63) Continuation of application No. 14/901,617, filed as application No. PCT/US2014/044711 on Jun. 27, 2014, now abandoned.

(60) Provisional application No. 61/841,094, filed on Jun. 28, 2013.

(51) Int. Cl.
| | | |
|---|---|---|
| A61K 39/00 | (2006.01) | |
| A61P 25/00 | (2006.01) | |
| A61P 25/28 | (2006.01) | |
| A61P 37/02 | (2006.01) | |
| C07K 14/46 | (2006.01) | |
| C07K 16/28 | (2006.01) | |

(52) U.S. Cl.
CPC .......... *A61K 39/0008* (2013.01); *A61P 25/28* (2018.01); *A61P 37/02* (2018.01); *C07K 14/46* (2013.01); *C07K 16/28* (2013.01); *A61K 2039/505* (2013.01); *A61K 2039/577* (2013.01); *A61P 25/00* (2018.01); *C07K 2319/33* (2013.01)

(58) Field of Classification Search
CPC .......... A61K 39/0008; A61K 2039/505; A61K 2039/577; A61P 25/28; A61P 37/02; A61P 25/00; C07K 14/46; C07K 16/28; C07K 2319/33
See application file for complete search history.

(56) References Cited

U.S. PATENT DOCUMENTS

| | | |
|---|---|---|
| 2002/0161218 A1 | 10/2002 | Pachuk et al. |
| 2003/0105303 A1 | 6/2003 | Adema et al. |
| 2004/0143858 A1 | 7/2004 | Adema et al. |
| 2005/0059808 A1 | 3/2005 | Adema et al. |
| 2005/0287582 A1 | 12/2005 | Adema et al. |
| 2008/0070854 A1 | 3/2008 | Pachuk et al. |
| 2008/0206262 A1 | 8/2008 | Banchereau et al. |
| 2008/0233140 A1 | 9/2008 | Banchereau et al. |
| 2008/0241170 A1 | 10/2008 | Zurawski et al. |
| 2008/0254044 A1 | 10/2008 | Zurawski |
| 2008/0254047 A1 | 10/2008 | Banchereau et al. |
| 2008/0267984 A1 | 10/2008 | Banchereau et al. |
| 2010/0135994 A1 | 6/2010 | Banchereau et al. |
| 2010/0209907 A1 | 8/2010 | Adema et al. |
| 2010/0239575 A1 | 9/2010 | Banchereau et al. |
| 2010/0291082 A1 | 11/2010 | Zurawski et al. |
| 2010/0297114 A1 | 11/2010 | Zurawski et al. |
| 2010/0322929 A1 | 12/2010 | Zurawski et al. |
| 2010/0330115 A1 | 12/2010 | Zurawski et al. |
| 2011/0081343 A1 | 4/2011 | Banchereau et al. |
| 2011/0274653 A1 | 11/2011 | Banchereau et al. |
| 2012/0004643 A1 | 1/2012 | Zurawski et al. |
| 2012/0035240 A1 | 2/2012 | Pachuk et al. |
| 2012/0039916 A1 | 2/2012 | Zurawski et al. |
| 2012/0076831 A1 | 3/2012 | Miller et al. |
| 2012/0121592 A1 | 5/2012 | Oh et al. |
| 2012/0128710 A1 | 5/2012 | Oh et al. |
| 2012/0213768 A1 | 8/2012 | Oh et al. |
| 2012/0231023 A1 | 9/2012 | Zurawski et al. |
| 2012/0237513 A1 | 9/2012 | Zurawski et al. |
| 2012/0244155 A1 | 9/2012 | Lecine et al. |
| 2012/0282281 A1 | 11/2012 | Banchereau et al. |
| 2014/0194308 A1 | 7/2014 | Matsuda et al. |

FOREIGN PATENT DOCUMENTS

| | | |
|---|---|---|
| WO | WO 2011/044452 | 4/2011 |
| WO | WO 2013/045488 | 4/2013 |
| WO | WO 2013/160865 | 10/2013 |

OTHER PUBLICATIONS

Mendel, I., et al. Eur. J. Immunol.;25:1951-1959 (Year: 1995).*
Slavin, A. J., et al. Int. Immunol.; 13(6):825-833 (Year: 2001).*
Apostolopoulos et al., "Targeting Antigens to Dendritic Cell Receptors for Vaccine Development," *Journal of Drug Delivery*, 2013; 23(7): 1739-22.
Banchereau et al., "Immunobiology of dendritic cells", *Annu Rev Immunol*, 18: 767-811, 2000.
BD Biosciences: "CD Marker Handbook Human Mouse Welcome to More Choice Human and Mouse CD Marker Handbook," 2010, pp. 1-47. https://www.bdbiosciences.com/documents/ed_marker_handbook_pdf [retrieved Mar. 24, 2015].
Cella et al., "Origin, maturation and antigen presenting function of dendritic cells", *Curr Opin Immunol*, 9(1): 10-6, 1997.
Colman and Filbin, "Myelin Sheath Proteins," *Guidebook to the Extracellular Matrix, Anchor, and Adhesion Protein*, 1999, pp. 244-260.
Fujihara, "Treatment of Neuromyelitis Optica," *Japanese Journal of Clinical Immunology*, 35(2); 129-135, 2012. (English Abstract).
Hellings et al., "T-Cell Reactivity to Multiple Myelin Antigens in Multiple Sclerosis Patients and Healthy Controls," *Journal of Neuroscience Research*, 2001; 63(3): 290-302.
Li et al., "Targeting Self- and Foreign Antigens to Dendritic Cells via DC-ASGPR Generates IL-10-Producing Suppressive CD4+ T Cells," *Journal of Experimental Medicine*, 2012; 209(1): 109-121.

(Continued)

*Primary Examiner* — Brad Duffy
*Assistant Examiner* — Carol Ann Chase
(74) *Attorney, Agent, or Firm* — Norton Rose Fulbright US LLP; Laurie Stellman

(57) ABSTRACT

Methods and compositions for treating multiple sclerosis using dendritic cell anti-ASGPR antibodies fused to myelin basic protein or myelin oligodendrocyte glycoprotein are provided.

19 Claims, 12 Drawing Sheets

Specification includes a Sequence Listing.

(56) References Cited

OTHER PUBLICATIONS

Lutterotti et al., "Antigen-Specific Tolerance by Autologous Myelin Peptide-Coupled Cells: A Phase 1 Trial in Multiple Sclerosis," *Science Translation Medicine*, 2013; 5(188): 1-11.

Mellman and Steinman, "Dendritic Cells: Specialized and Regulated Antigen Processing Machines", *Cell*, 106: 255-58, 2001.

Petzold, et al., "Targeted Antigen Delivery to DEC-205+ Dendritic Cells for Tolerogenic Vaccination," *The Review of Diabetic Studies*, 9(4); 305-318, Winter 2012.

Zhao et al., "Construction and Characterization of an Anti-Asialoglycoprotein Receptor Single-Chain Variable-Fragment-Targeted Melittin," *Biotechnology and Applied Biochemistry*, 2011; 58(6): 405-411.

\* cited by examiner

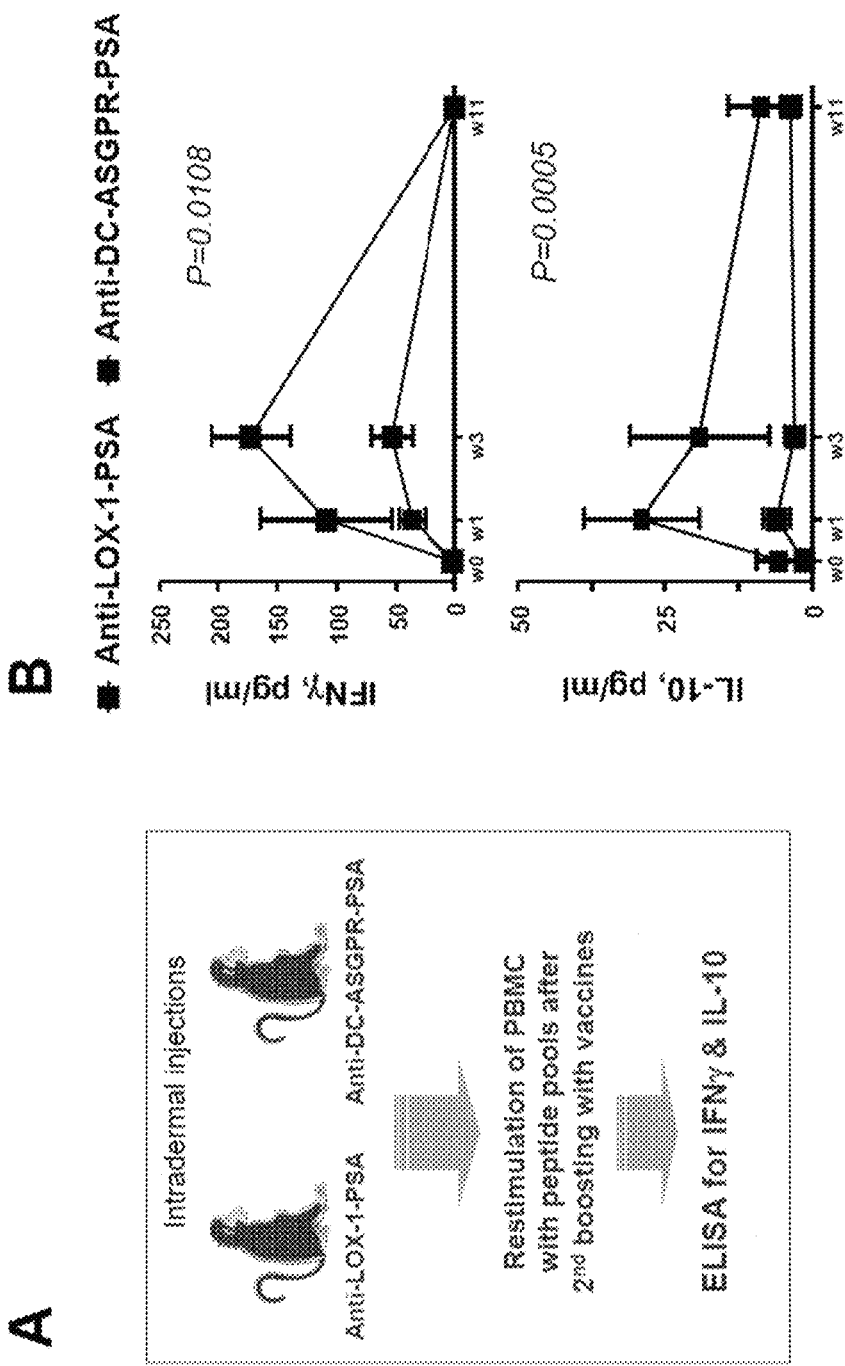
FIG. 1A-B

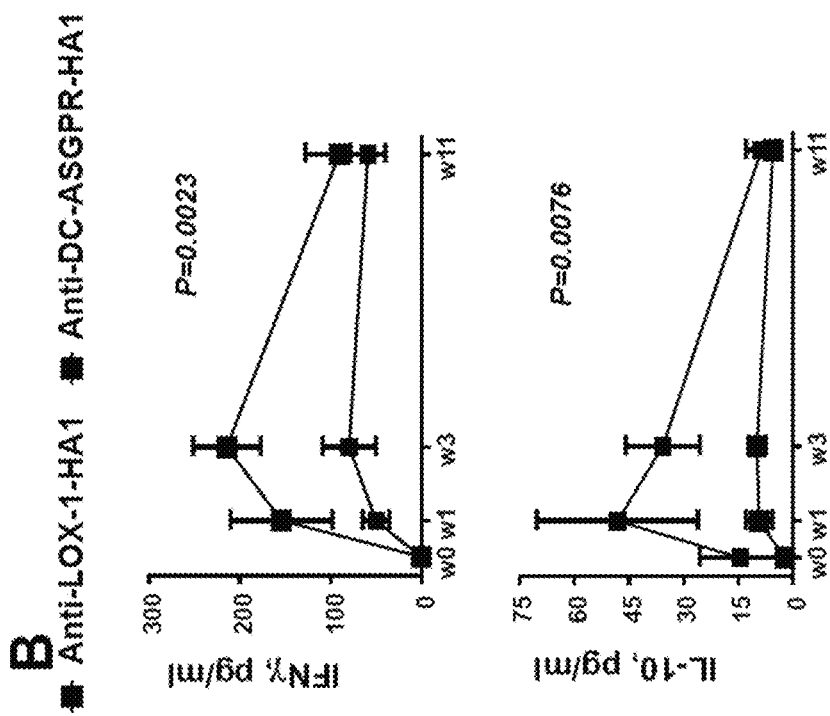
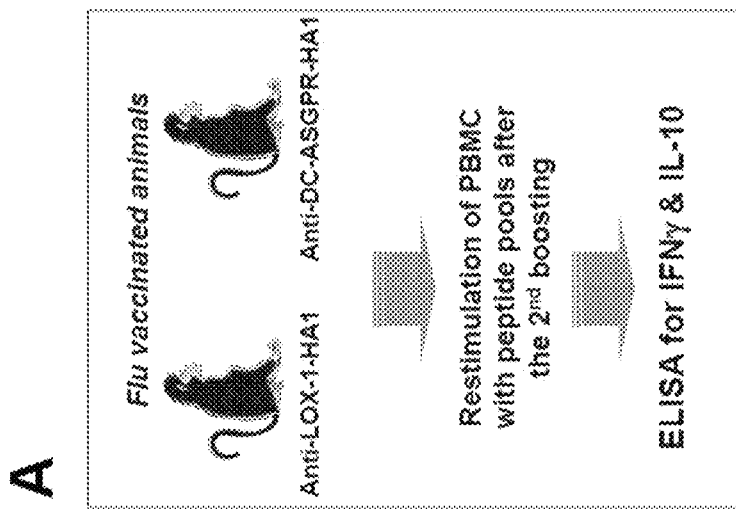
FIG. 2A-B

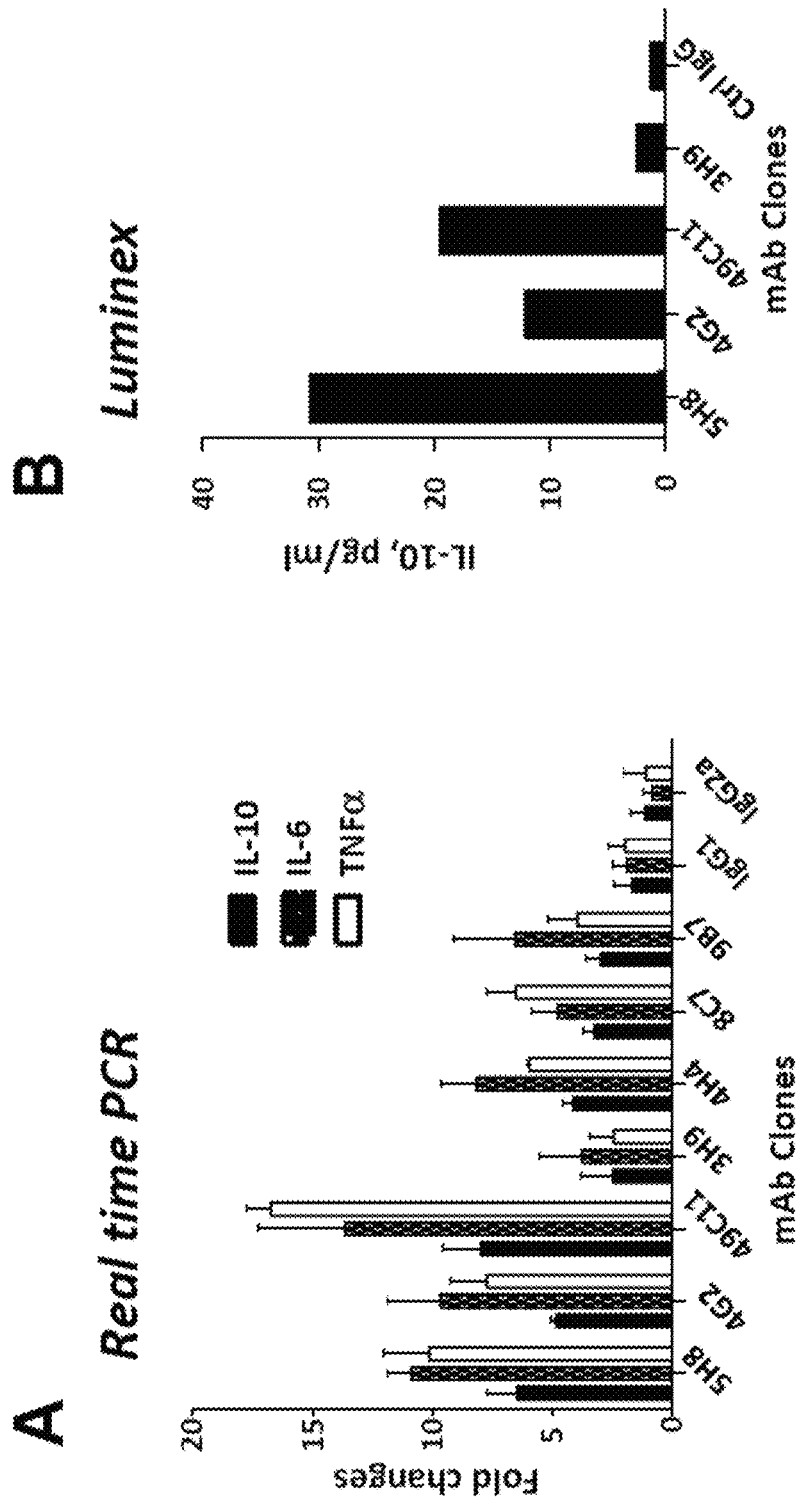
FIG. 3A-B

DENDRITIC CELL ASGPR TARGETING IMMUNOTHERAPEUTICS FOR MULTIPLE SCLEROSIS

This application is a continuation of U.S. patent application Ser. No. 14/901,617, filed Dec. 28, 2015, which is a national phase application under 35 U.S.C. § 371 of International Application No. PCT/US2014/044711, filed Jun. 27, 2014, which claims the benefit of priority to U.S. Provisional Patent Application Ser. No. 61/841,094, filed Jun. 28, 2013, the entire contents of each of which are hereby incorporated by reference in their entirety.

The instant application contains a Sequence Listing which has been submitted in ASCII format and is hereby incorporated by reference in its entirety. Said ASCII copy, created on Sep. 14, 2021, is named BHCSP0380USC1.txt and is 123.337 bytes in size.

BACKGROUND OF THE INVENTION

1. Field of the Invention

The present invention relates generally to the field of medicine. More particularly, it concerns methods and compositions for treating multiple sclerosis using dendritic cell anti-ASGPR antibodies fused to myelin basic protein or myelin oligodendrocyte glycoprotein.

2. Description of Related Art

The inappropriate immune response of the body against substances and tissues normally present in the body is thought to give rise to autoimmune diseases (autoimmunity). Autoimmunity may be restricted to certain organs or involve a particular tissue in different places. While the treatment of autoimmune diseases is typically with immunosuppression—medication that decreases the immune response, the repertoire of these drugs can be limited and in some instances is insufficient to treat the underlying condition. As a large number of autoimmune diseases are recognized, treatment of these represents a substantial human health issue. Multiple sclerosis (MS), also known as disseminated sclerosis or encephalomyelitis disseminata, is an inflammatory disease in which myelin sheaths around axons of the brain and spinal cord are damaged, leading to loss of myelin and scarring. In some instances, the underlying mechanism is thought to be either destruction by the immune system. These changes affect the ability of nerve cells to communicate resulting in a wide range of signs and symptoms.

SUMMARY OF THE INVENTION

Methods and compositions are provided that can be used to induce immune tolerance in autoimmune diseases or conditions. Specifically contemplated are immunotherapeutic compositions and methods of administering these compositions to patients. Embodiments are focused on compositions that target myelin sheath proteins or components to dendritic cells (DC) through receptor mediated endocytosis by targeting specific DC receptors with specific antibodies.

In some embodiments, a method of inducing immune tolerance to at least one myelin sheath protein in a patient is provided. In certain embodiments, the method comprises administering to the patient an effective amount of a composition comprising a dendritic cell targeting complex comprising a dendritic cell antibody, or targeting fragment thereof, attached to the at least one myelin sheath protein, or antigenic fragment thereof. In other embodiments, the myelin sheath protein is myelin basic protein (MBP), myelin oligodendrocyte glycoprotein (MOG), proteolipid protein (PLP), or myelin associated glycoprotein (MAG). In certain aspects the composition comprising a dendritic cell targeting complex comprising a dendritic cell antibody, or targeting fragment thereof, attached to the at least one myelin sheath protein, or antigenic fragment thereof is considered an immunotherapeutic.

In some embodiments, the immunotherapeutic comprises multiple myelin sheath proteins or myelin sheath components. In certain embodiments at least one myelin sheath protein of the immunotherapeutic is MBP. In other embodiments at least one myelin sheath protein of the immunotherapeutic is MOG.

In certain embodiments the dendritic cell antibody or fragment thereof of the dendritic cell targeting complex specifically binds asialoglycoprotein receptor (ASGPR). In yet other embodiments, dendritic cell targeting complex composition comprises multiple dendritic cell targeting complexes. In other aspects the multiple dendritic cell targeting complexes comprise different myelin sheath proteins or different antigenic fragments of one or more myelin sheath proteins. In still other aspects the myelin sheath protein or antigen fragment is separately attached to a dendritic cell antibody, or a targeting fragment thereof. In certain aspects dendritic cell antibody is attached to the myelin sheath protein using a peptide linker. There are different ways in which the antibody or antigenic fragment is attached to the myelin sheath protein. In some embodiments, they are attached directly. In certain embodiments, the antibody or antigenic fragment is attached to the myelin sheath protein through one or more covalent bonds. It is specifically contemplated that there may be a single polypeptide that includes the antibody or antigenic fragment and one or more myelin sheath proteins (or fragments thereof). Such a polypeptide may be described as a fusion protein if the two parts are attached covalently through peptide bonds (with or without a peptide linker). Such a fusion protein with an ASGPR antibody (or antibody fragment) and a myelin sheath protein (or fragment thereof) would not be naturally occurring.

Certain embodiments include an immunogenic composition comprising an isolated polypeptide comprising at least or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 or more amino acids of SEQ ID NO: 42-53, including all values and ranges there between. In a further aspect the isolated polypeptide is a fusion protein. The composition can comprise an adjuvant. In certain aspects the isolated polypeptide is a fusion protein and/or a lipopeptide.

Embodiments include compositions that include a polypeptide, peptide, or protein that is or is at least 70%, 75%, 80%, 85%, 90%, 95%, 96%, 97%, 98%, or 99% identical or similar to any of SEQ ID NO: 42-53. Similar polypeptides, peptides and proteins, in some embodiments, are limited to those proteinaceous compounds whose substitutions are only with conservative amino acids. In other embodiments, only conservative substitutions are contemplated, while in others, deletions of nonessential amino acids or the addition of other amino acids in an area that is not involved in the compound's function are contemplated. In a further embodiment, a composition may include a polypeptide, peptide, or protein that is or is at least 70%, 75%, 80%, 85%, 90%, 95%, 96%, 97%, 98%, or 99% identical or similar to a ASGPR binding polypeptide, such as mAnti-ASGPR_49C11-7H (heavy chain) SEQ ID NO:42, mAnti-ASGPR_49C11-7K (light chain) SEQ ID NO:43, manti-hASGPR_6.3H9.1D11H (heavy chain) SEQ ID NO: 44, manti-hASGPR_6.3H9.1D11K (light chain) SEQ ID NO: 45, manti-hASGPR_5H8.1D4H (heavy chain) SEQ ID NO: 46, manti-hASGPR_5H8.1D4K (light chain) SEQ ID NO: 47, mAnti-ASGPR_4 G2.2_(heavy chain) SEQ ID NO: 48, mAnti-ASGPR_4 G2.2_(light chain) SEQ ID NO: 49, mAnti-ASGPR-5F10H(heavy chain) SEQ ID NO: 50, mAnti-ASGPR-5F10H(light chain) SEQ ID NO: 51, mAnti-ASGPR1H11 (heavy chain) SEQ ID NO: 52, or mAnti-ASGPR1H11(light chain) SEQ ID NO: 53.

The ASGPR binding polypeptides described herein may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more variant amino acids within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of any of SEQ ID NO: 42-53.

In particular embodiments, the immunotherapeutic, DC targeting complex or ASGPR binding polypeptide is purified, which may be accomplished with or without minimal denaturation. In some aspects, the immunotherapeutic, DC targeting complex or ASGPR binding polypeptide is active, meaning the immunotherapeutic, DC targeting complex or ASGPR binding polypeptide retains some detectable level of function or activity, such as those described, including binding ability. It is contemplated that the immunotherapeutic, DC targeting complex or ASGPR binding polypeptide may be purified to about, at least about, or at most about 50, 55, 60, 65, 70, 75, 80, 85, 90, 95, 96, 97, 98, 99, 100% purity or homogeneity (with respect to other proteinaceous molecules and/or cellular macromolecules), or any range derivable therein. In additional embodiments, the recombinant immunotherapeutic, DC targeting complex or ASGPR binding polypeptide may be isolated. The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Furthermore, in certain embodiments of the current methods, methods may involve compositions containing about, at least about, or at most about 0.1, 0.2, 0.3, 0.4, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 21, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µg or mg of protein (or any range derivable therein). The protein may be in about, at least about, or at most about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 10, 11, 12, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µl or ml (or any range derivable therein). In certain aspects, one or more immunotherapeutics, DC targeting complexes or ASGPR binding polypeptides can be administered as a dose of 0.1, 0.2, 0.3, 0.4, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 21, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 mg per kg of body weight.

In particular embodiments, the immune tolerance response elicited by the immunotherapeutic or dendritic cell targeting complex may be complemented, supplemented, increased or augmented. In certain aspects the immune tolerance response elicited by the immunotherapeutic or dendritic cell targeting complex may be complemented, supplemented, increased or augmented by an adjuvant. In certain aspects the adjuvant is a tolerogenic adjuvant. In certain embodiments the immunotherapeutic or dendritic cell targeting complex composition further comprises at least one tolerogenic adjuvant. In certain aspects the tolerogenic adjuvant is attached to the dendritic cell targeting complex. In other aspects, the tolerogenic adjuvant is conjugated to the dendritic cell targeting complex. In still other aspects, the tolerogenic adjuvant is fused to the dendritic cell antibody, or targeting fragment thereof, and/or to the at least one myelin sheath protein. In specific embodiments, the tolerogenic adjuvant is selected from IL-10, dexamethasone, FK506 (Tacrolimus), cholera toxin B subunit, *Escherichia coli* heat-labile enterotoxin B subunit, IFN-beta, glucocorticoids, vitamin D3, and vitamin D3 analogues.

In particular embodiments, the use of binding polypeptides is contemplated to fuse, conjugate or bring together separate polypeptides, portions or modules of the immunotherapeutic or dendritic cell targeting complex. In certain aspects, the dendritic cell antibody or fragment thereof is attached to at least one myelin sheath protein through binding polypeptides. In specific embodiments, the binding polypeptides are dockerin and cohesin.

In certain aspects, administering to the patient an effective amount of a composition comprising a dendritic cell targeting complex comprises more than one administration of the composition. In certain aspects, the composition is administered orally, intravenously, subcutaneously, intradermally, intramuscularly, nasally, by injection, by inhalation, and/or using a nebulizer.

In particular aspects, the methods and compositions described are aimed at treating, preventing, ameliorating, suppressing, resolving, improving or otherwise addressing the symptoms of a subject or patient with an autoimmune disorder, disease or condition. In certain aspects, the subject exhibits one or more symptoms of a demyelinating disease. In other embodiments, the subject has been diagnosed with a demyelinating disease. In still other embodiments, the subject is at risk for a demyelinating disease. In specific embodiments, the demyelinating disease affects the central nervous system. In other specific embodiments, the demyelinating disease is an idiopathic inflammatory demyelinating disease. In certain aspects the demyelinating disease is multiple sclerosis, neuropathy, central pontine myelinolysis, tabes dorsalis, transverse myelitis, Devic's disease, progressive multifocal leukoencephalopathy, optic neuritis, or leukodystrophy. In some embodiments, the demyelinating disease is one of the borderline forms of multiple sclerosis. In some aspects, the borderline form of multiple sclerosis is standard multiple sclerosis, remitent-recidivant multiple sclerosis (RRMS), secondary progressive multiple sclerosis (SPMS), primary progressive multiple sclerosis (PPMS), KIR4.1 multiple sclerosis, optic-spinal multiple sclerosis, opticospinal multiple sclerosis, Devic's disease, acute disseminated encephalomyelitis (ADEM), acute hemorrhagic leukoencephalitis, Balo concentric sclerosis, Schilder disease, diffuse myelinoclastic sclerosis, Marburg multiple sclerosis, malignant multiple sclerosis, fulminant multiple sclerosis, acute multiple sclerosis, tumefactive multiple sclerosis, or solitary sclerosis. In yet other embodiments the demyelinating disease is Susac's syndrome, myalgic encephalomyelitis or leukoaraiosis.

In other specific embodiments, the demyelinating disease is multiple sclerosis. In certain aspects the demyelinating disease affects the peripheral nervous system. In additional embodiments the demyelinating disease is Guillain-Barré syndrome, chronic inflammatory demyelinating polyneuropathy, anti-MAG peripheral neuropathy, Charcot-Marie-Tooth Disease, copper deficiency, or progressive inflammatory neuropathy.

In certain aspects, the methods described comprising a dendritic cell targeting complex and/or immunotherapeutic further comprise preparing the composition. In other embodiments, the methods further comprise measuring antibodies against the at least one myelin sheath protein in the subject after administering the composition.

In some aspects, a method for treating a demyelinating disease in a subject comprising administering to the subject a pharmaceutically acceptable vaccine composition comprising at least a first ASGPR antibody, or binding fragment thereof, attached to myelin basic protein (MBP) and/or myelin oligodendrocyte glycoprotein (MOG), or antigenic fragment thereof is contemplated. In some embodiments, the ASGPR antibody, or binding fragment thereof, is fused to MBP or MOG, or an antigenic fragment thereof. In other embodiments, the subject is administered the vaccine composition multiple times. In still other embodiments, the composition is administered orally, intravenously, subcutaneously, intradermally, intramuscularly, nasally, by injection, by inhalation, and/or using a nebulizer. In certain aspects, the subject exhibits one or more symptoms of a demyelinating disease. In additional aspects, the subject has been diagnosed with a demyelinating disease. In some embodiments, the subject is at risk for a demyelinating disease. In other embodiments, the demyelinating disease affects the central nervous system. In additional embodiments, the demyelinating disease is an idiopathic inflammatory demyelinating disease. In certain aspects, the demyelinating disease is multiple sclerosis, neuropathy, central pontine myelinolysis, tabes dorsalis, transverse myelitis, Devic's disease, progressive multifocal leukoencephalopathy, optic neuritis, or leukodystrophy. In specific embodiments, the demyelinating disease is multiple sclerosis. In some embodiments, the demyelinating disease is one of the borderline forms of multiple sclerosis. In some aspects, the borderline form of multiple sclerosis is standard multiple sclerosis, remitent-recidivant multiple sclerosis (RRMS), secondary progressive multiple sclerosis (SPMS), primary progressive multiple sclerosis (PPMS), KIR4.1 multiple sclerosis, optic-spinal multiple sclerosis, opticospinal multiple sclerosis, Devic's disease, acute disseminated encephalomyelitis (ADEM), acute hemorrhagic leukoencephalitis, Balo concentric sclerosis, Schilder disease, diffuse myelinoclastic sclerosis, Marburg multiple sclerosis, malignant multiple sclerosis, fulminant multiple sclerosis, acute multiple sclerosis, tumefactive multiple sclerosis, or solitary sclerosis. In yet other embodiments the demyelinating disease is Susac's syndrome, myalgic encephalomyelitis or leukoaraiosis. In other aspects, the demyelinating disease affects the peripheral nervous system. In specific embodiments, the demyelinating disease is Guillain-Barré syndrome, chronic inflammatory demyelinating polyneuropathy, anti-MAG peripheral neuropathy, Charcot-Marie-Tooth Disease, copper deficiency, or progressive inflammatory neuropathy. In certain embodiments, the methods further comprise preparing the composition. In further embodiments still, the methods further comprise measuring antibodies against the at least one myelin sheath protein in the subject after administering the composition.

In some embodiments, a composition comprises at least a first ASGPR antibody, or binding fragment thereof, attached to myelin basic protein (MBP) and/or myelin oligodendrocyte glycoprotein (MOG), or antigenic fragment thereof. In other embodiments, the dendritic cell antibody is attached to the myelin sheath protein or antigenic fragment thereof using a peptide linker. In some embodiments, the composition further comprises at least one tolerogenic adjuvant. In still other embodiments, the tolerogenic adjuvant is attached to the dendritic cell targeting complex. In additional embodiments, the tolerogenic adjuvant is conjugated to the dendritic cell targeting complex. In some aspects, the tolerogenic adjuvant is fused to the dendritic cell antibody, or targeting fragment thereof, and/or to the at least one myelin sheath protein. In specific aspects, the tolerogenic adjuvant is selected from IL-10, dexamethasone, FK506 (Tacrolimus), cholera toxin B subunit, *Escherichia coli* heat-labile enterotoxin B subunit, IFN-beta, glucocorticoids, vitamin D3, and vitamin D3 analogues. In still other aspects, the dendritic cell antibody is attached to at least one myelin sheath protein or antigenic fragment thereof through binding polypeptides. In some embodiments, the binding polypeptides are dockerin and cohesin.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the embodiments will become apparent from the following detailed description. It should be understood, however, that the detailed description and the specific examples, while indicating preferred embodiments, are given by way of illustration only, since various changes and modifications within the spirit and scope of the embodiments will become apparent to those skilled in the art from this detailed description.

BRIEF DESCRIPTION OF THE DRAWINGS

The following drawings form part of the present specification and are included to further demonstrate certain aspects of the embodiments. Certain embodiments may be better understood by reference to one or more of these drawings in combination with the detailed description of specific embodiments presented herein.

FIG. 1A-B: (A) Experimental method schematic. (B) Anti-DC-ASGPR-PSA vaccine can prime PSA-specific IL-10-producing CD4+ T cells in NHPs.

FIG. 2A-B: (A) Experimental method schematic. (B) Anti-DC-ASGPR-HA1 promotes IL-10-producing HA1-specific CD4$^+$ T cells in vivo.

FIG. 3A-B: Monoclonal antibody selection. (A) RT-PCR assay. (B) Luminex assay. 3/7 clones induce DCs to express IL-10, other clones induce less than 10 pg/ml IL-10. Levels of IL-10 expression are variable among donors, IL-6 and TNFa are in background levels in Luminex assay.

FIG. 4: Monoclonal antibody selection. 49C11 binds to $CD11c^+$ blood DCs in MS patients and healthy donors.

FIG. 5: Generation of anti-DC-ASGPR-MBP and anti-DC-ASGPR-MOG fusion proteins. Expression product of anti-DC-ASGPR (49C11) mAb fused to MBP and MOG.

FIG. 6A-B: (A) Experimental method schematic. (B) In vitro validation of anti-DC-ASGPR (49C11)-MBP proteins. Anti-DC-ASGPR (49C11)-MBP binds to $CD11c^+$ DCs in PBMCs and promotes MBP-specific Treg responses.

FIG. 7A-B: In vitro validation of anti-DC-ASGPR (49C11)-MOG proteins. (A) CD11c+ DC staining. (B) MS patient PBMC loading assay. Anti-DC-ASGPR-MOG binds to DCs and promotes MOG-specific Treg response.

FIG. 8: Effectiveness of anti-ASGPR-hMOG in EAE Model in Cynomolgus Macaque—Experimental Design.

FIG. 9: Anti-DC-ASGPR-MOG treatment suppresses EAE development progression

FIG. 10: Anti-DC-ASGPR-MOG treatment results in enhanced survival of animals FIG. 11: Magnetic resonance images of AM637 animal brain on day 22.

DESCRIPTION OF ILLUSTRATIVE EMBODIMENTS

I. Multiple Sclerosis Immunotherapeutic Technology

Methods and compositions are provided to generate immune tolerance in a subject against one or more myelin sheath antigens in order to protect against or treat for autoimmune disorders such as multiple sclerosis. Dendritic cells (DCs) are antigen-presenting cells that play a key role in regulating antigen-specific immunity (Mellman and Steinman 2001), (Banchereau, Briere et al. 2000), (Cella, Sallusto et al. 1997). DCs capture antigens, process them into peptides, and present these to T cells. Therefore delivering antigens directly to DC is a focus area for developing immunotherapeutics.

Provided herein are immunotherapeutics compositions containing myelin sheath antigens for delivery to DC in order to generate an immune tolerance response to myelin sheath protein or components or to suppress an immune response to myelin sheath protein or components. In some embodiments the myelin sheath protein or component is myelin basic protein (MBP). In other embodiments the myelin sheath protein or component is myelin oligodendrocyte glycoprotein (MOG). In yet other embodiments, the myelin sheath protein or component is proteolipid protein (PLP). In still other embodiments the myelin sheath protein or component is myelin associated glycoprotein. In additional embodiments, the myelin sheath protein or component is any one of peripheral myelin protein (PMP-22), Po protein, connexin 32 protein, Schwann cell myelin protein, or oligodendrocyte-myelin glycoprotein (OMgp). In still additional embodiments, the immunotherapeutic comprises multiple different myelin sheath components as stated above.

The type of immune response that is generated after delivery of an immunotherapeutic may be modulated by the type of receptor that is targeted by said therapeutic. In some embodiments of the present methods, asialoglycoprotein receptor (ASGPR) is targeted by ASGPR binding antibodies. In some aspects the antibodies are monoclonal antibodies. In yet other aspects, the antibodies are mouse monoclonal antibodies. In still other aspects, the antibodies are human/mouse chimeras. In further aspects, the antibodies are humanized monoclonal antibodies.

Figure 4:
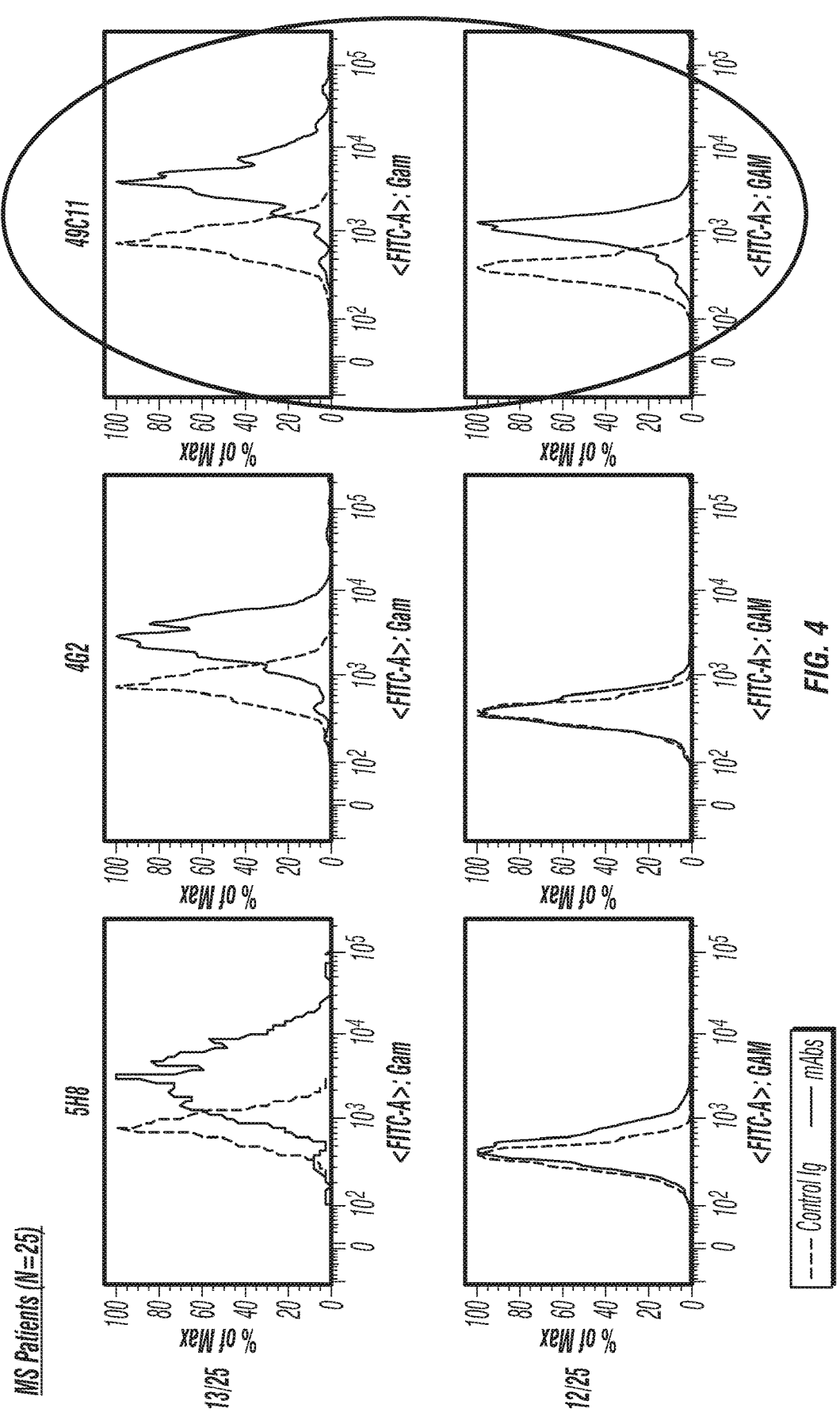
Figure 4:
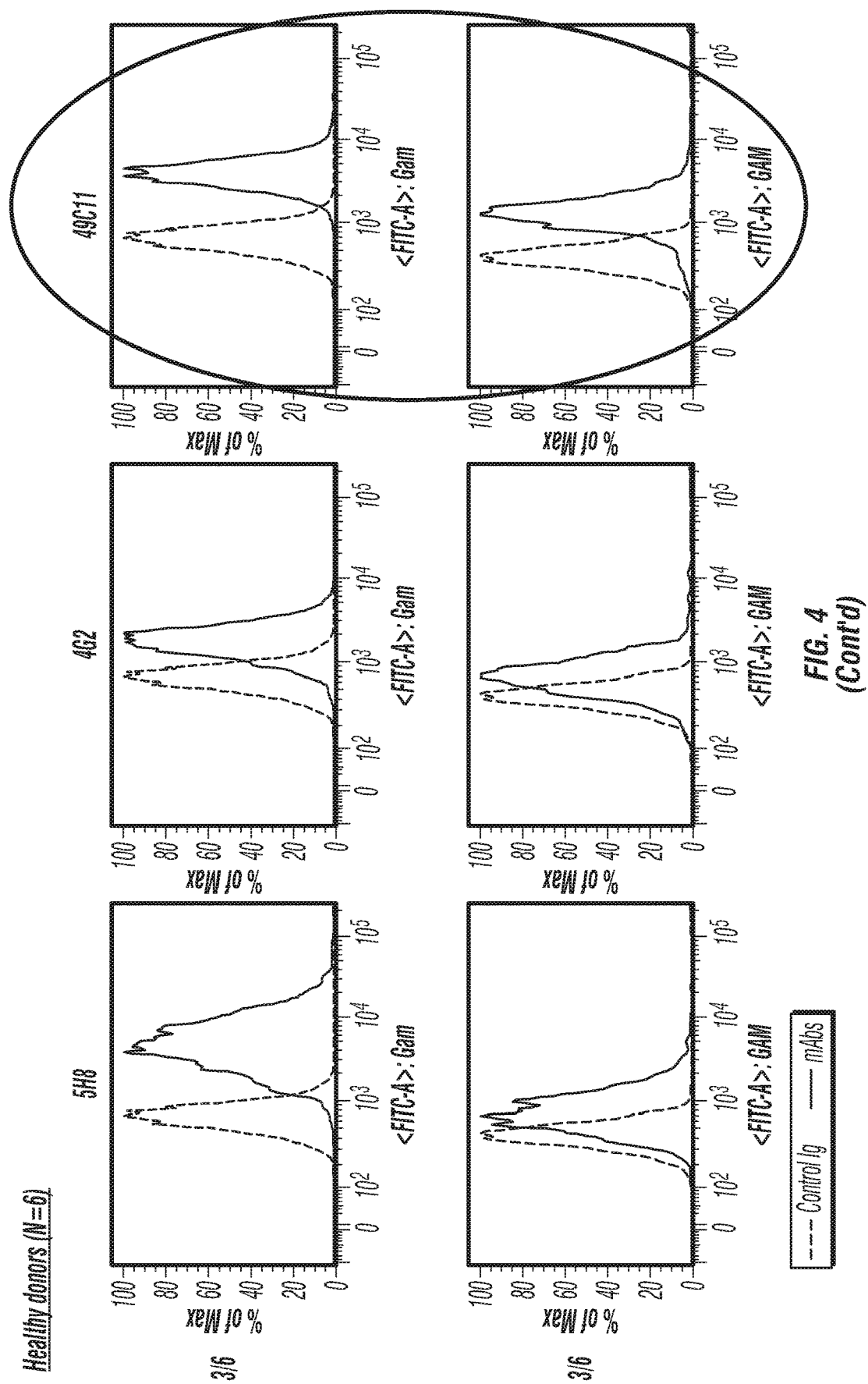
Figure 5:
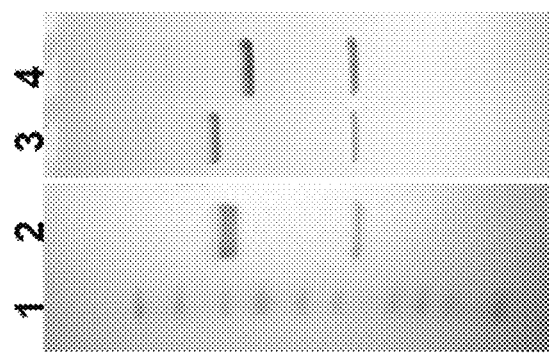

In certain aspects, the type of receptor that is targeted by the immunotherapeutic is DEC-205. DEC-205 is a type I cell surface protein expressed primarily by dendritic cells (DC). In some embodiments of the present methods, DEC-205 is targeted by DEC-205 binding antibodies. In some aspects the antibodies are DEC-205 monoclonal antibodies. In yet other aspects, the antibodies are DEC-205 mouse monoclonal antibodies. In still other aspects, the antibodies are DEC-205 mouse/human chimeras. In further aspects, the antibodies are humanized DEC-205 mouse monoclonal antibodies.

Such technology and embodiments are described in the following U.S. Patent Publications 20120282281 (Agents that Engage Antigen-Presenting Cells Through Dendritic Cell Asialoglycoprotein Receptor (DC-ASGPR)); 20120244155 (Dendritic Cells (DCs) Targeting for Tuberculosis (TB) Vaccine); 20120237513 (Vaccines Based on Targeting Antigen to DCIR Expressed on Antigen-Presenting Cells); 20120231023 (Novel Vaccine Adjuvants Based on Targeting Adjuvants to Antibodies Directly to Antigen-Presenting Cells); 20120213768 (Diagnostic and Therapeutic Uses for B Cell Maturation Antigen); 20120128710 (Enhancement of Pathogen-Specific Memory Th17 Cell Responses); 20120121592 (Targeting Antigens to Human Dendritic Cells Via DC-Asialoglycoprotein Receptor to Produce IL-10 Regulatory T-Cells; 20120039916 (NOVEL VACCINE ADJUVANTS BASED ON TARGETING ADJUVANTS TO ANTIBODIES DIRECTLY TO ANTIGEN-PRESENTING CELLS); 20120035240 (CONSERVED HBV AND HCV SEQUENCES USEFUL FOR GENE SILENCING); 20120020990 (ISOLATED MAMMALIAN MONOCYTE CELL GENES; RELATED REAGENTS); 20120004643 (Vaccines Based on Targeting Antigen to DCIR Expressed on Antigen-Presenting Cells); 20110274653 (DENDRITIC CELL IMMUNORECEPTORS (DCIR)-MEDIATED CROSSPRIMING OF HUMAN CD8+T CELLS); 20110081343 (VACCINES DIRECTED TO LANGERHANS CELLS); 20100330115 (Multivariable Antigens Complexed with Targeting Humanized Monoclonal Antibody); 20100322929 (ANTIGEN PRESENTING CELL TARGETED CANCER VACCINES); 20100297114 (ANTIGEN PRESENTING CELL TARGETED VACCINES); 20100291082 (ANTIGEN PRESENTING CELL TARGETED ANTI-VIRAL VACCINES); 20100239575 (ANTI-CD40 ANTIBODIES AND USES THEREOF); 20100209907 (ISOLATED MAMMALIAN MONOCYTE CELL GENES; RELATED REAGENTS); 20100135994 (HIV VACCINE BASED ON TARGETING MAXIMIZED GAG AND NEF TO DENDRITIC CELLS); 20080267984 (Activation of Human Antigen-Presenting Cells Through Dendritic Cell Lectin-Like Oxidized LDL Receptor-1 (LOX-1)); 20080254047 (Activation of Human Antigen-Presenting Cells Through CLEC-6); 20080254044 (Multivariable Antigens Complexed with Targeting Humanized Monoclonal Antibody); 20080241170 (Vaccines Based on Targeting Antigen to DCIR Expressed on Antigen-Presenting Cells); 20080233140 (Therapeutic Applications of Activation of Human Antigen-Presenting Cells Through Dectin-1); 20080206262 (Agents That Engage Antigen-Presenting Cells Through Dendritic Cell Asialoglycoprotein Receptor (DC-ASGPR)); 20080070854 (Conserved Hbv and Hcv Sequences Useful for Gene Silencing); 20050287582 (Antibodies that specifically bind to FDF03); 20050059808 (Isolated mammalian monocyte cell genes; related reagents); 20040143858 (Isolated mammalian monocyte cell genes; related reagents); 20030105303 (Isolated mammalian monocyte cell genes; related reagents); and, 20020161218 (Hepatitis C virus vaccine), all of which are hereby incorporated by reference.

II. Nucleic Acids

In certain embodiments, there are recombinant nucleic acids encoding the proteins, polypeptides, or peptides described herein. Polynucleotides contemplated for use in methods and compositions include those encoding antibodies against DC receptors (also referred to as anti-DC antibodies and DC targeting antibodies) or binding portions thereof.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or fewer in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein (see above).

In particular embodiments, there are isolated nucleic acid segments and recombinant vectors incorporating nucleic acid sequences that encode a polypeptide (e.g., an antibody or fragment thereof) that binds to DC receptors. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide will comprise a nucleotide sequence encoding a polypeptide that has at least 90%, preferably 95% and above, identity to an amino acid sequence described herein, over the entire length of the sequence; or a nucleotide sequence complementary to said isolated polynucleotide.

Vectors

Polypeptides may be encoded by a nucleic acid molecule. The nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Vectors may be used in a host cell to produce an antibody that binds a dendritic cell receptor.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with an embodiment to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems, other examples of expression systems include STRATAGENE®'s COMPLETE CONTROL Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

III. Proteinaceous Compositions

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that bacteria containing such a variant may be implemented in compositions and methods. Consequently, a protein need not be isolated.

The term "functionally equivalent codon" is used herein to refer to codons that encode the same amino acid, such as the six codons for arginine or serine, and also refers to codons that encode biologically equivalent amino acids (see Table, below).

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be an antibody that targets DC, and may be used in combination with other proteins, antibodies or protein-binding antibodies described herein.

Polypeptides and Polypeptide Production

Embodiments involve polypeptides, peptides, and proteins and immunogenic fragments thereof for use in various aspects described herein. For example, specific antibodies are assayed for or used in binding to DC receptors and presenting myelin sheath protein or components as antigens.

In specific embodiments, all or part of proteins described herein can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One embodiment includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are discussed herein. Alternatively, the protein to be produced may be an endogenous protein normally synthesized by the cell used for protein production.

In a certain aspects a DC receptor fragment comprises substantially all of the extracellular domain of a protein which has at least 85% identity, at least 90% identity, at least 95% identity, or at least 97-99% identity, including all values and ranges there between, to a sequence selected over the length of the fragment sequence.

Also included in immunogenic compositions are fusion proteins composed of myelin sheath protein or components, or immunogenic fragments of myelin sheath protein or components (e.g., myelin basic protein, proteolipid protein, myelin-associated glycoprotein, myelin oligodendrocyte glycoprotein, peripheral myelin protein (PMP-22), Po protein, connexin 32 protein, Schwann cell myelin protein, oligodendrocyte-myelin glycoprotein (OMgp)). Alternatively, embodiments also include individual fusion proteins of myelin sheath protein or components or immunogenic fragments thereof, as a fusion protein with heterologous sequences such as a provider of T-cell epitopes or purification tags, for example: β-galactosidase, glutathione-S-transferase, 6×His, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, CRM197.

Antibodies and Antibody-Like Molecules

In certain aspects, one or more antibodies or antibody-like molecules (e.g., polypeptides comprising antibody CDR domains) may be obtained or produced which have a specificity for a DC receptor. These antibodies may be used in various diagnostic or therapeutic applications described herein.

As used herein, the term "antibody" is intended to refer broadly to any immunologic binding agent such as IgG, IgM, IgA, IgD and IgE as well as polypeptides comprising antibody CDR domains that retain antigen binding activity. Thus, the term "antibody" is used to refer to any antibody-like molecule that has an antigen binding region, and includes antibody fragments such as Fab', Fab, F(ab')2, single domain antibodies (DABs), Fv, scFv (single chain Fv), and polypeptides with antibody CDRs, scaffolding domains that display the CDRs (e.g., anticalins) or a nanobody. For example, the nanobody can be antigen-specific VHH (e.g., a recombinant VHH from a camelid IgG2 or IgG3, or a CDR-displaying frame from such camelid Ig.

Production and use of camelid antibodies is described in EP1118669 A9 and EP1414858 B1, both of which are incorporated herein by reference. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with embodiments. Minibodies are sFv polypeptide chains which include oligomerization domains at their C-termini, separated from the sFv by a hinge region (Pack et al., 1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Alternative scaffolds for antigen binding peptides, such as CDRs are also available and can be used to generate DC receptor-binding molecules in accordance with the embodiments. Generally, a person skilled in the art knows how to determine the type of protein scaffold on which to graft at least one of the CDRs arising from the original antibody. More particularly, it is known that to be selected such scaffolds must meet the greatest number of criteria as follows (Skerra, 2000): good phylogenetic conservation; known three-dimensional structure (as, for example, by crystallography, NMR spectroscopy or any other technique known to a person skilled in the art); small size; few or no post-transcriptional modifications; and/or easy to produce, express and purify.

The origin of such protein scaffolds can be, but is not limited to, the structures selected among: fibronectin and preferentially fibronectin type III domain 10, lipocalin, anticalin (Skerra, 2001), thioredoxin A or proteins with a repeated motif such as the "ankyrin repeat" (Kohl et al., 2003), the "armadillo repeat", the "leucine-rich repeat" and the "tetratricopeptide repeat". For example, anticalins or lipocalin derivatives are a type of binding proteins that have affinities and specificities for various target molecules; such proteins are described in US Patent Publication Nos. 20100285564, 20060058510, 20060088908, 20050106660, and PCT Publication No. WO2006/056464, incorporated herein by reference.

Scaffolds derived from toxins such as, for example, toxins from scorpions, insects, plants, mollusks, etc., and the protein inhibiters of neuronal NO synthase (PIN) may also be used in certain aspects.

Monoclonal antibodies (MAbs) are recognized to have certain advantages, e.g., reproducibility and large-scale production. Embodiments include monoclonal antibodies of the human, murine, monkey, rat, hamster, rabbit and chicken origin.

"Humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin. In order to describe antibodies of some embodiments, the strength with which an antibody molecule binds an epitope, known as affinity, can be measured. The affinity of an antibody may be determined by measuring an association constant (Ka) or dissociation constant (Kd). Antibodies deemed useful in certain embodiments may have an association constant of about, at least about, or at most about 10e6, 10e7, 10e8, 10e9 or 10e10 M or any range derivable therein. Similarly, in some embodiments antibodies may have a dissociation constant of about, at least about or at most about 10e-6, 10e-7, 10e-8, 10e-9 or 10e-10. M or any range derivable therein. These values are reported for antibodies discussed herein and the same assay may be used to evaluate the binding properties of such antibodies.

In certain embodiments, the antibodies are recombinant antibodies. A recombinant antibody differs from an endogenously-produced antibody. For example, recombinant antibodies differ with respect to their glycosylation status (see, for example, Jefferis, R. "Glycosylation of Recombinant Antibody Therapeutics" *Biotechnol. Prog.* 2005, 21:11-16 which is herein incorporated by reference).

In certain embodiments, a polypeptide that specifically binds to DC receptors is able to bind a DC receptor on the surface of the cells and present a myelin sheath protein or component that allows the generation of a robust immune tolerance to that myelin sheath protein or component. Moreover, in some embodiments, the polypeptide that is used can provide immune tolerance against a myelin sheath protein or component and protect against multiple sclerosis.

1. Methods for Generating Antibodies

Methods for generating antibodies (e.g., monoclonal antibodies and/or monoclonal antibodies) are known in the art. Briefly, a polyclonal antibody is prepared by immunizing an animal with a DC receptor polypeptide or a portion thereof in accordance with embodiments and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art. It will be appreciated that antibodies can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

As is also well known in the art, the immunogenicity of a particular immunogen composition can be enhanced by the use of non-specific stimulators of the immune response, known as adjuvants. Suitable adjuvants include any acceptable immunostimulatory compound, such as cytokines, chemokines, cofactors, toxins, plasmodia, synthetic compositions or vectors encoding such adjuvants. Adjuvants may be chemically conjugated to antibodies or antigen-delivering antibody fusions proteins. Alternatively adjuvants may be recombinantly fused to antibodies or antigen-delivering antibody fusions proteins. In certain aspects, adjuvants may be chemically conjugated or recombinantly fused to cohesin or dockerin to allow for binding to any other molecule containing a corresponding dockerin or cohesin binding domain.

Adjuvants that may be used in accordance with embodiments include, but are not limited to, IL-1, IL-2, IL-4, IL-7, IL-12, -interferon, GMCSP, BCG, aluminum hydroxide, Poly ICLC, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary adjuvants may include complete Freund's adjuvant (a non-specific stimulator of the immune response containing killed *Mycobacterium tuberculosis*), incomplete Freund's adjuvants and/or aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m2) (Johnson/Mead, NJ), cytokines such as -interferon, IL-2, or IL-12 or genes encoding proteins involved in immune helper functions, such as B-7.

The amount of immunogen composition used in the production of antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography, among others.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. In some embodiments, Rodents such as mice and rats are used in generating monoclonal antibodies. In some embodiments, rabbit, sheep or frog cells are used in generating monoclonal antibodies. The use of rats is well known and may provide certain advantages (Goding, 1986, pp. 60 61). Mice (e.g., BALB/c mice) are routinely used and generally give a high percentage of stable fusions.

The animals are injected with antigen, generally as described above. The antigen may be mixed with adjuvant, such as Freund's complete or incomplete adjuvant. Booster administrations with the same antigen or DNA encoding the antigen may occur at approximately two-week intervals. As discussed in the Examples, the antigen may be altered compared to an antigen sequence found in nature.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Generally, spleen cells are a rich source of antibody-producing cells that are in the dividing plasmablast stage. Typically, peripheral blood cells may be readily obtained, as peripheral blood is easily accessible.

In some embodiments, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody producing B lymphocytes from the immunized animal are then fused with cells of an immortal myeloma cell, generally one of the same species as the animal that was immunized. Myeloma cell lines suited for use in hybridoma producing fusion procedures preferably are non-antibody producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65 66, 1986; Campbell, pp. 75 83, 1984). cites). For example, where the immunized animal is a mouse, one may use P3 X63/Ag8, X63 Ag8.653, NS1/1.Ag 4 1, Sp210 Ag14, FO, NSO/U, MPC 11, MPC11 X45 GTG 1.7 and S194/5XX0 Bu1; for rats, one may use R210.RCY3, Y3 Ag 1.2.3, IR983F and 4B210; and U 266, GM1500 GRG2, LICR LON HMy2 and UC729 6 are all useful in connection with human cell fusions. See Yoo et al. (2002), for a discussion of myeloma expression systems.

One murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8 azaguanine resistant mouse murine myeloma SP2/0 non producer cell line.

Methods for generating hybrids of antibody producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 71 74, 1986).

Fusion procedures usually produce viable hybrids at low frequencies, about $1 \times 10$-6 to $1 \times 10$-8. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

A selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

Further, expression of antibodies (or other moieties therefrom) from production cell lines can be enhanced using a number of known techniques. For example, the glutamine synthetase and DHFR gene expression systems are common approaches for enhancing expression under certain conditions. High expressing cell clones can be identified using conventional techniques, such as limited dilution cloning and microdrop technology. The GS system is discussed in whole or part in connection with European Patent Nos. 0 216 846, 0 256 055, and 0 323 997 and European Patent Application No. 89303964.4.

MAbs produced by either means may be further purified, if desired, using filtration, centrifugation and various chromatographic methods such as HPLC or affinity chromatography. Fragments of the monoclonal antibodies can be obtained from the monoclonal antibodies so produced by methods which include digestion with enzymes, such as pepsin or papain, and/or by cleavage of disulfide bonds by chemical reduction. Alternatively, monoclonal antibody fragments can be synthesized using an automated peptide synthesizer.

It is also contemplated that a molecular cloning approach may be used to generate monoclonal antibodies. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately 10e4 times as many antibodies can be produced and screened in a single round, and that new specificities are generated by H and L chain combination which further increases the chance of finding appropriate antibodies.

Another embodiment concerns producing antibodies, for example, as is found in U.S. Pat. No. 6,091,001, which describes methods to produce a cell expressing an antibody from a genomic sequence of the cell comprising a modified immunoglobulin locus using Cre-mediated site-specific recombination is disclosed. The method involves first transfecting an antibody-producing cell with a homology-targeting vector comprising a lox site and a targeting sequence homologous to a first DNA sequence adjacent to the region of the immunoglobulin loci of the genomic sequence which is to be converted to a modified region, so the first lox site is inserted into the genomic sequence via site-specific homologous recombination. Then the cell is transfected with a lox-targeting vector comprising a second lox site suitable for Cre-mediated recombination with the integrated lox site and a modifying sequence to convert the region of the immunoglobulin loci to the modified region. This conversion is performed by interacting the lox sites with Cre in vivo, so that the modifying sequence inserts into the genomic sequence via Cre-mediated site-specific recombination of the lox sites.

Alternatively, monoclonal antibody fragments can be synthesized using an automated peptide synthesizer, or by expression of full-length gene or of gene fragments in *E. coli*.

It is further contemplated that monoclonal antibodies may be further screened or optimized for properties relating to specificity, avidity, half-life, immunogenicity, binding association, binding disassociation, or overall functional properties relative to being a treatment for infection and/or disease state. Thus, it is contemplated that monoclonal antibodies may have 1, 2, 3, 4, 5, 6, or more alterations in the amino acid sequence of 1, 2, 3, 4, 5, or 6 CDRs of monoclonal antibodies mAnti-ASGPR 49C11, mAnti-ASGPR 4G2.2, mAnti-ASGPR 5F10, mAnti-ASGPR 1H11, mAnti-ASGPR 6.3H9.1D11, mAnti-ASGPR 5H8.1D4. It is contemplated that the amino acid in position 1, 2, 3, 4, 5, 6, 7, 8, 9, or 10 of CDR1, CDR2, CDR3, CDR4, CDR5, or CDR6 of the VJ or VDJ region of the light or heavy variable region of monoclonal antibodies mAnti-ASGPR 49C11, mAnti-ASGPR 4G2.2, mAnti-ASGPR 5F10, mAnti-ASGPR 1H11, mAnti-ASGPR 6.3H9.1D11, mAnti-ASGPR 5H8.1D4, may have an insertion, deletion, or substitution with a conserved or non-conserved amino acid. Such amino acids that can either be substituted or constitute the substitution are disclosed above.

Methods of determining CDRs from the sequence of a variable region are known in the art (see, for example, Zhao and Lu, "A germline knowledge based computational approach for determining antibody complementarity determining regions." Mol. Immunol., (2010) 47(4):694-700, which is herein incorporated by reference).

In some embodiments, fragments of a whole antibody can perform the function of binding antigens. Examples of binding fragments are (i) the Fab fragment constituted with the VL, VH, CL and CH1 domains; (ii) the Fd fragment consisting of the VH and CH1 domains; (iii) the Fv fragment constituted with the VL and VH domains of a single antibody; (iv) the dAb fragment (Ward, 1989; McCafferty et al., 1990; Holt et al., 2003), which is constituted with a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988; Huston et al., 1988); (viii) bispecific single chain Fv dimers (PCT/US92/09965) and (ix) "diabodies", multivalent or multispecific fragments constructed by gene fusion (WO94/13804; Holliger et al., 1993). Fv, scFv or diabody molecules may be stabilized by the incorporation of disulphide bridges linking the VH and VL domains (Reiter et al., 1996). Minibodies comprising a scFv joined to a CH3 domain may also be made (Hu et al. 1996). The citations in this paragraph are all incorporated by reference.

Antibodies also include bispecific antibodies. Bispecific or bifunctional antibodies form a second generation of monoclonal antibodies in which two different variable regions are combined in the same molecule (Holliger, P. & Winter, G. 1999 Cancer and metastasis rev. 18:411-419, 1999). Their use has been demonstrated both in the diagnostic field and in the therapy field from their capacity to recruit new effector functions or to target several molecules on the surface of tumor cells. Where bispecific antibodies are to be used, these may be conventional bispecific antibodies, which can be manufactured in a variety of ways (Holliger et al, PNAS USA 90:6444-6448, 1993), e.g. prepared chemically or from hybrid hybridomas, or may be any of the bispecific antibody fragments mentioned above. These antibodies can be obtained by chemical methods (Glennie et al., 1987 J. Immunol. 139, 2367-2375; Repp et al., J. Hemat. 377-382, 1995) or somatic methods (Staerz U. D. and Bevan M. J. PNAS 83, 1986; et al., Method Enzymol. 121:210-228, 1986) but likewise by genetic engineering techniques which allow the heterodimerization to be forced and thus facilitate the process of purification of the antibody sought (Merchand et al. Nature Biotech, 16:677-681, 1998). Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction. The citations in this paragraph are all incorporated by reference.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against a DC receptor, then a library can be made where the other arm is varied and an antibody of appropriate specificity selected. Bispecific whole antibodies may be made by alternative engineering methods as described in Ridgeway et al, (Protein Eng., 9:616-621, 1996), which is hereby incorporated by reference.

Antibody and Polypeptide Conjugates

Embodiments provide antibodies and antibody-like molecules against DC receptors, polypeptides and peptides that are linked to at least one agent to form an antibody conjugate or payload or fusion. Embodiments also provide antibody drug conjugates (ADC). In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, therapeutic enzymes, antibiotics, radio-labeled nucleotides and the like. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired.

Antibody conjugates are in certain embodiments used as diagnostic agents. Antibody diagnostics generally fall within two classes, those for use in in vitro diagnostics, such as in a variety of immunoassays, and/or those for use in vivo diagnostic protocols, generally known as "antibody directed imaging". Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might use astatine$^{211}$, carbon$^{14}$, chromium$^{51}$, chlorine$^{36}$, cobalt$^{57}$, cobalt$^{58}$, copper$^{67}$, Eu$^{152}$, gallium$^{67}$, hydrogen$^{3}$, iodine$_{123}$, iodine$^{125}$, iodine$^{131}$, indium$^{111}$, iron$^{59}$, phosphorus$^{32}$, rhenium$^{186}$, rhenium$^{188}$, selenium$^{75}$, sulphur$^{35}$, technicium$^{99}$ and/or yttrium$^{90}$. $^{125}$I is often used in certain embodiments, and technicium$^{99}$ and/or indium$^{111}$ are also often used due to their low energy and suitability for long range detection. Radioactively labeled monoclonal antibodies may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies may be labeled with technetium99m by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red, among others.

Antibody conjugates include those intended primarily for use in vitro, where the antibody is linked to a secondary binding ligand and/or to an enzyme (an enzyme tag) that will generate a colored product upon contact with a chromogenic substrate. Examples of suitable enzymes include, but are not limited to, urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277, 437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In some embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

IV. Dendritic Cell Immunotherapeutics

As used herein, "Dendritic Cells" (DCs) refers to any member of a diverse population of morphologically similar cell types found in lymphoid or non-lymphoid tissues. These cells are characterized by their distinctive morphology, high levels of surface MHC-class II expression (Steinman, et al., Ann. Rev. Immunol. 9:271 (1991); incorporated herein by reference for its description of such cells). These cells can be isolated from a number of tissue sources, and conveniently, from peripheral blood, as described herein.

Myelin Sheath Proteins and Components as Antigens

In certain embodiments any myelin sheath protein or component (including but not limited to myelin sheath protein, glycoprotein, lipid or glycolipid) may be recombinantly fused or chemically conjugated to a DC targeting antibody to deliver the myelin sheath protein or component to a dendritic cell. A myelin sheath protein or component may be any myelin sheath protein or component that when fused to a DC targeting antibody is sufficient to evoke an immune tolerance response in a subject. In certain embodiments the immune response is sufficient to protect a subject from multiple sclerosis. In other embodiments protection afforded by the antigen/targeting antibody fusion is sufficient to depress or prevent symptoms associated with multiple sclerosis.

In some embodiments the myelin sheath protein or component is myelin basic protein (MBP). In other embodiments the myelin sheath protein or component is myelin oligodendrocyte glycoprotein (MOG). In yet other embodiments, the myelin sheath protein or component is proteolipid protein (PLP). In still other embodiments the myelin sheath protein or component is myelin associated glycoprotein. In additional embodiments, the myelin sheath protein or component is any one of peripheral myelin protein (PMP-22), Po protein, connexin 32 protein, Schwann cell myelin protein, or oligodendrocyte-myelin glycoprotein (OMgp). In still additional embodiments, the immunotherapeutic comprises multiple different myelin sheath components as stated above.

Dendritic Cell Specific Antibodies

In certain aspects, antibodies used to target myelin sheath protein or components to dendritic cells are dendritic cell specific antibodies. Some of the antibodies that may be used for this purpose are known in the art.

In some embodiments anti-ASGPR antibodies are used to target myelin sheath protein or components to dendritic cells. One example includes anti-dendritic cell immunoreceptor monoclonal antibody conjugates, wherein the conjugate comprises antigenic peptides that are loaded or chemically coupled to the antibody. Such antibodies are described in U.S. Pat. No. 8,236,934, incorporated herein by reference.

Peptide Linkers

In certain aspects, peptide linkers are used to link dendritic cell specific antibodies and myelin sheath protein or components to be presented. Peptide linkers may incorporate glycosylation sites or introduce secondary structure. Additionally these linkers increase the efficiency of expression or stability of the fusion protein and as a result the efficiency of antigen presentation to a dendritic cell. Linkers may include SSVSPTTSVHPTPTSVPPTPTKSSP (SEQ ID NO:1); PTSTPADSSTITPTATPTATPTIKG (SEQ ID NO:2); TVTPTATATPSAIVTTITPTATTKP (SEQ ID NO:3); or TNGSITVAATAPTVTPTVNATPSAA (SEQ ID NO:4). These examples and others are discussed in WO 2010/104747, the contents of which are incorporated herein by reference. Additional linkers useful for this purpose are described in US 2010/291082, the contents of which are incorporated herein by reference.

In certain aspects antibody domains, adjuvants antigens or peptide linkers may be bound by high-affinity interacting protein domains. In some embodiments a high-affinity interacting protein domains involves a cohesin-dockerin binding pair. A cohesin-dockerin binding pair may be recombinantly fused to an antibody domain, adjuvants, antigens or peptide linkers. In some aspects the dockerin is modified such that it is capable of binding to a cohesin domain when recombinantly encoded in an internal (non carboxy or non-amino terminal end) portion of a polypeptide. In certain aspects the linker region is not a peptide linker. An example of a non-peptide linker region may result as the product of chemical conjugation wherein the covalent bond that is formed between molecules is not a peptide bond.

Adjuvants

In other embodiments an immune adjuvant is directly fused or otherwise linked to the dendritic cell specific antibody in order to enhance the efficacy of the immunotherapeutic. In certain aspects the immune adjuvant may be a toll-like receptor (TLR) agonist. TLR agonists comprise flagellins from *Salmonella enterica* or *Vibrio cholerae*. In certain aspects the adjuvant in Flagellin-1 or Flagellin-2. TLR agonists may be specific for certain TLR classes (i.e., TLR5, TLR7 or TLR9 agonists) and may be presented in any combination or as any modification. Examples of such immune adjuvants are described in WO 2012/021834, the contents of which are incorporated herein by reference. Poly ICLC, a TLR3 ligand is also contemplated for use with myelin sheath protein or component DC targeting immunotherapeutic compositions. In some embodiments the DC targeting immunotherapeutic comprises myelin basic protein (MBP), myelin oligodendrocyte glycoprotein (MOG), proteolipid protein (PLP), myelin associated glycoprotein, peripheral myelin protein (PMP-22), Po protein, connexin 32 protein, Schwann cell myelin protein, or oligodendrocyte-myelin glycoprotein (OMgp) and Poly ICLC is delivered separately from the antibody antigen fusion polypeptide. In still additional embodiments, the immunotherapeutic comprises one or more different myelin sheath components as stated above. In one embodiment, the Poly ICLC is as described in U.S. Pat. No. 7,439,349, the contents of which are incorporated herein by reference. In one embodiment, the Poly ICLC is Hiltonol®. Interleukins are also contemplated as adjuvants that may be fused to a dendritic cell specific antibody or to a protein domain capable of binding with high affinity to a corresponding or complementary domain on a dendritic cell specific antibody. Non-limiting examples of such interleukins are IL-21, IL-2, IL-9 and IL-10. In some embodiments the interleukin proteins are human interleukins. In certain aspects the adjuvant is an HLA-DR antigen-associated invariant chain that augments antigen processing. In certain aspects the adjuvant is interferon alpha. In yet other embodiments the adjuvant is a toxin that will deliver a death signal to cells also receiving an myelin sheath protein or component, thereby augmenting immunotherapeutic efficiency. One example of such a toxin is PE38. Any adjuvant may be delivered in fused or conjugated form with a DC targeting immunotherapeutic or may be delivered concomitantly as part of the same composition or preparation without fusion or direct conjugation.

Tolerogenic Adjuvants

In certain embodiments the immune adjuvant may be a tolerogenic adjuvant. In certain instances a tolerogenic adjuvant may refer to an adjuvant that is utilized for tolerogenic immunization, where the aim of immunization with an antigen is to generate an immune response such that the antigen is tolerated by an immunized subject. In certain aspects, the goal of a tolerogenic adjuvant is to enhance tolerogenic immunization such that tolerance to an antigen is further enhanced. In certain embodiments a tolerogenic adjuvant is used to tolerize autoimmunity. In yet other aspects, a tolerogenic adjuvant is used to tolerize harmful autoimmunity. In some embodiments the tolerogenic adjuvant is an immunosuppressant. In yet other embodiments the tolerogenic adjuvant is dexamethasone, FK506 (Tacrolimus), cholera toxin B subunit, *Escherichia coli* heat-labile enterotoxin B subunit, IFN-beta, glucocorticoids, vitamin D3, or vitamin D3 analogues. In certain aspects the tolerogenic adjuvant is administered concurrently with a DC targeting immunotherapeutic. In other aspects a tolerogenic adjuvant is administered before or after administration of a DC targeting immunotherapeutic. In yet other embodiments two or more tolerogenic adjuvants are administered concurrently, before or after administration of a DC targeting immunotherapeutic. In certain aspects, the tolerogenic adjuvant may be fused, conjugated or otherwise linked to the DC targeting immunotherapeutic. In one embodiment, the tolerogenic adjuvant is interleukin-10 (IL-10). In another embodiment IL-10 is co-administered with the DC targeting immunotherapeutic. In certain aspects, IL-10 is fused by recombinant methods. In other aspects IL-10 is conjugated. In other embodiments IL-10 is linked by coupling or other modular domains.

Constructs

The sequences given below, when presented as antibody H or L chain or protein secreted by mammalian cells are shown as amino acids without signal peptide (i.e., as 'mature' secreted protein), while the DNA sequences are the entire coding region including signal sequences if present.

All examples of H chain constructs are typically used in co-transfection of CHO cells with matching L chain vectors. Also, in some embodiments immunotherapeutics will have humanized variable regions, which have been described for anti-ASGPR_49C11, anti-CD40 12E12, anti-Langerin 15B10, anti-DCIR 9E8, and anti-LOX-1 15C4.

Anti-ASGPR heavy chain and light chains may be selected from the following:

Anti-DC ASGPR mAbs

[mAnti-ASGPR-49C11-7H-LV-hIgG4H-C]
(SEQ ID NO.: 5)
DVQLQESGPDLVKPSQSLSLTCTVTGYSITSGYSWHWIRQFPGNKLEWMGYI

LFSGSTNYNPSLKSRISITRDTSKNQFFLQLNSVTTEDTATYFCARSNYGSFASWGQG

TLVTVSAAKTTGPSVFPLAPCSRSTSESTAALGCLVKDYFPEPVTVSWNSGALTSGVH

TFPAVLQSSGLYSLSSVVTVPSSSLGTKTYTCNVDHKPSNTKVDKRVESKYGPPCPPC

PAPEFEGGPSVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEKTISKAKGQP

REPQVYTLPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGKAS.

The above sequence is a chimera between the H chain variable
region of the mAb 49C11 (shown underlined) and the C region of
hIgG4.

[mAnti-ASGPR-49C11-7K-LV-hIgGK-C] is the corresponding L chain
chimera (sequence below, variable region underlined)
(SEQ ID NO.: 6)
QIVLTQSPAIMSASPGEKVTMTCSASSSVSHMHWYQQKSGTSPKRWIYDTSR

LASGVPARFSGSGSGTSYSLTISSMEAEDAATYYCQQWSSHPWSFGGGTKLEIKRTV

AAPSVFIFPPSDEQLKSGTASVVCLLNNFYPREAKVQWKVDNALQSGNSQESVTEQD

SKDSTYSLSSTLTLSKADYEKHKVYACEVTHQGLSSPVTKSFNRGEC.

| Anti-DC ASGPR mAbs |
| --- |

[mAnti-ASGPR-4G2.2_Hv-V-hIgG4H-C]
(SEQ ID NO.: 7)

<u>QIQLVQSGPELKKPGETVKISCKASGYTFTNYGMNWVKQVPGKGLRWMGW</u>

<u>MDTFTGEPTYADDFKGRFAFSLETSASTAYLQINSLKNEDTATYFCARGGILRLNYFD</u>

<u>YWGQGTTLTVSSAKTKGPSVFPLAPCSRSTSESTAALGCLVKDYFPEPVTVSWNSGA</u>

LTSGVHTFPAVLQSSGLYSLSSVVTVPSSSLGTKTYTCNVDHKPSNTKVDKRVESKY

GPPCPPCPAPEFEGGPSVFLFPPKPKDTLMISRTPEVTCVVVDVSQEDPEVQFNWYVD

GVEVHNAKTKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLSLSLGKAS.

The above sequence is a chimera between the H chain variable of the mAb 4G2.2 (shown underlined) and the C region of hIgG4.

[mAnti-ASGPR-4G2.2_Kv-V-hIgGK-C] is the corresponding L chain chimera (sequence below, variable region underlined)
(SEQ ID NO.: 8)

<u>DIQMTQSSSSFSVSLGDRVTITCKASEDIYNRLGWYQQKPGNAPRLLISGATSL</u>

<u>ETGVPSRFSGSGSGKDYALSITSLQTEDLATYYCQQCWTSPYTFGGGTKLEIKRTVAA</u>

PSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEC.

[mAnti-ASGPR-5F10H-LV-hIgG4H-C] is
(SEQ ID NO.: 9)

<u>EVQLQQSGPELVKPGASVKMSCKASGYTFTDYYMKWVKQSHGKSLEWIGDI</u>

<u>NPNYGDTFYNQKFEGICATLTVDKSSRTAYMQLNSLTSEDSAVYYCGRGDYGYFDV</u>

<u>WGAGTTVTVSSAKTKGPSVFPLAPCSRSTSESTAALGCLVKDYFPEPVTVSWNSGAL</u>

TSGVHTFPAVLQSSGLYSLSSVVTVPSSSLGTKTYTCNVDHKPSNTKVDKRVESKYG

PPCPPCPAPEFEGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSSIEKTISK

AKGQPREPQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLLSLGKAS.

The above sequence is a chimera between the H chain variable of the mAb 5F10H (shown underlined) and the C region of hIgG4.

[mAnti-ASGPR-5F10K-LV-hIgGK-C] is the corresponding L chain chimera (sequence below, variable region underlined)
(SEQ ID NO.: 10)

<u>DIVMTQSHKFMSTSVGDRVSITCKASQDVGTAVAWYQQKPGQSPKLLIYWA</u>

<u>STRHTGVPDRFTGSGSGTDFTLTINNVQSEDLADYFCQQYSSNPYMFGGGTKLEIKRT</u>

VAAPSVFIFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC.

[mAnti-ASGPR1H11H-V-hIgG4H-C] is
(SEQ ID NO.: 11)

<u>QLQQSGPELVKPGASVKISCKTSGYTFTEYTMHWVRQSHGKSLEWIGGINPIN</u>

<u>GGPTYNQKFKGKATLTVDKSSSTAYMELRSLTSEDSAVYYCARWDYGSRDVMDY</u>

<u>WGQGTSVTVSSAKTKGPSVFPLAPCSRSTSESTAALGCLVKDYFPEPVTVSWNSGAL</u>

TSGVHTFPAVLQSSGLYSLSSVVTVPSSSLGTKTYTCNVDHKPSNTKVDKRVESKYG

PPCPPCPAPEFEGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSSIEKTISK

Anti-DC ASGPR mAbs

AKGQPREPQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSLGKAS.

The above sequence is a chimera between the H chain variable of the mAb 1H11 (shown underlined) and the C region of hIgG4.

[mAnti-ASGPR1H11K-LV-hIgGK-C] is the corresponding L chain chimera (sequence below, variable region underlined)

(SEQ ID NO.: 12)

NIVMTQSPKSMSMSVGERVTLSCKASENVGTYVSWYQQRPEQSPKWYGAS

NRYTGVPDRFTGSGSATDFTLTISSVQAEDLADYHCGQTYSYIFTFGSGTKLEIKRTV

AAPSVFIFPPSDEQLKSGTASVVCLLNNFYPREAKVQWKVDNALQSGNSQESVTEQD

SKDSTYSLSSTLTLSKADYEKHKVYACEVTHQGLSSPVTKSFNRGEC.

Examples of full length DC targeting antibody/antigen constructs are as follows:

Anti-DC ASGPR mAbs mAnti-ASGPR_49C11_7H-LV-hIgG4H-C-Flex-v1-hMBP
(LV-hIgG4H-C sequence underlined, Flex-v1 sequence in bold, hMBP sequence double underlined)

(SEQ ID NO: 13)

ATGAGAGCGCTGATTCTTTTGTGCCTGTTCACAGCCTTTCCTGGTATCCTGTCTGA

TGTGCAGCTTCAGGAGTCAGGACCTGACCTGGTGAAACCTTCTCAGTCACTTTCA

CTCACCTGCACTGTCACTGGCTACTCCATCACCAGTGGTTATAGCTGGCACTGGA

TCCGGCAGTTTCCAGGAAACAAACTGGAATGGATGGGCTACATACTCTTCAGTGG

TAGCACTAACTACAACCCATCTCTGAAAAGTCGAATCTCTATCACTCGAGACACA

TCCAAGAACCAGTTCTTCCTGCAGTTGAATTCTGTGACTACTGAGGACACAGCCA

CATATTTCTGTGCAAGATCTAACTATGGTTCCTTTGCTTCCTGGGGCCAAGGGACT

CTGGTCACTGTCTCTGCAGCCAAAACAACGGGCCCATCCGTCTTCCCCCTGGCGC

CCTGCTCCAGGAGCACCTCCGAGAGCACAGCCGCCCTGGGCTGCCTGGTCAAGG

ACTACTTCCCCGAACCGGTGACGGTGTCGTGGAACTCAGGCGCCCTGACCAGCG

GCGTGCACACCTTCCCGGCTGTCCTACAGTCCTCAGGACTCTACTCCCTCAGCAG

CGTGGTGACCGTGCCCTCCAGCAGCTTGGGCACGAAGACCTACACCTGCAACGT

AGATCACAAGCCCAGCAACACCAAGGTGGACAAGAGAGTTGAGTCCAAATATGG

TCCCCCATGCCCACCCTGCCCAGCACCTGAGTTCGAAGGGGGACCATCAGTCTTC

CTGTTCCCCCCAAAACCCAAGGACACTCTCATGATCTCCCGGACCCCTGAGGTCA

CGTGCGTGGTGGTGGACGTGAGCCAGGAAGACCCCGAGGTCCAGTTCAACTGGT

ACGTGGATGGCGTGGAGGTGCATAATGCCAAGACAAAGCCGCGGGAGGAGCAG

TTCAACAGCACGTACCGTGTGGTCAGCGTCCTCACCGTCCTGCACCAGGACTGGC

TGAACGGCAAGGAGTACAAGTGCAAGGTCTCCAACAAAGGCCTCCCGTCCTCCA

TCGAGAAAACCATCTCCAAAGCCAAAGGGCAGCCCCGAGAGCCACAGGTGTACA

CCCTGCCCCCATCCCAGGAGGAGATGACCAAGAACCAGGTCAGCCTGACCTGCC

TGGTCAAAGGCTTCTACCCCAGCGACATCGCCGTGGAGTGGGAGAGCAATGGGC

AGCCGGAGAACAACTACAAGACCACGCCTCCCGTGCTGGACTCCGACGGCTCCT

-continued

Anti-DC ASGPR mAbs

```
TCTTCCTCTACAGCAGGCTAACCGTGGACAAGAGCAGGTGGCAGGAGGGGAATG

TCTTCTCATGCTCCGTGATGCATGAGGCTCTGCACAACCACTACACACAGAAGAG

CCTCTCCCTGTCTCTGGGTAAAGCTAGTCAGACCCCCACCAACACCATCAGCGTG

ACCCCCACCAACAACAGCACCCCCACCAACAACAGCAACCCCAAGCCCAACCCC

GCTAGTGCATCACAAAAGCGGCCTTCACAACGGCACGGATCTAAATATCTGGCG

ACAGCCTCTACCATGGATCACGCCAGGCATGGCTTTCTGCCCAGGCACAGAGATA

CTGGAATCTTGGACTCCATCGGCAGGTTCTTTGGCGGCGACCGAGGGGCTCCCAA

GAGAGGGAGTGGCAAGGATAGCCATCATCCAGCCCGAACAGCCCACTACGGAAG

CCTGCCGCAGAAAAGCCACGGTCGCACGCAGGATGAAAATCCCGTTGTGCACTT

CTTCAAAAACATTGTGACCCCACGAACTCCTCCACCTTCCCAAGGCAAGGGCAGA

GGTCTCAGTCTCAGCCGGTTCAGTTGGGGGGCCGAGGGCCAGAGACCCCGGATTT

GGTTATGGGGGAAGGGCTAGCGACTACAAGTCTGCACATAAGGGGTTCAAAGGG

GTCGACGCACAGGGAACCCTGTCCAAAATATTTAAGCTTGGTGGCCGCGACTCCC

GCTCAGGCTCTCCCATGGCTCGGCGCTGA
```

(SEQ ID NO: 14)
<u>DVQLQESGPDLVKPSQSLSLTCTVTGYSITSGYSWHWIRQFPGNKLEWMGYILFSGS</u>
<u>TNYNPSLKSRISITRDTSKNQFFLQLNSVTTEDTATYFCARSNYGSFASWGQGTLVTV</u>
<u>SAAKTTGPSVFPLAPCSRSTSESTAALGCLVKDYFPEPVTVSWNSGALTSGVHTFPAV</u>
<u>LQSSGLYSLSSVVTVPSSSLGTKTYTCNVDHICPSNTKVDKRVESKYGPPCPPCPAPEF</u>
<u>EGGPSVFLFPPKPKDTLMISRTPEVTCVVVDVSQEDPEVQFNWYVDGVEVHNAKTK</u>
<u>PREEQFNSTYRVVSVLTVLHQDWLNGKEYKCKVSNKGLPSSIEKTISKAKGQPREPQ</u>
<u>VYTLPPSQEEMTKNQVSLTCLVKGFYPSDIAVEWESNGQPENNYKTTPPVLDSDGSF</u>
<u>FLYSRLTVDKSRWQEGNVFSCSVMHEALHNHYTQKSLSLSLGKAS</u>QTPTNTISVTP
TNNSTPTNNSNPKPNPASA<u>SQKRPSQRHGSKYLATASTMDHARHGFLPRHRDTGIL</u>
<u>DSIGRFFGGDRGAPKRGSGKDSHHPARTAHYGSLPQKSHGRTQDENPVVHFFKNIVT</u>
<u>PRTPPPSQGKGRGLSLSRFSWGAEGQRPGFYGGRASDYKSAHKFKGVDAQGTLS</u>
<u>KIFKLGGRDSRSGSPMARR</u> mAnti-ASGPR_49C11_7K-LV-hIgGK-C
(LV-hIgGK-C sequence underlined)

(SEQ ID NO: 15)
```
ATGGATTTTCAAGTGCAGATTTTCAGCTTCCTGCTAATCAGTGCCTCAGTCATAAT

ATCCAGAGGACAAATTGTTCTCACCCAGTCTCCAGCAATCATGTCTGCATCTCCA

GGGGAGAAGGTCACCATGACCTGCAGTGCCAGCTCAAGTGTAAGTCACATGCAC

TGGTACCAGCAGAAGTCAGGCACTTCCCCCAAAAGATGGATTTATGACACATCC

AGACTGGCTTCTGGAGTCCCTGCTCGCTTCAGTGGCAGTGGGTCTGGGACCTCTT

ACTCTCTCACAATCAGCAGCATGGAGGCTGAAGATGCTGCCACTTATTACTGCCA

GCAGTGGAGTAGTCACCCATGGTCGTTCGGTGGAGGCACCAAACTCGAGATCAA

ACGAACTGTGGCTGCACCATCTGTCTTCATCTTCCCGCCATCTGATGAGCAGTTG

AAATCTGGAACTGCCTCTGTTGTGTGCCTGCTGAATAACTTCTATCCCAGAGAGG

CCAAAGTACAGTGGAAGGTGGATAACGCCCTCCAATCGGGTAACTCCCAGGAGA
```

| Anti-DC ASGPR mAbs |
|---|
| GTGTCACAGAGCAGGACAGCAAGGACAGCACCTACAGCCTCAGCAGCACCCTGA |
| CGCTGAGCAAAGCAGACTACGAGAAACACAAAGTCTATGCCTGCGAAGTCACCC |
| ATCAGGGCCTGAGCTCGCCCGTCACAAAGAGCTTCAACAGGGGAGAGTGTTAG |

(SEQ ID NO: 16)
QIVLTQSPAIMSASPGEKVTMTCSASSSVSHMHWYQQKSGTSPKRWIYDTSRLASGV
PARFSGSGSGTSYSLTISSMEAEDAATYYCQQWSSHPWSFGGGTKLEIKRTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC mAnti-ASGPR_49C11_7H-LV-hIgG4H-C-hMOG
(LV-hIgG4H-C sequence underlined; hMOG sequence bold)

(SEQ ID NO: 17)
ATGAGAGCGCTGATTCTTTTGTGCCTGTTCACAGCCTTTCCTGGTATCCTGTCTGA
TGTGCAGCTTCAGGAGTCAGGACCTGACCTGGTGAAACCTTCTCAGTCACTTTCA
CTCACCTGCACTGTCACTGGCTACTCCATCACCAGTGGTTATAGCTGGCACTGGA
TCCGGCAGTTTCCAGGAAACAAACTGGAATGGATGGGCTACATACTCTTCAGTGG
TAGCACTAACTACAACCCATCTCTGAAAAGTCGAATCTCTATCACTCGAGACACA
TCCAAGAACCAGTTCTTCCTGCAGTTGAATTCTGTGACTACTGAGGACACAGCCA
CATATTTCTGTGCAAGATCTAACTATGGTTCCTTTGCTTCCTGGGGCCAAGGGACT
CTGGTCACTGTCTCTGCAGCCAAAACAACGGGCCCATCCGTCTTCCCCCTGGCGC
CCTGCTCCAGGAGCACCTCCGAGAGCACAGCCGCCCTGGGCTGCCTGGTCAAGG
ACTACTTCCCCGAACCGGTGACGGTGTCGTGGAACTCAGGCGCCCTGACCAGCG
GCGTGCACACCTTCCCGGCTGTCCTACAGTCCTCAGGACTCTACTCCCTCAGCAG
CGTGGTGACCGTGCCCTCCAGCAGCTTGGGCACGAAGACCTACACCTGCAACGT
AGATCACAAGCCCAGCAACACCAAGGTGGACAAGAGAGTTGAGTCCAAATATGG
TCCCCCATGCCCACCCTGCCCAGCACCTGAGTTCGAAGGGGGACCATCAGTCTTC
CTGTTCCCCCCAAAACCCAAGGACACTCTCATGATCTCCCGGACCCCTGAGGTCA
CGTGCGTGGTGGTGGACGTGAGCCAGGAAGACCCCGAGGTCCAGTTCAACTGGT
ACGTGGATGGCGTGGAGGTGCATAATGCCAAGACAAAGCCGCGGGAGGAGCAG
TTCAACAGCACGTACCGTGTGGTCAGCGTCCTCACCGTCCTGCACCAGGACTGGC
TGAACGGCAAGGAGTACAAGTGCAAGGTCTCCAACAAAGGCCTCCCGTCCTCCA
TCGAGAAAACCATCTCCAAAGCCAAAGGGCAGCCCCGAGAGCCACAGGTGTACA
CCCTGCCCCCATCCCAGGAGGAGATGACCAAGAACCAGGTCAGCCTGACCTGCC
TGGTCAAAGGCTTCTACCCCAGCGACATCGCCGTGGAGTGGGAGAGCAATGGGC
AGCCGGAGAACAACTACAAGACCACGCCTCCCGTGCTGGACTCCGACGGCTCCT
TCTTCCTCTACAGCAGGCTAACCGTGGACAAGAGCAGGTGGCAGGAGGGGAATG
TCTTCTCATGCTCCGTGATGCATGAGGCTCTGCACAACCACTACACACAGAAGAG
CCTCTCCCTGTCTCTGGGTAAAGCTAGTGGTCAGTTTAGAGTCATTGGGCCCAGA
CACCCTATAAGGGCTCTTGTGGGAGACGAGGTCGAGCTGCCGTGTCGCATTAGTC
CAGGCAAAAACGCCACAGGGATGGAAGTGGGGTGGTACAGGCCTCCCTTCTCTA
GGGTTGTGCATCTCTACCGCAACGGCAAAGATCAGGATGGAGATCAAGCTCCTG
AATATCGGGGCCGGACTGAGCTGCTCAAGGACGCGATCGGCGAGGGTAAGGTGA

| Anti-DC ASGPR mAbs |
|---|

CCTTGCGCATCCGAAATGTTAGATTCAGCGATGAAGGCGGATTTACGTGCTTCTT

TCGGGACCACTCATACCAGGAGGAAGCCGCAATGGAACTGAAGGTGGAGGACCC

CTTCTATTGGGTATCCCCAGCTAGCTGA (SEQ ID NO: 18)
<u>DVQLQESGPDLVKPSQSLSLTCTVTGYSITSGYSWHWIRQFPGNKLEWMGYILFSGS</u>

<u>TNYNPSLKSRISITRDTSKNQFFLQLNSVTTEDTATYFCARSNYGSFASWGQGTLVTV</u>

<u>SAAKTTGPSVFPLAPCSRSTSESTAALGCLVKDYFPEPVTVSWNSGALTSGVHTFPAV</u>

<u>LQSSGLYSLSSVVTVPSSSLGTKTYTCNVDHKPSNTKVDKRVESKYGPPCPPCPAPEF</u>

<u>EGGPSVFLFPPKPKDTLMISRTPEVTCVVVDVSQEDPEVQFNWYVDGVEVHNAKTK</u>

<u>PREEQFNSTYRVVSVLTVLHQDWLNGKEYKCKVSNKGLPSSIEKTISKAKGQPREPQ</u>

<u>VYTLPPSQEEMTKNQVSLTCLVKGFYPSDIAVEWESNGQPENNYKTTPPVLDSDGSF</u>

<u>FLYSRLTVDKSRWQEGNVFSCSVMHEALHNHYTQKSLSLSLGKAS</u>GQFRVIGPRHP

IRALVGDEVELPCRISPGKNATGMEVGWYRPPFSRVVHLYRNGKDQDGDQAPE

YRGRTELLKDAIGEGKVTLRIRNVRFSDEGGFTCFFRDHSYQEEAAMELKVEDP

FYWVSPAS mAnti-ASGPR_49C11_7K-LV-hIgGK-C
(LV-hIgGK-C sequence underlined)
(SEQ ID NO: 19)
ATGGATTTTCAAGTGCAGATTTTCAGCTTCCTGCTAATCAGTGCCTCAGTCATAAT

ATCCAGAGGACAAATTGTTCTCACCCAGTCTCCAGCAATCATGTCTGCATCTCCA

GGGGAGAAGGTCACCATGACCTGCAGTGCCAGCTCAAGTGTAAGTCACATGCAC

TGGTACCAGCAGAAGTCAGGCACTTCCCCCAAAAGATGGATTTATGACACATCC

AGACTGGCTTCTGGAGTCCCTGCTCGCTTCAGTGGCAGTGGGTCTGGGACCTCTT

ACTCTCTCACAATCAGCAGCATGGAGGCTGAAGATGCTGCCACTTATTACTGCCA

GCAGTGGAGTAGTCACCCATGGTCGTTCGGTGGAGGCACCAAACTCGAGATCAA

ACGAACTGTGGCTGCACCATCTGTCTTCATCTTCCCGCCATCTGATGAGCAGTTG

AAATCTGGAACTGCCTCTGTTGTGTGCCTGCTGAATAACTTCTATCCCAGAGAGG

CCAAAGTACAGTGGAAGGTGGATAACGCCCTCCAATCGGGTAACTCCCAGGAGA

GTGTCACAGAGCAGGACAGCAAGGACAGCACCTACAGCCTCAGCAGCACCCTGA

CGCTGAGCAAAGCAGACTACGAGAAACACAAAGTCTATGCCTGCGAAGTCACCC

ATCAGGGCCTGAGCTCGCCCGTCACAAAGAGCTTCAACAGGGGAGAGTGTTAG (SEQ ID NO: 20)
<u>QIVLTQSPAIMSASPGEKVTMTCSASSSVSHMHWYQQKSGTSPKRWIYDTSRLASGV</u>

<u>PARFSGSGSGTSYSLTISSMEAEDAATYYCQQWSSHPWSFGGGTKLEIKRTVAAPSVF</u>

<u>IFPPSDEQLKSGTASVVCLLNNFYPREAKVQWKVDNALQSGNSQESVTEQDSKDSTY</u>

<u>SLSSTLTLSKADYEKHKVYACEVTHQGLSSPVTKSFNRGEC</u>

6xHis-Cohesin-hMOG
(6xHis underlined; Cohesin in bold; hMOG double underlined)
(SEQ ID NO: 21)
ATGGATCCCAAAGGATCCCTTTCCTGGAGAATACTTCTGTTTCTCTCCCTGGCTTT

TGAGTTGAGCTACGGACTCGACATCACATCCCACCATCACCATCACCATGACGAT

CTGGATGCAGTAAGGATTAAAGTGGACACAGTAAATGCAAAACCGGGAGACACA

-continued

| Anti-DC ASGPR mAbs |
|---|

GTAAGAATACCTGTAAGATTCAGCGGTATACCATCCAAGGGAATAGCAAACTGT

GACTTTGTATACAGCTATGACCCGAATGTACTTGAGATAATAGAGATAGAACCG

GGAGACATAATAGTTGACCCGAATCCTGACAAGAGCTTTGATACTGCAGTATATC

CTGACAGAAAGATAATAGTATTCCTGTTTGCAGAAGACAGCGGAACAGGAGCGT

ATGCAATAACTAAAGACGGAGTATTTGCTACGATAGTAGCGAAAGTAAAAGAAG

GAGCACCTAACGGACTCAGTGTAATCAAATTTGTAGAAGTAGGCGGATTTGCGA

ACAATGACCTTGTAGAACAGAAGACACAGTTCTTTGACGGTGGAGTAAATGTTG

GAGATACAACAGAACCTGCAACACCTACAACACCTGTAACAACACCGACAACAA

CAGATGATCTGGATGCAGCTAGTGGTCAGTTTAGAGTCATTGGGCCCAGACACCC

TATAAGGGCTCTTGTGGGAGACGAGGTCGAGCTGCCGTGTCGCATTAGTCCAGGC

AAAAACGCCACAGGGATGGAAGTGGGGTGGTACAGGCCTCCCTTCTCTAGGGTT

GTGCATCTCTACCGCAACGGCAAAGATCAGGATGGAGATCAAGCTCCTGAATAT

CGGGGCCGGACTGAGCTGCTCAAGGACGCGATCGGCGAGGGTAAGGTGACCTTG

CGCATCCGAAATGTTAGATTCAGCGATGAAGGCGGATTTACGTGCTTCTTTCGGG

ACCACTCATACCAGGAGGAAGCCGCAATGGAACTGAAGGTGGAGGACCCCTTCT

ATTGGGTATCCCCAGCTAGCTGA (SEQ ID NO: 22)
LDITSHHHHHHDDLDAVRIKVDTVNAKPGDTVRIPVRFSGIPSKGIANCDFVYSYD

PNVLEIIEIEPGDIIVDPNPDKSFDTAVYPDRKIIVFLFAEDSGTGAYAITKDGVFA

TIVAKVKEGAPNGLSVIKFVEVGGFANNDLVEQKTQFFDGGVNVGDTTEPATPT

TPVTTPTTTDDLDAAS<u>GQFRVIGPRHPIRALVGDEVELPCRISPGKNATGMEVGWYR</u>

<u>PPFSRVVHLYRNGKDQDGDQAPEYRGRTELLKDAIGEGKVTLRIRNVRFSDEGGFTC</u>

<u>FFRDHSYQEEAAMELKVEDPFYWVSPAS</u>

6xHis-Cohesin-hMBP
(6xHis underlined; Cohesin in bold; hMBP double underlined)

(SEQ ID NO: 23)
ATGGGCAGCAGCCATCATCATCATCATCACAGCAGCGGCCTGGTGCCGCGCGGC

AGCCATATGGCTAGTATGGATCTGGATGCAGTAAGGATTAAAGTGGACACAGTA

AATGCAAAACCGGGAGACACAGTAAATATACCTGTAAGATTCAGTGGTATACCA

TCCAAGGGAATAGCAAACTGTGACTTTGTATACAGCTATGACCCGAATGTACTTG

AGATAATAGAGATAAAACCGGGAGAATTGATAGTTGACCCGAATCCTACCAAGA

GCTTTGATACTGCAGTATATCCTGACAGAAAGATGATAGTATTCCTGTTTGCGGA

AGACAGCGGAACAGGAGCGTATGCAATAACTAAAGACGGAGTATTTGCTACGAT

AGTAGCGAAAGTAAAAGAAGGAGCACCTAACGGGCTCAGTGTAATCAAATTTGT

AGAAGTAGGCGGATTTGCGAACAATGACCTTGTAGAACAGAAGACACAGTTCTT

TGACGGTGGAGTAAATGTTGGAGATACAACAGAACCTGCAACACCTACAACACC

TGTAACAACACCGACAACAACAGATGATCTAGATGCAGCTAGTGCATCACAAAA

GCGGCCTTCACAACGGCACGGATCTAAATATCTGGCGACAGCCTCTACCATGGAT

CACGCCAGGCATGGCTTTCTGCCCAGGCACAGAGATACTGGAATCTTGGACTCCA

TCGGCAGGTTCTTTGGCGGCGACCGAGGGGCTCCCAAGAGAGGGAGTGGCAAGG

ATAGCCATCATCCAGCCCGAACAGCCCACTACGGAAGCCTGCCGCAGAAAAGCC

Anti-DC ASGPR mAbs

ACGGTCGCACGCAGGATGAAAATCCCGTTGTGCACTTCTTCAAAAACATTGTGAC

CCCACGAACTCCTCCACCTTCCCAAGGCAAGGGCAGAGGTCTCAGTCTCAGCCGG

TTCAGTTGGGGGGCCGAGGGCCAGAGACCCGGATTTGGTTATGGGGGAAGGGCT

AGCGACTACAAGTCTGCACATAAGGGGTTCAAAGGGGTCGACGCACAGGGAACC

CTGTCCAAAATATTTAAGCTTGGTGGCCGCGACTCCCGCTCAGGCTCTCCCATGG

CTCGGCGCTGA (SEQ ID NO: 24)

MGSS<u>HHHHHH</u>SSGLVPRGSHMASMDLDAVRIKVDTVNAKPGDTVNIPVRFSGIPS

KGIANCDFVYSYDPNVLEIIEIKPGELIVDPNPTKSFDTAVYPDRKMIVFLFAEDS

GTGAYAITKDGVFATIVAKVKEGAPNGLSVIKFVEVGGFANNDLVEQKTQFFDG

GVNVGDTTEPATPTTPVTTPTTTDDLDAASAS<u>QKRPSQRHGSKYLATASTMDHAR</u>

<u>HGFLPRHRDTGILDSIGRFFGGDRGAPKRGSGKDSHHPARTAHYGSLPQKSHGRTQD</u>

<u>ENPVVHFFKNIVTPRTPPPSQGKGRGLSLSRFSWGAEGQRPGFGYGGRASDYKSAHK</u>

<u>GFKGVDAQGTLSKIFKLGGRDSRSGSPMARR</u> manti-hASGPR_6.3H9.1D11H-LV-hIgG4H-C-hMOG
(LV-hIgG4H-C underlined, variable region bold underline;
hMOG in bold)

(SEQ ID NO: 25)

ATGGAATGGAGCGGGGTCTTTATCTTTCTCCTGTCAGTAACTGCAGGTGCCCACT

CCCAGGTCCAGCTGCAGCAGTCTGGAGCTGAGCTGGTAAGGCCTGGGACTTCAG

TGAAGATGTCCTGCGAGGCTGCTAGATTCACCTTCAGTAACTACTGGATTGGTTG

GGTAAAGCAGAGGCCTGGACATGGCCTTGAGTGGATTGGAGATATTTTCCCTGG

AGGTGATTATACTAACTACAATAAGAAATTCAAGGACAAGGCCACACTGACTGC

AGACACATCCTCCAGCACAGCCTACATGCAGCTCAGCAGCCTGACATCTGAGGA

CTCTGCCATCTATTACTGTGCAAGATCGGACTACGGTGGTTACTACGTCTTTGACT

ACTGGGGCCAAGGCACCACTCTCACAGICTCCTCAGCCAAAACAAAGGGCCCAT

CCGTCTTCCCCCTGGCGCCCTGCTCCAGGAGCACCTCCGAGAGCACAGCCGCCCT

GGGCTGCCTGGTCAAGGACTACTTCCCCGAACCGGTGACGGTGTCGTGGAACTCA

GGCGCCCTGACCAGCGGCGTGCACACCTTCCCGGCTGTCCTACAGTCCTCAGGAC

TCTACTCCCTCAGCAGCGTGGTGACCGTGCCCTCCAGCAGCTTGGGCACGAAGAC

CTACACCTGCAACGTAGATCACAAGCCCAGCAACACCAAGGTGGACAAGAGAGT

TGAGTCCAAATATGGTCCCCCATGCCCACCCTGCCCAGCACCTGAGTTCGAAGGG

GGACCATCAGTCTTCCTGTTCCCCCCAAAACCCAAGGACACTCTCATGATCTCCC

GGACCCCTGAGGTCACGTGCGTGGTGGTGGACGTGAGCCAGGAAGACCCCGAGG

TCCAGTTCAACTGGTACGTGGATGGCGTGGAGGTGCATAATGCCAAGACAAAGC

CGCGGGAGGAGCAGTTCAACAGCACGTACCGTGTGGTCAGCGTCCTCACCGTCCT

GCACCAGGACTGGCTGAACGGCAAGGAGTACAAGTGCAAGGTCTCCAACAAAGG

CCTCCCGTCCTCCATCGAGAAAACCATCTCCAAAGCCAAAGGGCAGCCCCGAGA

GCCACAGGTGTACACCCTGCCCCCATCCCAGGAGGAGATGACCAAGAACCAGGT

CAGCCTGACCTGCCTGGTCAAAGGCTTCTACCCCAGCGACATCGCCGTGGAGTGG

GAGAGCAATGGGCAGCCGGAGAACAACTACAAGACCACGCCTCCCGTGCTGGAC

| Anti-DC ASGPR mAbs |
|---|

TCCGACGGCTCCTTCTTCCTCTACAGCAGGCTAACCGTGGACAAGAGCAGGTGGC

AGGAGGGGAATGTCTTCTCATGCTCCGTGATGCATGAGGCTCTGCACAACCACTA

CACACAGAAGAGCCTCTCCCTGTCTCTGGGTAAAGCTAGTGGTCAGTTTAGAGTC

ATTGGGCCCAGACACCCTATAAGGGCTCTTGTGGGAGACGAGGTCGAGCTGCCG

TGTCGCATTAGTCCAGGCAAAAACGCCACAGGGATGGAAGTGGGGTGGTACAGG

CCTCCCTTCTCTAGGGTTGTGCATCTCTACCGCAACGGCAAAGATCAGGATGGAG

ATCAAGCTCCTGAATATCGGGGCCGGACTGAGCTGCTCAAGGACGCGATCGGCG

AGGGTAAGGTGACCTTGCGCATCCGAAATGTTAGATTCAGCGATGAAGGCGGAT

TTACGTGCTTCTTTCGGGACCACTCATACCAGGAGGAAGCCGCAATGGAACTGAA

GGTGGAGGACCCCTTCTATTGGGTATCCCCAGCTAGCTGA (SEQ ID NO: 26)

QVQLQQSGAELVRPGTSVKMSCEAARFTFSNYWIGWVKQRPGHGLEWIGDIFP

GGDYTNYNICKFKDKATLTADTSSSTAYMQLSSLTSEDSAIYYCARSDYGGYYVF

DYWGQGTTLTVSSAKTKGPSVFPLAPCSRSTSESTAALGCLVKDYFPEPVTVSWNS

GALTSGVHTFPAVLQSSGLYSLSSVVTVPSSSLGTKTYTCNVDHKPSNTKVDKRVES

KYGPPCPPCPAPEFEGGPSVFLFPPKPKDTLMISRTPEVTCVVVDVSQEDPEVQFNWY

VDGVEVHNAKTKPREEQFNSTYRVVSVLTVLHQDWLNGKEYKCKVSNKGLPSSIEK

TISKAKGQPREPQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQKSLSLSLGKA

SGQFRVIGPRHPIRALVGDEVELPCRISPGKNATGMEVGWYRPPFSRVVHLYRN

GKDQDGDQAPEYRGRTELLKDAIGEGKVTLRIRNVRFSDEGGFTCFFRDHSYQE

EAAMELKVEDPFYWVSPAS manti-hASGPR 6.3H9.1D11K-LV-hIgGK-C
(LV-hIgGK-C underlined, variable region bold underline)

(SEQ ID NO: 27)

ATGGATTCACAGGCCCAGGTTCTTATGTTACTGCTGCTATGGGTATCTGGTACCT

GTGGGGACATTGTGATGTCACAGTCTCCATCCTCCCTAGCTGTGTCAGTTGGAGA

GAAGGTTACTATGAGCTGCAAGTCCAGTCAGAACCTTTTATATAGTAGCAATCAA

AAGAACTACTTGGCCTGGTACCAGCAGAAACCAGGGCAGTCTCCTAAACTGCTG

ATTTACTGGGCATCCACTAGGGAATCTGGGGTCCCTGATCGCTTCACAGGCAGTG

GATCTGGGACAGATTTCACICTCACCATCAGCAGTGTGAAGGCTGAAGACCTGGC

AGTCTATTACTGTCAGCAATATTATAGCTATCCTTACACGTTCGGAGGGGGGACC

AAGCTCGAGATCAAACGAACTGTGGCTGCACCATCTGTCTTCATCTTCCCGCCAT

CTGATGAGCAGTTGAAATCTGGAACTGCCTCTGTTGTGTGCCTGCTGAATAACTT

CTATCCCAGAGAGGCCAAAGTACAGTGGAAGGTGGATAACGCCCTCCAATCGGG

TAACTCCCAGGAGAGTGTCACAGAGCAGGACAGCAAGGACAGCACCTACAGCCT

CAGCAGCACCCTGACGCTGAGCAAAGCAGACTACGAGAAACACAAAGTCTATGC

CTGCGAAGTCACCCATCAGGGCCTGAGCTCGCCCGTCACAAAGAGCTTCAACAG

GGGAGAGTGTGCTAGCTGA

-continued

| Anti-DC ASGPR mAbs |
|---|
| (SEQ ID NO: 28)<br>DIVMSQSPSSLAVSVGEKVTMSCKSSQNLLYSSNQKNYLAWYQQKPGQSPKLLI<br>YWASTRESGVPDRFTGSGSGTDFTLTISSVKAEDLAVYYCQQYYSYPYTFGGGT<br>KLEIKRTVAAPSVFIFPPSDEQLKSGTASVVCLLNNFYPREAKVQWKVDNALQSGNS<br>QESVTEQDSKDSTYSLSSTLTLSKADYEKHKVYACEVTHQGLSSPVTKSFNRGECAS |
| manti-hASGPR_5H8.1D4H-LV-hIgG4H-C-hMOG<br>(LV-hIgG4H-C underlined, variable region bold underline;<br>hMOG in bold)<br>(SEQ ID NO: 29)<br>ATGGCTTGGGTGTGGACCTTGCTATTCCTGATGGCAGCCGCCCAAAGTATCCAAG<br>CACAGATCCAGTTGGTGCAGTCTGGACCTGAGCTGAAGAAGCCTGGAGAGACAG<br>TCAAGATCTCCTGCAAGGCTTCTGGTTATACCTTCACAGACTATTCAGTGCACTG<br>GGTGAAGCAGGCTCCAGGAAAGGGTTTAAAGTGGATGGGCTGGATAAATACTGA<br>GACTGGTGAGCCAACATATGCAGATGACCTCAAGGGACGGTTTGCCTTCTCTTTG<br>GAAACCTCTGCCAGCACTGCCTATTTGCAGATCAACAACCTCAAAAATGAGGAC<br>ACGGCTACATATTTCTGTGCTAAACCTACCTATAGATTTTTTGACTACTGGGGCCA<br>AGGCACCACTCTCACAGCCTCCTCAGCCAAAACGAAGGGCCCATCCGTCTTCCCC<br>CTGGCGCCCTGCTCCAGGAGCACCTCCGAGAGCACAGCCGCCCTGGGCTGCCTG<br>GTCAAGGACTACTTCCCCGAACCGGTGACGGTGTCGTGGAACTCAGGCGCCCTG<br>ACCAGCGGCGTGCACACCTTCCCGGCTGTCCTACAGTCCTCAGGACTCTACTCCC<br>TCAGCAGCGTGGTGACCGTGCCCTCCAGCAGCTTGGGCACGAAGACCTACACCT<br>GCAACGTAGATCACAAGCCCAGCAACACCAAGGTGGACAAGAGAGTTGAGTCCA<br>AATATGGTCCCCCATGCCCACCCTGCCCAGCACCTGAGTTCGAAGGGGGACCATC<br>AGTCTTCCTGTTCCCCCCAAAACCCAAGGACACTCTCATGATCTCCCGGACCCCT<br>GAGGTCACGTGCGTGGTGGTGGACGTGAGCCAGGAAGACCCCGAGGTCCAGTTC<br>AACTGGTACGTGGATGGCGTGGAGGTGCATAATGCCAAGACAAAGCCGCGGGAG<br>GAGCAGTTCAACAGCACGTACCGTGTGGTCAGCGTCCTCACCGTCCTGCACCAGG<br>ACTGGCTGAACGGCAAGGAGTACAAGTGCAAGGTCTCCAACAAAGGCCTCCCGT<br>CCTCCATCGAGAAAACCATCTCCAAAGCCAAAGGGCAGCCCCGAGAGCCACAGG<br>TGTACACCCTGCCCCCATCCCAGGAGGAGATGACCAAGAACCAGGTCAGCCTGA<br>CCTGCCTGGTCAAAGGCTTCTACCCCAGCGACATCGCCGTGGAGTGGGAGAGCA<br>ATGGGCAGCCGGAGAACAACTACAAGACCACGCCTCCCGTGCTGGACTCCGACG<br>GCTCCTTCTTCCTCTACAGCAGGCTAACCGTGGACAAGAGCAGGTGGCAGGAGG<br>GGAATGTCTTCTCATGCTCCGTGATGCATGAGGCTCTGCACAACCACTACACACA<br>GAAGAGCCTCTCCCTGTCTCTGGGTAAAGCTAGTGGTCAGTTTAGAGTCATTGGG<br>CCCAGACACCCTATAAGGGCTCTTGTGGGAGACGAGGTCGAGCTGCCGTGTCGC<br>ATTAGTCCAGGCAAAAACGCCACAGGGATGGAAGTGGGGTGGTACAGGCCTCCC<br>TTCTCTAGGGTTGTGCATCTCTACCGCAACGGCAAAGATCAGGATGGAGATCAAG<br>CTCCTGAATATCGGGGCCGGACTGAGCTGCTCAAGGACGCGATCGGCGAGGGTA<br>AGGTGACCTTGCGCATCCGAAATGTTAGATTCAGCGATGAAGGCGGATTTACGTG |

```
                    Anti-DC ASGPR mAbs

CTTCTTTCGGGACCACTCATACCAGGAGGAAGCCGCAATGGAACTGAAGGTGGA

GGACCCCTTCTATTGGGTATCCCCAGCTAGCTGA (SEQ ID NO: 30)
AQIQLVQSGPELICKPGETVKISCKASGYTFTDYSVHWVKQAPGKGLKWMGWIN

TETGEPTYADDLKGRFAFSLETSASTAYLQINNLKNEDTATYFCAKPTYRFFDY

WGQGTTLTASSAKTKGPSVFPLAPCSRSTSESTAALGCLVKDYFPEPVTVSWNSGA

LTSGVHTFPAVLQSSGLYSLSSVVTVPSSSLGTKTYTCNVDHKPSNTKVDKRVESKY

GPPCPPCPAPEFEGGPSVFLFPPKPKDTLMISRTPEVTCVVVDVSQEDPEVQFNWYVD

GVEVHNAKTKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLSLSLGKASG

QFRVIGPRHPIRALVGDEVELPCRISPGKNATGMEVGWYRPPFSRVVHLYRNGK

DQDGDQAPEYRGRTELLKDAIGEGKVTLRIRNVRFSDEGGFTCFFRDHSYQEEA

AMELKVEDPFYWVSPAS manti-hASGPR_5H8.1D4K-LV-hIgGK-C
(LV-hIgGK-C underlined, variable region bold underline)
                                               (SEQ ID NO: 31)
ATGGATTCACAGGCCCAGGTTCTTATATTGCTGCTGCTATGGGTATCTGGTTCCTG

TGGGGACATTGTGATGTCACAGTCTCCATCCTCCCTGGCTGTGTCAGCAGGAGAG

AAGGTCACTATGAGCTGCAAATCCAGTCAGAGTCTGCTCAACAGTAGAACCCGA

AAGAACTACTTGGCTTGGTACCAGCAGAAACCAGGGCAGTCTCCTAAACTGCTG

ATCTACTGGGCATCCACTAGGGAATCTGGGGTCCCTGATCGCTTCACAGGCAGTG

GATCTGGGACAGATTTCACTCTCACCATCAGCAGTGTGCAGGCTGAGGACCTGGC

AGTTTATTACTGCAAGCAATCTTATAATCTGTGGACGTTCGGTGGAGGCACCAAG

CTCGAGATCAAACGAACTGTGGCTGCACCATCTGTCTTCATCTTCCCGCCATCTG

ATGAGCAGTTGAAATCTGGAACTGCCTCTGTTGTGTGCCTGCTGAATAACTTCTA

TCCCAGAGAGGCCAAAGTACAGTGGAAGGTGGATAACGCCCTCCAATCGGGTAA

CTCCAGGAGAGTGTCACAGAGCAGGACAGCAAGGACAGCACCTACAGCCTCAG

CAGCACCCTGACGCTGAGCAAAGCAGACTACGAGAAACACAAAGTCTATGCCTG

CGAAGTCACCCATCAGGGCCTGAGCTCGCCCGTCACAAAGAGCTTCAACAGGGG

AGAGTGTGCTAGCTGA (SEQ ID NO: 32)
DIVMSQSPSSLAVSAGEKVTMSCKSSQSLLNSRTRICNYLAWYQQKPGQSPKLLI

YWASTRESGVPDRFTGSGSGTDFTLTISSVQAEDLAVYYCKQSYNLWTFGGGTK

LEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGECAS
```

Modular Domain Description of DC-Targeting Multiple Sclerosis Immunotherapeutics In certain aspects a DC-targeting multiple sclerosis immunotherapeutic may be assembled by combining polypeptides domains belonging to various classes of proteins categorized according to a specific function. In a general sense these domains may belong to classes comprising antibodies, antibody CDRs, antibody heavy chains, antibody light chains, linkers, antigens, coupling domains, adjuvants, purification tags, labelling tags or reporter tags.

Non limiting examples of domain categories and specific examples within each category are illustrated in Table 1. (Flgln is abbreviation for Flagellin)

| Peptide Linkers | SEQ ID NO | Antigens | SEQ ID NO | Coupling Domains | SEQ ID NO |
|---|---|---|---|---|---|
| Flex-v1 | 33 | hMBP | 36 | Cohesin | 38 |
| Flexx-v1 | 34 | hMOG | 37 | Dockerin | 39 |
| Flexx-v2 | 35 | | | Dockerinv2 | 40 |

| Adjuvants | SEQ ID NO | Antibodies | | | SEQ ID NO |
|---|---|---|---|---|---|
| hIL-10 | 41 | mAnti-ASGPR_49C11_7H (heavy chain) | | | 42 |
| | | mAnti-ASGPR_49C11_7K (light chain) | | | 43 |
| | | manti-hASGPR_6.3H9.1D11H (heavy chain) | | | 44 |
| | | manti-hASGPR_6.3H9.1D11K (light chain) | | | 45 |
| | | manti-hASGPR_5H8.1D4H (heavy chain) | | | 46 |
| | | manti-hASGPR_5H8.1D4K (light chain) | | | 47 |
| | | mAnti-ASGPR_4G2.2_(heavy chain) | | | 48 |
| | | mAnti-ASGPR_4G2.2_(light chain) | | | 49 |
| | | mAnti-ASGPR_5F10H(heavy chain) | | | 50 |
| | | mAnti-ASGPR_5F10H(light chain) | | | 51 |
| | | mAnti-ASGPR1H11(heavy chain) | | | 52 |
| | | mAnti-ASGPR1H11(light chain) | | | 53 |

In some embodiments, components of a DC-targeting immunotherapeutic may be constructed as illustrated below (For the schematic representations that follow, the following abbreviations apply: Peptide Linker (PL); Antigen (Ag); Tag (Tg); Coupling Domain (CD); Adjuvant (Adj); Antibody (Ab). A number following an abbreviation differentiates between different types of that domain within a construct. A hyphen ("-") used may represent a covalent bond, such as a peptide bond between two domains of a polypeptide that is formed during translation of, for example, a fusion protein. The covalent bond may also be formed by, but is not limited to, known chemical coupling means. A hyphen may also represent a high-affinity, intermediate affinity, or low affinity non-covalent interaction. Examples of these types of non-covalent interactions are known to those skilled in the art and include, but are not limited to, antibody/antigen interaction, receptor/ligand interaction, avidin/biotin interaction, cohesin/dockerin interaction and barnase/barstar interaction):

CD-Ag-Tg;
Ab-Ag-Tg;
Ab-CD-Ag-Tg;
Ab-PL-Ag;
Ab-PL-Ag-Tg;
Ab-PL-Ag(1)-Ag(2)-Tg;
Ab-CD-PL;
Ab-Ag;
Tg-CD-Ag;
Tg-CD-Ag-Tg;
Ab-Adj;
Ab-Adj-Adj;
Tg-CD-Adj;
Tg-CD-Adj(1)-Adj(2);
CD-Adj;
Ab-PL-Ag-PL-Ag;

PL includes but is not limited to peptide linkers. Linkers with non-peptide bonds are also contemplated. In some embodiments the tag is absent from the construct or has been removed.

In one particular embodiment, an antibody-antigen fusion protein (Ab.Ag) comprises the following formula:

Ab-(PL-Ag)x;
Ab-(Ag-PL)x;
Ab-(PL-Ag-PL)x;
Ab-(Ag-PL-Ag)x;
Ab-(PL-Ag)x-PL; or
Ab-(Ag-PL)x-Ag;

wherein Ab is an DC targeting antibody or a fragment thereof; wherein PL is a peptide linker; wherein Ag is an myelin sheath protein or component; and, wherein x is an integer from 1 to 20, or any range derivable therein. PL includes but is not limited to peptide linkers. Linkers with non-peptide bonds are also contemplated.

In one embodiment, the -(PL-Ag)x, -(Ag-PL)x, -(PL-Ag-PL)x, or -(Ag-PL-Ag)x are located at the carboxy terminus of the Ab heavy chain or fragment thereof.

In another embodiment, the -(PL-Ag)x, -(Ag-PL)x, -(PL-Ag-PL)x, or -(Ag-PL-Ag)x are located at the carboxy terminus of the Ab light chain or fragment thereof.

In one embodiment, the antibody-antigen complex (Ab:Ag) comprises the following formula Ab.Doc:Coh.Ag;
Ab.Coh:Doc.Ag;
Ab.(Coh)x: (Doc.Ag)x;
Ab.(Doc)x: (Coh.Ag)x;
Ab.(Coh.Doc)x:(Doc.Ag$^1$)(Coh.Ag$^2$); or
Ab.(Coh)x(Doc)x: (Doc.Ag$^1$)x(Coh.Ag$^2$)x;

wherein Ab is a DC targeting antibody or a fragment thereof; wherein Ag is an myelin sheath protein or component (Ag$^1$ and Ag$^2$ being two distinct myelin sheath protein or components); wherein Doc is dockerin; wherein Coh is cohesin and wherein x is an integer from 1 to 10, or any range derivable therein, denoting the number of molecules or domains in the parentheses immediately preceding it. A period (".") is used to denote a covalent bond between two molecules or domains (examples of these covalent bonds include, but are not limited to, a peptide bond between two domains of a polypeptide that is formed during translation of, for example, a fusion protein. The covalent bond may also be formed by, but is not limited to, known chemical coupling means). A colon (":") is used to denote a non-covalent interaction between a cohesin and dockerin domain.

IV. Methods of Treatment

As discussed above, the compositions and methods of using these compositions can treat a subject (e.g., prevent multiple sclerosis or evoke a robust immune tolerance to a multiple sclerosis autoimmune bout) having, suspected of having, or at risk of developing an autoimmune disorder or related disease, particularly those related to multiple sclerosis.

As used herein the phrase "immune response" or its equivalent "immunological response" refers to a humoral (antibody mediated), cellular (mediated by antigen-specific T cells or their secretion products) or both humoral and cellular response directed against a protein, peptide, or polypeptide of the embodiments in a recipient patient. Treatment or therapy can be an active immune response induced by administration of immunogen or a passive therapy effected by administration of antibody, antibody containing material, or primed T-cells.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include those methods described in Epitope Mapping Protocols (1996). T cells recognize continuous epitopes of about nine amino acids for CD8 cells or about 13-15 amino acids for CD4 cells. T cells that recognize the epitope can be identified by in vitro assays that measure antigen-dependent proliferation, as determined by 3H-thymidine incorporation by primed T cells in response to an epitope (Burke et al., 1994), by antigen-dependent killing (cytotoxic T lymphocyte assay, Tigges et al., 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject. As used herein and in the claims, the terms "antibody" or "immunoglobulin" are used interchangeably.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

In one embodiment a method includes treatment for a disease or condition caused by an autoimmune disorder. In certain aspects embodiments include methods of treatment of multiple sclerosis. In some embodiments, the treatment is administered in the presence of myelin sheath protein or components. Furthermore, in some examples, treatment comprises administration of other agents commonly used against autoimmune disorders, such as one or more immunosuppressant compounds.

The therapeutic compositions are administered in a manner compatible with the dosage formulation, and in such amount as will be therapeutically effective. The quantity to be administered depends on the subject to be treated. Precise amounts of active ingredient required to be administered depend on the judgment of the practitioner. Suitable regimes for initial administration and boosters are also variable, but are typified by an initial administration followed by subsequent administrations.

Compositions of the current methods may be administered to patients via any route used to introduce vaccines or antibodies to patients. Such routes include, but are not limited to, mucosal or intramuscular delivery. In particular embodiments, a composition is administered to a patient intranasally or by inhalation. In other embodiments, a composition is administered intravenously or by intravenous injection. In additional embodiments, the administration of compositions includes, but is not limited to oral, parenteral, subcutaneous, intramuscular, intravenous administration, or various combinations thereof.

The manner of application may be varied widely. Any of the conventional methods for administration of a polypeptide therapeutic are applicable. These are believed to include oral application on a solid physiologically acceptable base or in a physiologically acceptable dispersion, parenterally, by injection and the like. The dosage of the composition will depend on the route of administration and will vary according to the size and health of the subject. In one treatment scheme, the patient receives a subcutaneous dose of the immunotherapeutic every week for three weeks and then every first week for an additional 1, 2, 3, 4, 5, 6, 7, 8, 9, 10, 11, or 12 months.

In certain instances, it will be desirable to have multiple administrations of the composition, e.g., 2, 3, 4, 5, 6 or more administrations. The administrations can be at 1, 2, 3, 4, 5, 6, 7, 8, to 5, 6, 7, 8, 9, 10, 11, 12 twelve week intervals, including all ranges there between.

Combination Therapy

The compositions and related methods, particularly administration of an antibody that binds DC receptor and delivers a myelin sheath protein or component or a peptide to a patient/subject, may also be used in combination with the administration of multiple sclerosis effective strategies or traditional immunomodulatory therapies. Such strategies or therapies may be directed, among other aims, to modify the disease course, treat exacerbations, manage symptoms or improve a compromised function. Examples of disease-modifying agents include, but are not limited to, Aubagio (teriflunomide), Avonex (interferon beta-1a), Betaseron and Extavia (interferon beta-1b), Copaxone (glatiramer acetate), Extavia (interferon beta-1b), Gilenya (fingolimod), Novantrone (mitoxantrone), Rebif (interferon beta-1a), Tecfidera (dimethyl fumarate), and Tysabri (natalizumab). In other embodiments the disease-modifying therapeutic to be used in combination therapy include, but are not limited to, Fingolimod (Gilenya), Methotrexate, azathioprine (Imuran), intravenous immunoglobulin (IVIg) and cyclophosphamide (Cytoxan).

In some instances the combination therapeutic may be used to control symptoms. Examples of medications or pharmaceuticals that may be used to control multiple sclerosis symptoms include, but are not limited to, dalfamipridine (Ampyra), tizanidine (Zanaflex), diazepam (Valium), clonazepam (Klonopin), dantrolene (Dantrium), baclofen (Lioresal), or any benzodiazepine, cholinergic medications, or amantadine.

In one aspect, it is contemplated that a therapy is used in conjunction with immunosuppressants. In other aspects, a therapy is used in conjunction with disease-modifying agents, symptom controlling agents, or agents to improve compromised function. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the therapeutic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Various combinations of therapy may be employed, for example immunosuppressant therapy, disease-modifying agents, symptom controlling agents, or agents to improve compromised function is "A" and an antibody immunotherapeutic that comprises an antibody that binds a DC receptor and delivers an myelin sheath protein or component or a peptide or consensus peptide thereof is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

Administration of the antibody compositions to a patient/subject will follow general protocols for the administration of such compounds, taking into account the toxicity, if any, of the composition. It is expected that the treatment cycles would be repeated as necessary. It is also contemplated that various standard therapies, such as hydration, may be applied in combination with the described therapy.

General Pharmaceutical Compositions

In some embodiments, pharmaceutical compositions are administered to a subject. Different aspects may involve administering an effective amount of a composition to a subject. In some embodiments, an antibody that binds DC receptor and delivers a myelin sheath protein or component or a peptide or consensus peptide thereof may be administered to the patient to protect against or treat against multiple sclerosis. Alternatively, an expression vector encoding one or more such antibodies or polypeptides or peptides may be given to a patient as a preventative treatment. Additionally, such compositions can be administered in combination with an immunosuppressant. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-infective agents, immunosuppressants and immunotherapeutics, can also be incorporated into the compositions.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization or an equivalent procedure. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a immunotherapeutic composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

IV. EXAMPLES

The following examples are included to demonstrate preferred embodiments. It should be appreciated by those of skill in the art that the techniques disclosed in the examples which follow represent techniques discovered by the inventors to function well in the practice of the embodiments, and thus can be considered to constitute preferred modes for their practice. However, those of skill in the art should, in light of the present disclosure, appreciate that many changes can be made in the specific embodiments which are disclosed and still obtain a like or similar result without departing from the spirit and scope of the invention.

Example 1—Characterization and Response to Anti-DC-ASGPR Antibodies

All animals (total 12 animals: 6 animals per group) were pre-immunized with live influenza viruses (H1N1, PR8). Sera from all animals displayed HA1-specific IgG (data not shown). Four months after priming, animals were immunized i.d. with either anti-LOX-1-HA1 (right arm) and anti-LOX-1-PSA (left arm) or anti-DC-ASGPR-HA1 (right arm) and anti-DC-ASGPR-PSA (left arm). After three immunizations at 40 days intervals with the same recombinant fusion proteins, blood was collected as indicated. PBMCs from animals immunized with anti-DC-ASGPR-HA1 secreted higher levels of IL-10 in response to HA1 peptide pool when compared to those immunized with anti-LOX-1-HA1 (FIG. 2B, upper panel). Conversely, PBMCs from animals immunized with anti-LOX-1-HA1 secreted significantly higher levels of IFNγ than animals immunized with anti-DC-ASGPR-HA1 (FIG. 2B, lower panel). The same findings were made with animals that were primed and boosted twice with PSA fusion proteins. PSA-specific IL-10-producing cellular responses were preferentially mounted in animals immunized with anti-DC-ASGPR-PSA (FIG. 1B, upper panel). Animals immunized with anti-LOX-1-PSA mounted higher PSA-specific IFNγ-producing cellular responses than animals immunized with anti-DC-ASGPR-PSA (FIG. 1B, lower panel). For both HA1 and PSA, the peak of IL-10-producing cellular responses was obtained at week one, but the peak of IFNγ-producing cellular responses was obtained at week three. Taken together, the data show that targeting antigens to in vivo DCs via DC-ASGPR can establish antigen-specific IL-10-producing T cells in vivo.

Monocyte-derived IFNDCs were cultured overnight in the plates coated with indicated monoclonal antibodies. Cells were harvested and RNA expression levels of IL-10, IL-6 and TNFalpha was assessed by real time PCR using commercially available PCR primers. Compared to other clones of anti-DC-ASGPR antibodies, 5H8 and 49C11 resulted in increased expression of IL-10. They also induced increased levels of IL-6 and TNFa (FIG. 3A).

The amount of IL-10 in the culture supernatants were assessed by Luminex assay. Consistent with the data in the left panel, 5H8 and 49C11 induced IFNDCs to secrete increased amount of IL-10 (FIG. 3B).

CD11c+ blood DCs from healthy donors (n=6) and MS patients (n=25) were stained with 5H8, 4G2 and 49C11. CD11c+ DCs from both healthy and patient donors displayed two distinct patterns of anti-DC-ASGPR antibody bindings: all of the anti-DC-ASGPR antibodies bound well to CD11c+ DCs from approximately 50% of the donors, while CD11c+ DCs from the other 50% of donors were weakly stained with the three clones of anti-DC-ASGPR antibodies. However, 49C11 was able to bind to CD11c+ DCs better than the other two clones. In addition to its (49C11) ability to induce IL-10, 49C11 can bind well to DCs. Thus 49C11 was selected as a clone to be fused to MS antigens (FIG. 4).

Figure 6:
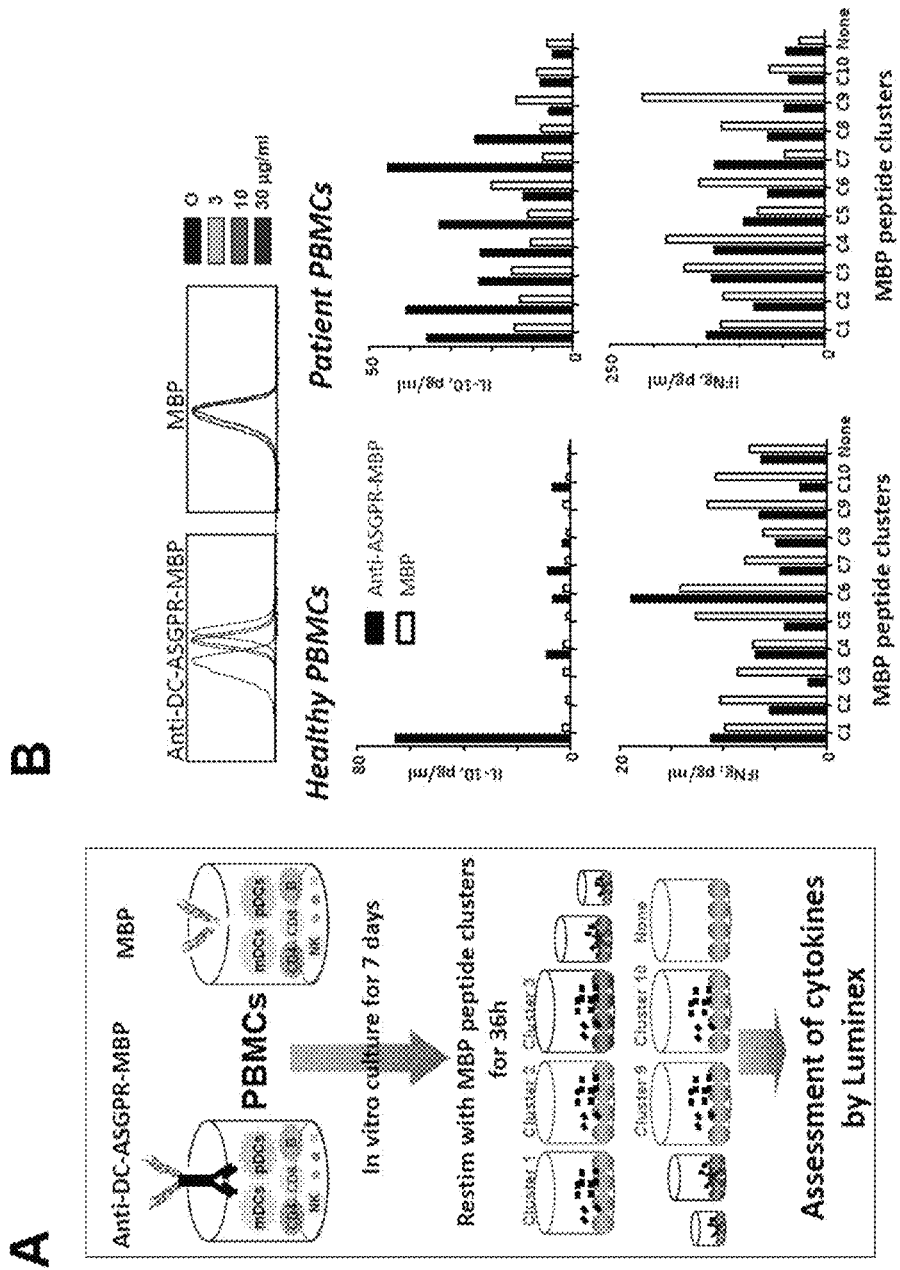

CD11c+ DCs from healthy donors were stained with different concentrations (0, 3, 10, and 30 ug/ml) of anti-DC-ASGPR-MBP or MBP alone. The data indicate that anti-DC-ASGPR-MBP binds well to the DCs (FIG. 6B, upper panels).

PBMCs from healthy and MS patient donors were loaded with 5 ug/ml anti-DC-ASGPR-MBP fusion protein or MBP alone. Cells were incubated for 7 days and then T cells were restimulated for 48 h in the presence of MBP-derived peptide clusters. IFNg and IL-10 secreted from T cells were assessed by the Luminex. Compared to MBP, anti-DC-ASGPR-MBP resulted in increased MBP-specific IL-10 producing T cell responses in both healthy and patient donors (FIG. 6B, lower panels).

Figure 7:
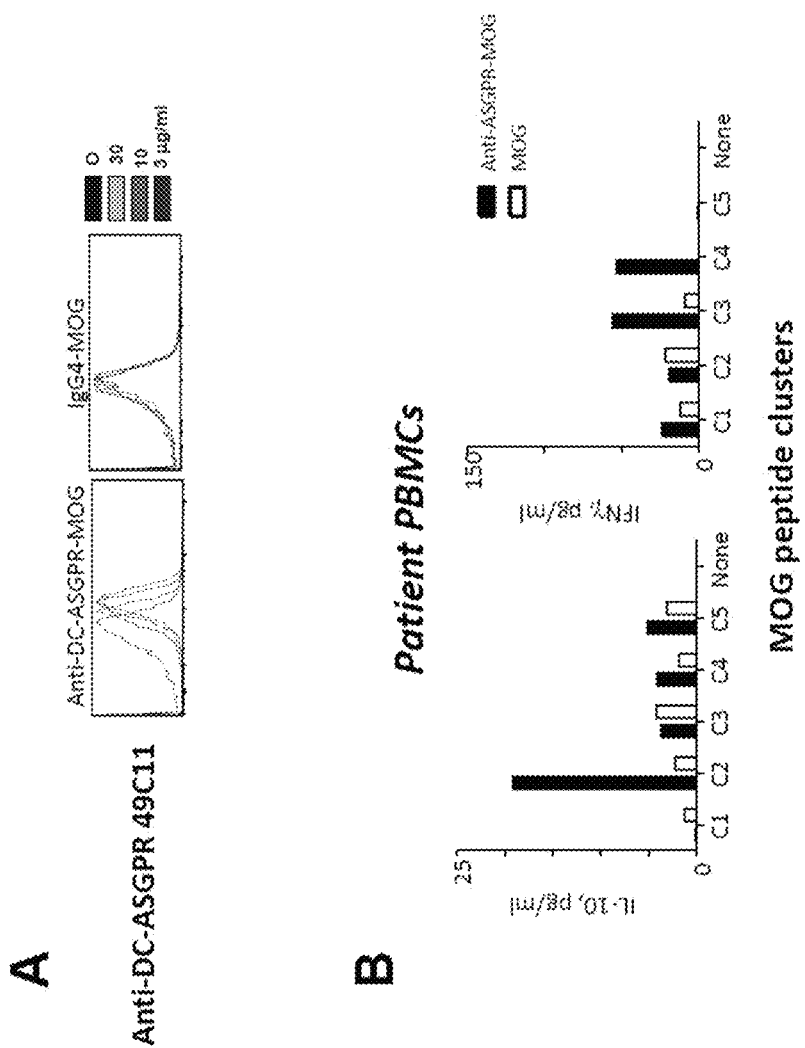

CD11c+ DCs from healthy donors were stained with different concentrations (0, 3, 10, and 30 ug/ml) of anti-DC-ASGPR-MOG or MOG alone. The data indicate that anti-DC-ASGPR-MOG binds well to the DCs (FIG. 7A).

(Lower panels) PBMCs from MS patient donor were loaded with 5 ug/ml anti-DC-ASGPR-MOG fusion protein or MBP alone. Cells were incubated for 7 days and then T cells were restimulated for 48 h in the presence of MBP-derived peptide clusters. IFNg and IL-10 secreted from T cells were assessed by the Luminex Compared to MOG, anti-DC-ASGPR-MOG resulted in increased MBP-specific IL-10 producing T cell responses in both healthy and patient donors (FIG. 7B).

Example 2—Effect of Anti-DC-ASGPR-MOG on EAE Induction/Progression in NHP

The following experimental results were kindly provided by Dr. Roger Le Grand, who worked with the inventors.

To test the effects of anti-DC-ASGPR-MOG on the development/progression of EAE in non-human primates (NHP), an EAE model in cynomolgus macaques was used.

Experimental autoimmune encephalomyelitis (EAE), sometimes referred to as experimental allergic encephalomyelitis, is an animal model of brain inflammation. It is an inflammatory demyelinating disease of the central nervous system (CNS). Originally used with rodents, it is widely studied as an animal model of human CNS demyelinating diseases, including multiple sclerosis and acute disseminated encephalomyelitis (ADEM). EAE is also the prototype for T-cell-mediated autoimmune disease in general. Animals are scored according to the following clinical signs and duration of symptoms:

| EAE score | Clinical signs | Maximal cumulative duration |
|---|---|---|
| 0 | Asymptomatic | End of the study |
| 1 | Discrete behavioral disorder with stereotypia, ptosis, nystagmus, discrete paresis, rubbing. | 20 weeks |
| 2 | Moderate behavioral disorders (shaking, oculomotor paralysis, paresis with compensation). | 4 weeks |
| 3 | Walking disorders (ataxia, lameness) without social or feeding behavior impact. | 2 weeks |
| 4 | Severe behavioral disorders (paralysis, paresis) leading to lack of self feeding. | <18 h |
| 5 | Coma. | <6 h |
| 6 | Moribund. | <1 h |

Figure 8:
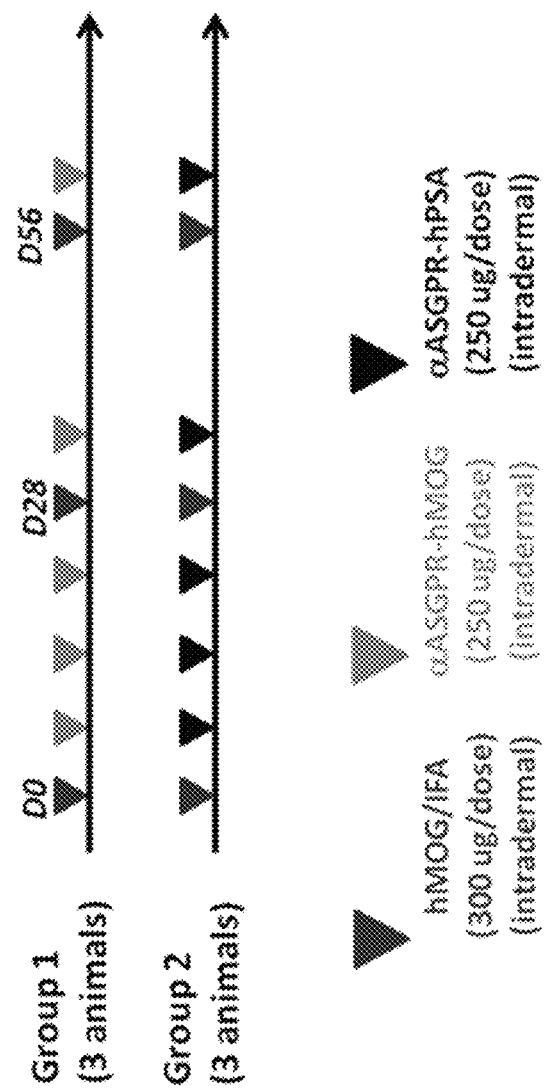

Experimental Design. The Experimental Design is summarized in FIG. 8. Group 1 (Experimental group: consisting of 3 cynomolgus macaques) and Group 2 (Control group: consisting of 3 cynomolgus macaques) were injected with hMOG in incomplete Freund's adjuvant on days 0, 28 and 56. Experimental Group 1 animals received anti-ASGPR-hMOG injections on days 7, 14, 21, 35, and 63. Control group 2 animals received anti-ASGPR-hPSA injections on days 7, 14, 21, 35, and 63.

Figure 9:
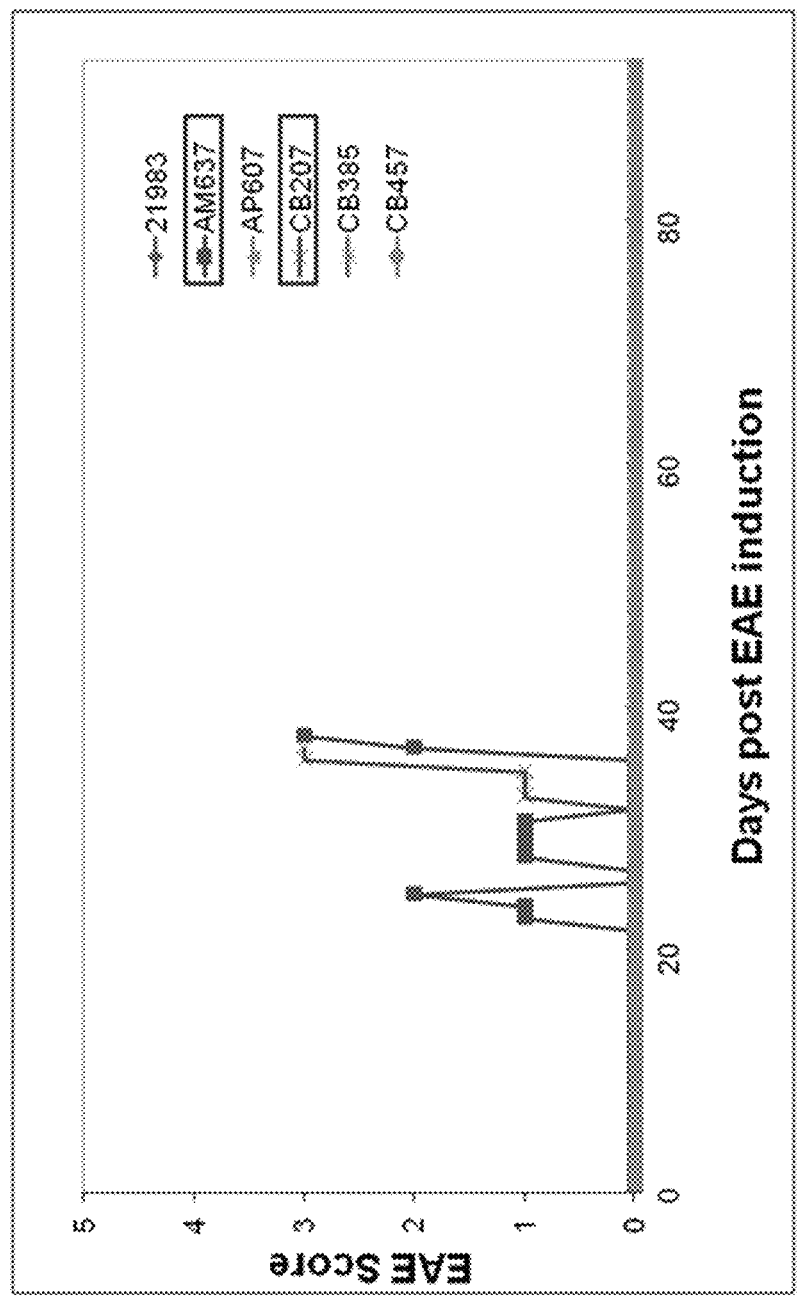
Figure 10:
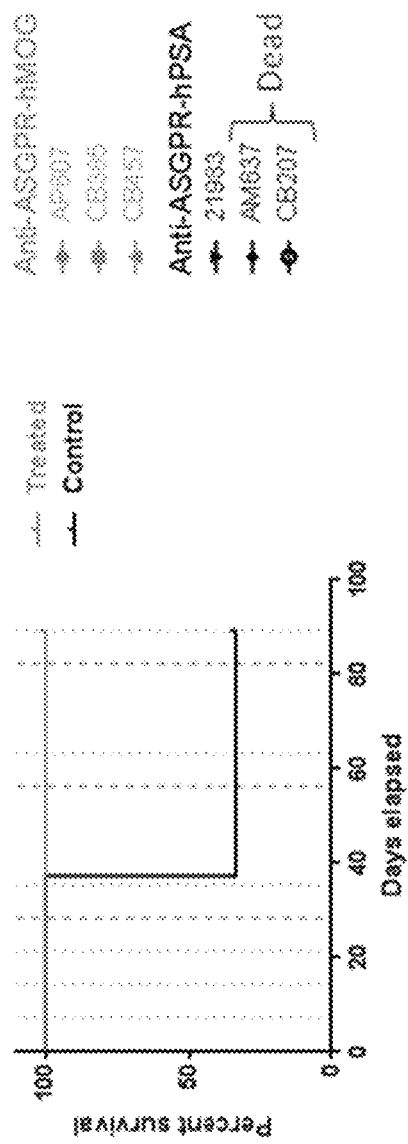

Anti-DC-ASGPR-MOG suppresses the development/progression of EAE in NHP. During the entire period of the experiment, animals were monitored daily to measure EAE score. None of the animals (ID numbers AP607, CB385, and CB457) treated with anti-DC-ASGPR-MOG showed any clinical signs of disease. These animals did not show escalated EAE disease scores. However, two (AM637 and CB207) out of three animals (AM637, CB207, and 21983) in the control group displayed escalated EAE scores between days 20 and 37 (when both animals died; FIGS. 9 and 10). Taken together, the inventors conclude that anti-DC-ASGPR-MOG is able to suppress the development/progression of EAE in NHP.

Figure 11:
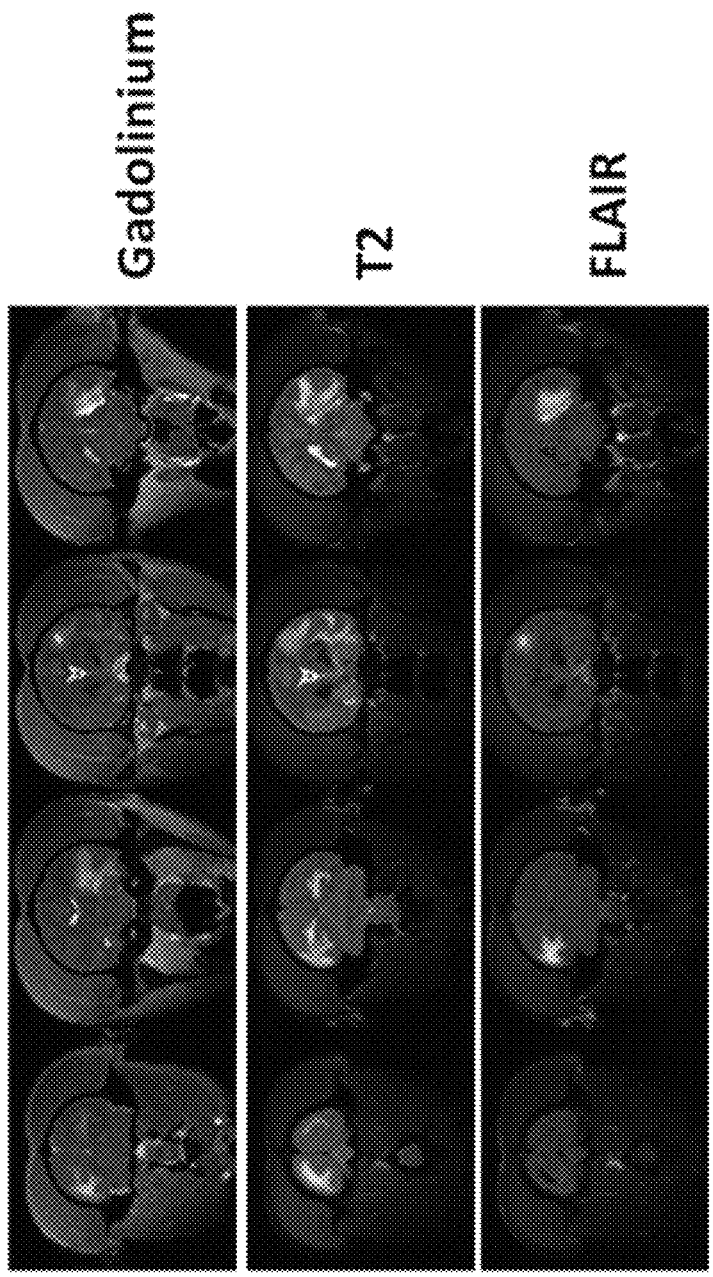

To further confirm whether the clinical signs observed (FIGS. 9 and 10) in the animals in the control group (Group 2 in FIG. 8) were due to inflammation in the brain, magnetic resonance imaging (MRI) of the brain of animal AM637 on day 22 was performed. FIG. 11 shows that i.v. administered gadolinium is dispersed, indicating that there was leakage in the blood vessels into the brain. A T2 image also shows the accumulation of water in several spots, indicating that myelin in this animal was damaged and thus less able to exclude water. Considering Flair data along with T2 and gadolinium data, it was concluded that this animal had severe inflammation in the brain, along with demyelination, which is a typical sign of EAE.

In summary, the inventors demonstrated that 1) cynomolgus macaques develop EAE by immunizing with MOG peptide and an adjuvant and 2) anti-DC-ASGPR-MOG, but not anti-DC-ASGPR-hPSA, suppressed the development/progression of EAE in cynomolgus macaques.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of inducing immune tolerance to myelin oligodendrocyte glycoprotein (MOG) in a patient comprising administering to the patient an effective amount of a composition comprising an anti-DC-ASGPR antibody attached to an antigenic fragment of MOG; and wherein the antigenic fragment of MOG consists of SEQ ID NO:37.

2. The method of claim 1, wherein the anti-DC-ASGPR antibody is further attached to a tolerogenic adjuvant.

3. The method of claim 2, wherein the tolerogenic adjuvant is IL-10, dexamethasone, FK506 (tacrolimus), cholera toxin B subunit, *Escherichia coli* heat-labile enterotoxin B subunit, IFN-beta, a glucocorticoid, vitamin D3, or a TLR agonist.

4. The method of claim 3, wherein the tolerogenic adjuvant is IL-10.

5. The method of claim 3, wherein the tolerogenic adjuvant is a TLR agonist.

6. The method of claim 1, wherein the patient has multiple sclerosis, neuropathy, central pontine myelinolysis, tabes dorsalis, transverse myelitis, Devic's disease, progressive multifocal leukoencephalopathy, optic neuritis, or leukodystrophy.

7. The method of claim 6, wherein the patient has multiple sclerosis.

8. A method for treating a demyelinating disease in a subject comprising administering to the subject a pharmaceutically acceptable vaccine composition comprising at least a first anti-DC-ASGPR antibody attached to an antigenic fragment of myelin oligodendrocyte glycoprotein (MOG), and wherein the antigenic fragment of MOG consists of SEQ ID NO:37.

9. The method of claim 8, the anti-DC-ASGPR antibody is further attached to a tolerogenic adjuvant.

10. The method of claim 9, wherein the tolerogenic adjuvant is IL-10, dexamethasone, FK506 (tacrolimus), cholera toxin B subunit, *Escherichia coli* heat-labile enterotoxin B subunit, IFN-beta, a glucocorticoid, vitamin D3, or a TLR agonist.

11. The method of claim 10, wherein the tolerogenic adjuvant is IL-10.

12. The method of claim 10, wherein the tolerogenic adjuvant is a TLR agonist.

13. The method of claim 8, wherein the demyelinating disease is multiple sclerosis, neuropathy, central pontine myelinolysis, tabes dorsalis, transverse myelitis, Devic's disease, progressive multifocal leukoencephalopathy, optic neuritis, or leukodystrophy.

14. The method of claim 13, wherein the demyelinating disease is multiple sclerosis.

15. A composition comprising an anti-DC-ASGPR antibody attached to an antigenic fragment of myelin oligodendrocyte glycoprotein (MOG); wherein the antigenic fragment of MOG consists of SEQ ID NO: 37.

16. The composition of claim 15, further comprising a tolerogenic adjuvant attached to the anti-DC-ASGPR antibody.

17. The composition of claim 16, wherein the tolerogenic adjuvant is IL-10, dexamethasone, FK506 (tacrolimus), cholera toxin B subunit, *Escherichia coli* heat-labile enterotoxin B subunit, IFN-beta, a glucocorticoid, vitamin D3, or a TLR agonist.

18. The composition of claim 17, wherein the tolerogenic adjuvant is IL-10.

19. The composition of claim 17, wherein the tolerogenic adjuvant is a TLR agonist.

\* \* \* \* \*

SEQUENCE LISTING

```
<160> NUMBER OF SEQ ID NOS: 53

<210> SEQ ID NO 1
<211> LENGTH: 25
<212> TYPE: PRT
<213> ORGANISM: Artificial Sequence
<220> FEATURE:
<223> OTHER INFORMATION: Synthetic sequence

<400> SEQUENCE: 1

Ser Ser Val Ser Pro Thr Thr Ser Val His Pro Thr Pro Thr Ser Val
1               5                   10                  15

Pro Pro Thr Pro Thr Lys Ser Ser Pro
            20                  25

<210> SEQ ID NO 2
<211> LENGTH: 25
<212> TYPE: PRT
<213> ORGANISM: Artificial Sequence
<220> FEATURE:
<223> OTHER INFORMATION: Synthetic sequence

<400> SEQUENCE: 2

Ser Ser Val Ser Pro Thr Thr Ser Val His Pro Thr Pro Thr Ser Val
1               5                   10                  15
```

```
Pro Pro Thr Pro Thr Lys Ser Ser Pro
            20              25

<210> SEQ ID NO 3
<211> LENGTH: 25
<212> TYPE: PRT
<213> ORGANISM: Artificial Sequence
<220> FEATURE:
<223> OTHER INFORMATION: Synthetic sequence

<400> SEQUENCE: 3

Thr Val Thr Pro Thr Ala Thr Ala Thr Pro Ser Ala Ile Val Thr Thr
1               5                   10                  15

Ile Thr Pro Thr Ala Thr Thr Lys Pro
            20              25

<210> SEQ ID NO 4
<211> LENGTH: 25
<212> TYPE: PRT
<213> ORGANISM: Artificial Sequence
<220> FEATURE:
<223> OTHER INFORMATION: Synthetic sequence

<400> SEQUENCE: 4

Thr Asn Gly Ser Ile Thr Val Ala Ala Thr Ala Pro Thr Val Thr Pro
1               5                   10                  15

Thr Val Asn Ala Thr Pro Ser Ala Ala
            20              25

<210> SEQ ID NO 5
<211> LENGTH: 446
<212> TYPE: PRT
<213> ORGANISM: Artificial Sequence
<220> FEATURE:
<223> OTHER INFORMATION: Synthetic sequence

<400> SEQUENCE: 5

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile Leu Phe Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Phe Cys
                85                  90                  95

Ala Arg Ser Asn Tyr Gly Ser Phe Ala Ser Trp Gly Gln Gly Thr Leu
            100                 105                 110

Val Thr Val Ser Ala Ala Lys Thr Thr Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

Ser Gly Leu Tyr Ser Leu Ser Ser Val Val Thr Val Pro Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Ala Ser
            435                 440                 445

<210> SEQ ID NO 6
<211> LENGTH: 213
<212> TYPE: PRT
<213> ORGANISM: Artificial Sequence
<220> FEATURE:
<223> OTHER INFORMATION: Synthetic sequence

<400> SEQUENCE: 6

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser His Met
            20                  25                  30

His Trp Tyr Gln Gln Lys Ser Gly Thr Ser Pro Lys Arg Trp Ile Tyr
            35                  40                  45

Asp Thr Ser Arg Leu Ala Ser Gly Val Pro Ala Arg Phe Ser Gly Ser
50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser His Pro Trp Ser
            85                  90                  95

```
Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
210

<210> SEQ ID NO 7
<211> LENGTH: 449
<212> TYPE: PRT
<213> ORGANISM: Artificial Sequence
<220> FEATURE:
<223> OTHER INFORMATION: Synthetic sequence

<400> SEQUENCE: 7

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Val Pro Gly Lys Gly Leu Arg Trp Met
        35                  40                  45

Gly Trp Met Asp Thr Phe Thr Gly Glu Pro Tyr Ala Asp Asp Phe
50                  55                  60

Lys Gly Arg Phe Ala Phe Ser Leu Glu Thr Ser Ala Ser Thr Ala Tyr
65                  70                  75                  80

Leu Gln Ile Asn Ser Leu Lys Asn Glu Asp Thr Ala Thr Tyr Phe Cys
                85                  90                  95

Ala Arg Gly Gly Ile Leu Arg Leu Asn Tyr Phe Asp Tyr Trp Gly Gln
            100                 105                 110

Gly Thr Thr Leu Thr Val Ser Ser Ala Lys Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Glu Gly Gly Pro Ser Val
225                 230                 235                 240
```

-continued

```
Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Ala
        435                 440                 445

Ser

<210> SEQ ID NO 8
<211> LENGTH: 214
<212> TYPE: PRT
<213> ORGANISM: Artificial Sequence
<220> FEATURE:
<223> OTHER INFORMATION: Synthetic sequence

<400> SEQUENCE: 8

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Gly Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Ala Leu Ser Ile Thr Ser Leu Gln Thr
65                  70                  75                  80

Glu Asp Leu Ala Thr Tyr Tyr Cys Gln Gln Cys Trp Thr Ser Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
                195                 200                 205
Phe Asn Arg Gly Glu Cys
                210

<210> SEQ ID NO 9
<211> LENGTH: 445
<212> TYPE: PRT
<213> ORGANISM: Artificial Sequence
<220> FEATURE:
<223> OTHER INFORMATION: Synthetic sequence

<400> SEQUENCE: 9

Glu Val Gln Leu Gln Gln Ser Gly Pro Glu Leu Val Lys Pro Gly Ala
1               5                   10                  15
Ser Val Lys Met Ser Cys Lys Ala Ser Gly Tyr Thr Phe Thr Asp Tyr
                20                  25                  30
Tyr Met Lys Trp Val Lys Gln Ser His Gly Lys Ser Leu Glu Trp Ile
            35                  40                  45
Gly Asp Ile Asn Pro Asn Tyr Gly Asp Thr Phe Tyr Asn Gln Lys Phe
        50                  55                  60
Glu Gly Lys Ala Thr Leu Thr Val Asp Lys Ser Ser Arg Thr Ala Tyr
65                  70                  75                  80
Met Gln Leu Asn Ser Leu Thr Ser Glu Asp Ser Ala Val Tyr Tyr Cys
                85                  90                  95
Gly Arg Gly Asp Tyr Gly Tyr Phe Asp Val Trp Gly Ala Gly Thr Thr
                100                 105                 110
Val Thr Val Ser Ser Ala Lys Thr Lys Gly Pro Ser Val Phe Pro Leu
            115                 120                 125
Ala Pro Cys Ser Arg Ser Thr Ser Glu Ser Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Lys Thr Tyr Thr Cys Asn Val Asp His Lys Pro Ser Asn
                195                 200                 205
Thr Lys Val Asp Lys Arg Val Glu Ser Lys Tyr Gly Pro Pro Cys Pro
        210                 215                 220
Pro Cys Pro Ala Pro Glu Phe Glu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Gln Glu Asp Pro Glu Val Gln Phe
                260                 265                 270
Asn Trp Tyr Val Asp Gly Val Glu Val His Asn Ala Lys Thr Lys Pro
            275                 280                 285
Arg Glu Glu Gln Phe Asn Ser Thr Tyr Arg Val Val Ser Val Leu Thr
```

```
            290                 295                 300
Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Leu Ser Leu Gly Lys Ala Ser
            435                 440                 445

<210> SEQ ID NO 10
<211> LENGTH: 214
<212> TYPE: PRT
<213> ORGANISM: Artificial Sequence
<220> FEATURE:
<223> OTHER INFORMATION: Synthetic sequence

<400> SEQUENCE: 10

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Phe Thr Leu Thr Ile Asn Asn Val Gln Ser
65                  70                  75                  80

Glu Asp Leu Ala Asp Tyr Phe Cys Gln Gln Tyr Ser Ser Asn Pro Tyr
                85                  90                  95

Met Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
```

<210> SEQ ID NO 11
<211> LENGTH: 447
<212> TYPE: PRT
<213> ORGANISM: Artificial Sequence
<220> FEATURE:
<223> OTHER INFORMATION: Synthetic sequence

<400> SEQUENCE: 11

```
Gln Leu Gln Gln Ser Gly Pro Glu Leu Val Lys Pro Gly Ala Ser Val
1               5                   10                  15

Lys Ile Ser Cys Lys Thr Ser Gly Tyr Thr Phe Thr Glu Tyr Thr Met
            20                  25                  30

His Trp Val Arg Gln Ser His Gly Lys Ser Leu Glu Trp Ile Gly Gly
        35                  40                  45

Ile Asn Pro Ile Asn Gly Gly Pro Thr Tyr Asn Gln Lys Phe Lys Gly
    50                  55                  60

Lys Ala Thr Leu Thr Val Asp Lys Ser Ser Thr Ala Tyr Met Glu
65                  70                  75                  80

Leu Arg Ser Leu Thr Ser Glu Asp Ser Ala Val Tyr Tyr Cys Ala Arg
                85                  90                  95

Trp Asp Tyr Gly Ser Arg Asp Val Met Asp Tyr Trp Gly Gln Gly Thr
            100                 105                 110

Ser Val Thr Val Ser Ser Ala Lys Thr Lys Gly Pro Ser Val Phe Pro
        115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
```

```
                355                 360                 365
Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys Ala Ser
            435                 440                 445

<210> SEQ ID NO 12
<211> LENGTH: 214
<212> TYPE: PRT
<213> ORGANISM: Artificial Sequence
<220> FEATURE:
<223> OTHER INFORMATION: Synthetic sequence

<400> SEQUENCE: 12

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Arg Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Thr Tyr Ser Tyr Ile Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 1992
<212> TYPE: DNA
<213> ORGANISM: Artificial Sequence
<220> FEATURE:
<223> OTHER INFORMATION: Synthetic sequence

<400> SEQUENCE: 13
```

```
atgagagcgc tgattctttt gtgcctgttc acagcctttc ctggtatcct gtctgatgtg      60
cagcttcagg agtcaggacc tgacctggtg aaaccttctc agtcactttc actcacctgc     120
actgtcactg gctactccat caccagtggt tatagctggc actggatccg gcagtttcca     180
ggaaacaaac tggaatggat gggctacata ctcttcagtg gtagcactaa ctacaaccca     240
tctctgaaaa gtcgaatctc tatcactcga gacacatcca agaaccagtt cttcctgcag     300
ttgaattctg tgactactga ggacacagcc acatatttct gtgcaagatc taactatggt     360
tcctttgctt cctggggcca agggactctg gtcactgtct ctgcagccaa acaacgggc     420
ccatccgtct tccccctggc gccctgctcc aggagcacct ccgagagcac agccgccctg     480
ggctgcctgg tcaaggacta cttccccgaa ccggtgacgg tgtcgtggaa ctcaggcgcc     540
ctgaccagcg gcgtgcacac cttcccggct gtcctacagt cctcaggact ctactccctc     600
agcagcgtgg tgaccgtgcc ctccagcagc ttgggcacga gacctacac ctgcaacgta     660
gatcacaagc ccagcaacac caaggtggac aagagagttg agtccaaata tggtccccca     720
tgcccaccct gcccagcacc tgagttcgaa ggggaccat cagtcttcct gttcccccca     780
aaacccaagg acactctcat gatctcccgg acccctgagg tcacgtgcgt ggtggtggac     840
gtgagccagg aagaccccga ggtccagttc aactggtacg tggatggcgt ggaggtgcat     900
aatgccaaga caaagccgcg ggaggagcag ttcaacagca cgtaccgtgt ggtcagcgtc     960
ctcaccgtcc tgcaccagga ctggctgaac ggcaaggagt acaagtgcaa ggtctccaac    1020
aaaggcctcc cgtcctccat cgagaaaacc atctccaaag ccaaagggca gccccgagag    1080
ccacaggtgt acaccctgcc cccatcccag gaggagatga ccaagaacca ggtcagcctg    1140
acctgcctgg tcaaaggctt ctaccccagc gacatcgccg tggagtggga gagcaatggg    1200
cagccggaga caactacaa gaccacgcct cccgtgctgg actccgacgg ctccttcttc    1260
ctctacagca ggctaaccgt ggacaagagc aggtggcagg aggggaatgt cttctcatgc    1320
tccgtgatgc atgaggctct gcacaaccac tacacacaga gagcctctc cctgtctctg    1380
ggtaaagcta gtcagacccc caccaacacc atcagcgtga cccccaccaa caacagcacc    1440
cccaccaaca acagcaaccc caagcccaac ccgctagtg catcacaaaa gcggccttca    1500
caacggcacg gatctaaata tctggcgaca gcctctacca tggatcacgc caggcatggc    1560
tttctgccca ggcacagaga tactggaatc ttggactcca tcggcaggtt ctttggcggc    1620
gaccgagggg ctcccaagag agggagtggc aaggatagcc atcatccagc ccgaacagcc    1680
cactacggaa gcctgccgca gaaaagccac ggtcgcacgc aggatgaaaa tcccgttgtg    1740
cacttcttca aaaacattgt gaccccacga actcctccac cttcccaagg caagggcaga    1800
ggtctcagtc tcagccggtt cagttggggg gccgagggcc agagaccgg atttggttat    1860
gggggaaggg ctagcgacta caagtctgca cataaggggt tcaaaggggt cgacgcacag    1920
ggaaccctgt ccaaaatatt taagcttggt ggccgcgact cccgctcagg ctctcccatg    1980
gctcggcgct ga                                                         1992
```

<210> SEQ ID NO 14
<211> LENGTH: 645
<212> TYPE: PRT
<213> ORGANISM: Artificial Sequence
<220> FEATURE:
<223> OTHER INFORMATION: Synthetic sequence

<400> SEQUENCE: 14

Asp Val Gln Leu Gln Glu Ser Gly Pro Asp Leu Val Lys Pro Ser Gln

-continued

```
  1               5                   10                  15
Ser Leu Ser Leu Thr Cys Thr Val Thr Gly Tyr Ser Ile Thr Ser Gly
                 20                  25                  30

Tyr Ser Trp His Trp Ile Arg Gln Phe Pro Gly Asn Lys Leu Glu Trp
                 35                  40                  45

Met Gly Tyr Ile Leu Phe Ser Gly Ser Thr Asn Tyr Asn Pro Ser Leu
                 50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Phe Cys
                 85                  90                  95

Ala Arg Ser Asn Tyr Gly Ser Phe Ala Ser Trp Gly Gln Gly Thr Leu
                100                 105                 110

Val Thr Val Ser Ala Ala Lys Thr Thr Gly Pro Ser Val Phe Pro Leu
                115                 120                 125

Ala Pro Cys Ser Arg Ser Thr Ser Glu Ser Thr Ala Ala Leu Gly Cys
                130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
                195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Tyr Arg Val Val Ser Val Leu Thr
                290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430
```

```
            Tyr Thr Gln Lys Ser Leu Ser Leu Ser Leu Gly Lys Ala Ser Gln Thr
                435                 440                 445

Pro Thr Asn Thr Ile Ser Val Thr Pro Thr Asn Asn Ser Thr Pro Thr
            450                 455                 460

Asn Asn Ser Asn Pro Lys Pro Asn Pro Ala Ser Ala Ser Gln Lys Arg
            465                 470                 475                 480

Pro Ser Gln Arg His Gly Ser Lys Tyr Leu Ala Thr Ala Ser Thr Met
                            485                 490                 495

Asp His Ala Arg His Gly Phe Leu Pro Arg His Arg Asp Thr Gly Ile
                        500                 505                 510

Leu Asp Ser Ile Gly Arg Phe Gly Gly Asp Arg Gly Ala Pro Lys
                    515                 520                 525

Arg Gly Ser Gly Lys Asp Ser His His Pro Ala Arg Thr Ala His Tyr
            530                 535                 540

Gly Ser Leu Pro Gln Lys Ser His Gly Arg Thr Gln Asp Glu Asn Pro
            545                 550                 555                 560

Val Val His Phe Phe Lys Asn Ile Val Thr Pro Arg Thr Pro Pro Pro
                            565                 570                 575

Ser Gln Gly Lys Gly Arg Gly Leu Ser Leu Ser Arg Phe Ser Trp Gly
                        580                 585                 590

Ala Glu Gly Gln Arg Pro Gly Phe Gly Tyr Gly Gly Arg Ala Ser Asp
                    595                 600                 605

Tyr Lys Ser Ala His Lys Gly Phe Lys Gly Val Asp Ala Gln Gly Thr
            610                 615                 620

Leu Ser Lys Ile Phe Lys Leu Gly Gly Arg Asp Ser Arg Ser Gly Ser
            625                 630                 635                 640

Pro Met Ala Arg Arg
                        645
```

<210> SEQ ID NO 15
<211> LENGTH: 708
<212> TYPE: DNA
<213> ORGANISM: Artificial Sequence
<220> FEATURE:
<223> OTHER INFORMATION: Synthetic sequence

<400> SEQUENCE: 15

```
atggattttc aagtgcagat tttcagcttc ctgctaatca gtgcctcagt cataatatcc      60
agaggacaaa ttgttctcac ccagtctcca gcaatcatgt ctgcatctcc aggggagaag     120
gtcaccatga cctgcagtgc cagctcaagt gtaagtcaca tgcactggta ccagcagaag     180
tcaggcactt cccccaaaag atggatttat gacacatcca gactggcttc tggagtccct     240
gctcgcttca gtggcagtgg gtctgggacc tcttactctc tcacaatcag cagcatggag     300
gctgaagatg ctgccactta ttactgccag cagtggagta gtcacccatg gtcgttcggt     360
ggaggcacca aactcgagat caaacgaact gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag acagcacct acagcctcag cagcaccctg     600
acgctgagca agcagactac gagaaacac aaagtctatg cctgcgaagt cacccatcag     660
ggcctgagct cgcccgtcac aaagagcttc aacaggggag agtgttag                  708
```

<210> SEQ ID NO 16

```
<211> LENGTH: 213
<212> TYPE: PRT
<213> ORGANISM: Artificial Sequence
<220> FEATURE:
<223> OTHER INFORMATION: Synthetic sequence

<400> SEQUENCE: 16

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser His Met
            20                  25                  30

His Trp Tyr Gln Gln Lys Ser Gly Thr Ser Pro Lys Arg Trp Ile Tyr
        35                  40                  45

Asp Thr Ser Arg Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser His Pro Trp Ser
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 17
<211> LENGTH: 1773
<212> TYPE: DNA
<213> ORGANISM: Artificial Sequence
<220> FEATURE:
<223> OTHER INFORMATION: Synthetic sequence

<400> SEQUENCE: 17
atgagagcgc tgattctttt gtgcctgttc acagcctttc tggtatcct gtctgatgtg      60 cagcttcagg agtcaggacc tgacctggtg aaaccttctc agtcactttc actcacctgc    120
actgtcactg gctactccat caccagtggt tatagctggc actggatccg gcagtttcca    180
ggaaacaaac tggaatggat gggctacata ctcttcagtg gtagcactaa ctacaaccca    240
tctctgaaaa gtcgaatctc tatcactcga gacacatcca agaaccagtt cttcctgcag    300
ttgaattctg tgactactga ggacacagcc acatatttct gtgcaagatc taactatggt    360
tcctttgctt cctggggcca aggactctg gtcactgtct ctgcagccaa acaacgggc     420 ccatccgtct tccccctggc gccctgctcc aggagcacct ccgagagcac agccgccctg    480
ggctgcctgg tcaaggacta cttccccgaa ccggtgacgg tgtcgtggaa ctcaggcgcc    540
ctgaccagcg gcgtgcacac cttcccggct gtcctacagt cctcaggact ctactccctc    600
```

```
agcagcgtgg tgaccgtgcc ctccagcagc ttgggcacga agacctacac ctgcaacgta    660
gatcacaagc ccagcaacac caaggtggac aagagagttg agtccaaata tggtccccca    720
tgcccaccct gcccagcacc tgagttcgaa ggggggaccat cagtcttcct gttccccca    780
aaacccaagg acactctcat gatctcccgg acccctgagg tcacgtgcgt ggtggtggac    840
gtgagccagg aagaccccga ggtccagttc aactggtacg tggatggcgt ggaggtgcat    900
aatgccaaga caaagccgcg ggaggagcag ttcaacagca cgtaccgtgt ggtcagcgtc    960
ctcaccgtcc tgcaccagga ctggctgaac ggcaaggagt acaagtgcaa ggtctccaac   1020
aaaggcctcc cgtcctccat cgagaaaacc atctccaaag ccaaagggca gccccgagag   1080
ccacaggtgt acaccctgcc cccatcccag gaggagatga ccaagaacca ggtcagcctg   1140
acctgcctgg tcaaaggctt ctaccccagc gacatcgccg tggagtggga gagcaatggg   1200
cagccggaga acaactacaa gaccacgcct cccgtgctgg actccgacgg ctccttcttc   1260
ctctacagca ggctaaccgt ggacaagagc aggtggcagg aggggaatgt cttctcatgc   1320
tccgtgatgc atgaggctct gcacaaccac tacacacaga agagcctctc cctgtctctg   1380
ggtaaagcta gtggtcagtt tagagtcatt gggcccagac accctataag ggctcttgtg   1440
ggagacgagg tcgagctgcc cgtgtcgcatt agtccaggca aaaacgccac agggatggaa   1500
gtggggtggt acaggcctcc cttctctagg gttgtgcatc tctaccgcaa cggcaaagat   1560
caggatggag atcaagctcc tgaatatcgg ggccggactg agctgctcaa ggacgcgatc   1620
ggcgagggta aggtgacctt gcgcatccga aatgttagat tcagcgatga aggcggattt   1680
acgtgcttct ttcgggacca ctcataccag gaggaagccg caatggaact gaaggtggag   1740
gaccccttct attgggtatc cccagctagc tga                                1773
```

<210> SEQ ID NO 18
<211> LENGTH: 572
<212> TYPE: PRT
<213> ORGANISM: Artificial Sequence
<220> FEATURE:
<223> OTHER INFORMATION: Synthetic sequence

<400> SEQUENCE: 18

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
                20                  25                  30

Tyr Ser Trp His Trp Ile Arg Gln Phe Pro Gly Asn Lys Leu Glu Trp
            35                  40                  45

Met Gly Tyr Ile Leu Phe Ser Gly Ser Thr Asn Tyr Asn Pro Ser Leu
        50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Phe Cys
                85                  90                  95

Ala Arg Ser Asn Tyr Gly Ser Phe Ala Ser Trp Gly Gln Gly Thr Leu
            100                 105                 110

Val Thr Val Ser Ala Ala Lys Thr Thr Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser

```
                145                 150                 155                 160
        Gly Ala Leu Thr Ser Gly Val His Thr Phe Pro Ala Val Leu Gln Ser
                        165                 170                 175
        Ser Gly Leu Tyr Ser Leu Ser Ser Val Val Thr Val Pro Ser Ser Ser
                        180                 185                 190
        Leu Gly Thr Lys Thr Tyr Thr Cys Asn Val Asp His Lys Pro Ser Asn
                        195                 200                 205
        Thr Lys Val Asp Lys Arg Val Glu Ser Lys Tyr Gly Pro Pro Cys Pro
                210                 215                 220
        Pro Cys Pro Ala Pro Glu Phe Glu Gly Gly Pro Ser Val Phe Leu Phe
        225                 230                 235                 240
        Pro Pro Lys Pro Lys Asp Thr Leu Met Ile Ser Arg Thr Pro Glu Val
                        245                 250                 255
        Thr Cys Val Val Val Asp Val Ser Gln Glu Asp Pro Glu Val Gln Phe
                        260                 265                 270
        Asn Trp Tyr Val Asp Gly Val Glu Val His Asn Ala Lys Thr Lys Pro
                        275                 280                 285
        Arg Glu Glu Gln Phe Asn Ser Thr Tyr Arg Val Val Ser Val Leu Thr
                290                 295                 300
        Val Leu His Gln Asp Trp Leu Asn Gly Lys Glu Tyr Lys Cys Lys Val
        305                 310                 315                 320
        Ser Asn Lys Gly Leu Pro Ser Ser Ile Glu Lys Thr Ile Ser Lys Ala
                        325                 330                 335
        Lys Gly Gln Pro Arg Glu Pro Gln Val Tyr Thr Leu Pro Pro Ser Gln
                        340                 345                 350
        Glu Glu Met Thr Lys Asn Gln Val Ser Leu Thr Cys Leu Val Lys Gly
                        355                 360                 365
        Phe Tyr Pro Ser Asp Ile Ala Val Glu Trp Glu Ser Asn Gly Gln Pro
                370                 375                 380
        Glu Asn Asn Tyr Lys Thr Thr Pro Pro Val Leu Asp Ser Asp Gly Ser
        385                 390                 395                 400
        Phe Phe Leu Tyr Ser Arg Leu Thr Val Asp Lys Ser Arg Trp Gln Glu
                        405                 410                 415
        Gly Asn Val Phe Ser Cys Ser Val Met His Glu Ala Leu His Asn His
                        420                 425                 430
        Tyr Thr Gln Lys Ser Leu Ser Leu Ser Leu Gly Lys Ala Ser Gly Gln
                        435                 440                 445
        Phe Arg Val Ile Gly Pro Arg His Pro Ile Arg Ala Leu Val Gly Asp
                450                 455                 460
        Glu Val Glu Leu Pro Cys Arg Ile Ser Pro Gly Lys Asn Ala Thr Gly
        465                 470                 475                 480
        Met Glu Val Gly Trp Tyr Arg Pro Pro Phe Ser Arg Val Val His Leu
                        485                 490                 495
        Tyr Arg Asn Gly Lys Asp Gln Asp Gly Asp Gln Ala Pro Glu Tyr Arg
                        500                 505                 510
        Gly Arg Thr Glu Leu Leu Lys Asp Ala Ile Gly Glu Gly Lys Val Thr
                        515                 520                 525
        Leu Arg Ile Arg Asn Val Arg Phe Ser Asp Glu Gly Gly Phe Thr Cys
                530                 535                 540
        Phe Phe Arg Asp His Ser Tyr Gln Glu Glu Ala Ala Met Glu Leu Lys
        545                 550                 555                 560
        Val Glu Asp Pro Phe Tyr Trp Val Ser Pro Ala Ser
                        565                 570
```

<210> SEQ ID NO 19
<211> LENGTH: 708
<212> TYPE: DNA
<213> ORGANISM: Artificial Sequence
<220> FEATURE:
<223> OTHER INFORMATION: Synthetic sequence

<400> SEQUENCE: 19

```
atggattttc aagtgcagat tttcagcttc ctgctaatca gtgcctcagt cataatatcc      60
agaggacaaa ttgttctcac ccagtctcca gcaatcatgt ctgcatctcc aggggagaag     120
gtcaccatga cctgcagtgc cagctcaagt gtaagtcaca tgcactggta ccagcagaag     180
tcaggcactt cccccaaaag atggatttat gacacatcca gactggcttc tggagtccct     240
gctcgcttca gtggcagtgg gtctgggacc tcttactctc tcacaatcag cagcatggag     300
gctgaagatg ctgccactta ttactgccag cagtggagta gtcacccatg gtcgttcggt     360
ggaggcacca aactcgagat caaacgaact gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactac cgagaaacac aaagtctatg cctgcgaagt cacccatcag     660
ggcctgagct cgcccgtcac aaagagcttc aacaggggag agtgttag                  708
```

<210> SEQ ID NO 20
<211> LENGTH: 213
<212> TYPE: PRT
<213> ORGANISM: Artificial Sequence
<220> FEATURE:
<223> OTHER INFORMATION: Synthetic sequence

<400> SEQUENCE: 20

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser His Met
            20                  25                  30

His Trp Tyr Gln Gln Lys Ser Gly Thr Ser Pro Lys Arg Trp Ile Tyr
        35                  40                  45

Asp Thr Ser Arg Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser His Pro Trp Ser
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
```

```
            180                 185                 190
Cys Glu Val Thr His Gln Gly Leu Ser Ser Pro Val Thr Lys Ser Phe
            195                 200                 205

Asn Arg Gly Glu Cys
        210

<210> SEQ ID NO 21
<211> LENGTH: 1002
<212> TYPE: DNA
<213> ORGANISM: Artificial Sequence
<220> FEATURE:
<223> OTHER INFORMATION: Synthetic sequence

<400> SEQUENCE: 21
atggatccca aaggatccct ttcctggaga atacttctgt ttctctccct ggcttttgag      60
ttgagctacg gactcgacat cacatcccac catcaccatc accatgacga tctggatgca     120
gtaaggatta aagtggacac agtaaatgca aaaccgggag acacagtaag aatacctgta     180
agattcagcg gtataccatc caagggaata gcaaactgtg actttgtata cagctatgac     240
ccgaatgtac ttgagataat agagatagaa ccgggagaca taatagttga cccgaatcct     300
gacaagagct ttgatactgc agtatatcct gacagaaaga taatagtatt cctgtttgca     360
gaagacagcg gaacaggagc gtatgcaata actaaagacg gagtatttgc tacgatagta     420
gcgaaagtaa aagaaggagc acctaacgga ctcagtgtaa tcaaatttgt agaagtaggc     480
ggatttgcga caatgaccct tgtagaacag aagacacagt tctttgacgg tggagtaaat     540
gttggagata caacagaacc tgcaacacct acaacacctg taacaacacc gacaacaaca     600
gatgatctgg atgcagctag tggtcagttt agagtcattg gcccagacc cctataagg       660
gctcttgtgg gagacgaggt cgagctgccg tgtcgcatta gtccaggcaa aaacgccaca     720
gggatggaag tggggtggta caggcctccc ttctctaggg ttgtgcatct ctaccgcaac     780
ggcaaagatc aggatggaga tcaagctcct gaatatcggg gccggactga gctgctcaag     840
gacgcgatcg gcgagggtaa ggtgaccttg cgcatccgaa atgttagatt cagcgatgaa     900
ggcggattta cgtgcttctt tcgggaccac tcataccagg aggaagccgc aatggaactg     960
aaggtggagg accccttcta ttgggtatcc ccagctagct ga                        1002

<210> SEQ ID NO 22
<211> LENGTH: 309
<212> TYPE: PRT
<213> ORGANISM: Artificial Sequence
<220> FEATURE:
<223> OTHER INFORMATION: Synthetic sequence

<400> SEQUENCE: 22

Leu Asp Ile Thr Ser His His His His His Asp Asp Leu Asp Ala
1               5                   10                  15

Val Arg Ile Lys Val Asp Thr Val Asn Ala Lys Pro Gly Asp Thr Val
            20                  25                  30

Arg Ile Pro Val Arg Phe Ser Gly Ile Pro Ser Lys Gly Ile Ala Asn
        35                  40                  45

Cys Asp Phe Val Tyr Ser Tyr Asp Pro Asn Val Leu Glu Ile Ile Glu
    50                  55                  60

Ile Glu Pro Gly Asp Ile Ile Val Asp Pro Asn Pro Asp Lys Ser Phe
65                  70                  75                  80

Asp Thr Ala Val Tyr Pro Asp Arg Lys Ile Ile Val Phe Leu Phe Ala
                85                  90                  95
```

Glu Asp Ser Gly Thr Gly Ala Tyr Ala Ile Thr Lys Asp Gly Val Phe
                100                 105                 110

Ala Thr Ile Val Ala Lys Val Lys Glu Gly Ala Pro Asn Gly Leu Ser
            115                 120                 125

Val Ile Lys Phe Val Glu Val Gly Gly Phe Ala Asn Asn Asp Leu Val
        130                 135                 140

Glu Gln Lys Thr Gln Phe Phe Asp Gly Val Asn Val Gly Asp Thr
145                 150                 155                 160

Thr Glu Pro Ala Thr Pro Thr Thr Pro Val Thr Thr Pro Thr Thr Thr
                165                 170                 175

Asp Asp Leu Asp Ala Ala Ser Gly Gln Phe Arg Val Ile Gly Pro Arg
            180                 185                 190

His Pro Ile Arg Ala Leu Val Gly Asp Glu Val Glu Leu Pro Cys Arg
        195                 200                 205

Ile Ser Pro Gly Lys Asn Ala Thr Gly Met Glu Val Gly Trp Tyr Arg
    210                 215                 220

Pro Pro Phe Ser Arg Val Val His Leu Tyr Arg Asn Gly Lys Asp Gln
225                 230                 235                 240

Asp Gly Asp Gln Ala Pro Glu Tyr Arg Gly Arg Thr Glu Leu Leu Lys
                245                 250                 255

Asp Ala Ile Gly Glu Gly Lys Val Thr Leu Arg Ile Arg Asn Val Arg
            260                 265                 270

Phe Ser Asp Glu Gly Gly Phe Thr Cys Phe Phe Arg Asp His Ser Tyr
        275                 280                 285

Gln Glu Glu Ala Ala Met Glu Leu Lys Val Glu Asp Pro Phe Tyr Trp
    290                 295                 300

Val Ser Pro Ala Ser
305

<210> SEQ ID NO 23
<211> LENGTH: 1098
<212> TYPE: DNA
<213> ORGANISM: Artificial Sequence
<220> FEATURE:
<223> OTHER INFORMATION: Synthetic sequence

<400> SEQUENCE: 23
atgggcagca gccatcatca tcatcatcac agcagcggcc tggtgccgcg cggcagccat      60
atggctagta tggatctgga tgcagtaagg attaaagtgg acacagtaaa tgcaaaaccg     120
ggagacacag taaatatacc tgtaagattc agtggtatac atccaaggg aatagcaaac      180 tgtgactttg tatacagcta tgacccgaat gtacttgaga atagagat aaaaccggga       240 gaattgatag ttgaccccga atcctaccaag agctttgata ctgcagtata tcctgacaga    300
aagatgatag tattcctgtt tgcggaagac agcggaacag gagcgtatgc aataactaaa     360
gacggagtat ttgctacgat agtagcgaaa gtaaaagaag gagcacctaa cgggctcagt     420
gtaatcaaat ttgtagaagt aggcggattt gcgaacaatg accttgtaga acagaagaca     480
cagttctttg acggtggagt aaatgttgga gatacaacag aacctgcaac acctacaaca     540
cctgtaacaa caccgacaac aacagatgat ctagatgcag ctagtgcatc acaaaagcgg     600
ccttcacaac ggcacggatc taaatatctg cgacagcct ctaccatgga tcacgccagg      660
catggctttc tgcccaggca cagagatact ggaatcttgg actccatcgg caggttcttt     720
ggcggcgacc gaggggctcc caagagaggg agtggcaagg atagccatca tccagcccga     780

```
acagcccact acggaagcct gccgcagaaa agccacggtc gcacgcagga tgaaaatccc      840
gttgtgcact tcttcaaaaa cattgtgacc ccacgaactc ctccaccttc ccaaggcaag      900
ggcagaggtc tcagtctcag ccggttcagt tgggggccg agggccagag accggattt       960 ggttatgggg gaagggctag cgactacaag tctgcacata aggggttcaa aggggtcgac    1020
gcacagggaa ccctgtccaa aatatttaag cttggtggcc gcgactcccg ctcaggctct    1080
cccatggctc ggcgctga                                                   1098
```

<210> SEQ ID NO 24
<211> LENGTH: 365
<212> TYPE: PRT
<213> ORGANISM: Artificial Sequence
<220> FEATURE:
<223> OTHER INFORMATION: Synthetic sequence

<400> SEQUENCE: 24

```
Met Gly Ser Ser His His His His His Ser Ser Gly Leu Val Pro
1               5                   10                  15

Arg Gly Ser His Met Ala Ser Met Asp Leu Asp Ala Val Arg Ile Lys
            20                  25                  30

Val Asp Thr Val Asn Ala Lys Pro Gly Asp Thr Val Asn Ile Pro Val
        35                  40                  45

Arg Phe Ser Gly Ile Pro Ser Lys Gly Ile Ala Asn Cys Asp Phe Val
    50                  55                  60

Tyr Ser Tyr Asp Pro Asn Val Leu Glu Ile Ile Glu Ile Lys Pro Gly
65                  70                  75                  80

Glu Leu Ile Val Asp Pro Asn Pro Thr Lys Ser Phe Asp Thr Ala Val
                85                  90                  95

Tyr Pro Asp Arg Lys Met Ile Val Phe Leu Phe Ala Glu Asp Ser Gly
            100                 105                 110

Thr Gly Ala Tyr Ala Ile Thr Lys Asp Gly Val Phe Ala Thr Ile Val
        115                 120                 125

Ala Lys Val Lys Glu Gly Ala Pro Asn Gly Leu Ser Val Ile Lys Phe
    130                 135                 140

Val Glu Val Gly Gly Phe Ala Asn Asn Asp Leu Val Glu Gln Lys Thr
145                 150                 155                 160

Gln Phe Phe Asp Gly Gly Val Asn Val Gly Asp Thr Thr Glu Pro Ala
                165                 170                 175

Thr Pro Thr Thr Pro Val Thr Thr Pro Thr Thr Thr Asp Asp Leu Asp
            180                 185                 190

Ala Ala Ser Ala Ser Gln Lys Arg Pro Ser Gln Arg His Gly Ser Lys
        195                 200                 205

Tyr Leu Ala Thr Ala Ser Thr Met Asp His Ala Arg His Gly Phe Leu
    210                 215                 220

Pro Arg His Arg Asp Thr Gly Ile Leu Asp Ser Ile Gly Arg Phe Phe
225                 230                 235                 240

Gly Gly Asp Arg Gly Ala Pro Lys Arg Gly Ser Gly Lys Asp Ser His
                245                 250                 255

His Pro Ala Arg Thr Ala His Tyr Gly Ser Leu Pro Gln Lys Ser His
            260                 265                 270

Gly Arg Thr Gln Asp Glu Asn Pro Val Val His Phe Phe Lys Asn Ile
        275                 280                 285

Val Thr Pro Arg Thr Pro Pro Ser Gln Gly Lys Gly Arg Gly Leu
    290                 295                 300
```

```
Ser Leu Ser Arg Phe Ser Trp Gly Ala Glu Gly Gln Arg Pro Gly Phe
305                 310                 315                 320

Gly Tyr Gly Gly Arg Ala Ser Asp Tyr Lys Ser Ala His Lys Gly Phe
            325                 330                 335

Lys Gly Val Asp Ala Gln Gly Thr Leu Ser Lys Ile Phe Lys Leu Gly
        340                 345                 350

Gly Arg Asp Ser Arg Ser Gly Ser Pro Met Ala Arg Arg
        355                 360                 365

<210> SEQ ID NO 25
<211> LENGTH: 1785
<212> TYPE: DNA
<213> ORGANISM: Artificial Sequence
<220> FEATURE:
<223> OTHER INFORMATION: Synthetic sequence

<400> SEQUENCE: 25
```

| | | |
|---|---|---|
| atggaatgga gcggggtctt tatctttctc ctgtcagtaa ctgcaggtgc ccactcccag | 60 |
| gtccagctgc agcagtctgg agctgagctg gtaaggcctg gacttcagt gaagatgtcc | 120 |
| tgcgaggctg ctagattcac cttcagtaac tactggattg gttgggtaaa gcagaggcct | 180 |
| ggacatggcc ttgagtggat tggagatatt ttccctggag tgattatac taactacaat | 240 |
| aagaaattca aggacaaggc cacactgact gcagacacat cctccagcac agcctacatg | 300 |
| cagctcagca gcctgacatc tgaggactct gccatctatt actgtgcaag atcggactac | 360 |
| ggtggttact acgtctttga ctactggggc caaggcacca ctctcacagt ctcctcagcc | 420 |
| aaaacaaagg gcccatccgt cttccccctg gcgccctgct ccaggagcac ctccgagagc | 480 |
| acagccgccc tgggctgcct ggtcaaggac tacttcccg aaccggtgac ggtgtcgtgg | 540 |
| aactcaggcg ccctgaccag cggcgtgcac accttcccgg ctgtcctaca gtcctcagga | 600 |
| ctctactccc tcagcagcgt ggtgaccgtg ccctccagca gcttgggcac gaagacctac | 660 |
| acctgcaacg tagatcacaa gcccagcaac accaaggtgg acaagagagt tgagtccaaa | 720 |
| tatggtcccc catgcccacc ctgcccagca cctgagttcg aaggggacc atcagtcttc | 780 |
| ctgttccccc caaaacccaa ggacactctc atgatctccc ggaccctga ggtcacgtgc | 840 |
| gtggtggtgg acgtgagcca ggaagacccc gaggtccagt tcaactggta cgtggatggc | 900 |
| gtggaggtgc ataatgccaa gacaaagccg cgggaggagc agttcaacag cacgtaccgt | 960 |
| gtggtcagcg tcctcaccgt cctgcaccag gactggctga acggcaagga gtacaagtgc | 1020 |
| aaggtctcca acaaaggcct cccgtcctcc atcgagaaaa ccatctccaa agccaaaggg | 1080 |
| cagccccgag agccacaggt gtacaccctg cccccatccc aggaggagat gaccaagaac | 1140 |
| caggtcagcc tgacctgcct ggtcaaaggc ttctacccca gcgacatcgc cgtggagtgg | 1200 |
| gagagcaatg ggcagccgga gaacaactac aagaccacgc ctcccgtgct ggactccgac | 1260 |
| ggctccttct tcctctacag caggctaacc gtggacaaga gcaggtggca ggaggggaat | 1320 |
| gtcttctcat gctccgtgat gcatgaggct ctgcacaacc actacacaca gaagagcctc | 1380 |
| tccctgtctc tgggtaaagc tagtggtcag tttagagtca ttgggcccag acaccctata | 1440 |
| agggctcttg tgggagacga ggtcgagctg ccgtgtcgca ttagtccagg caaaaacgcc | 1500 |
| acagggatgg aagtggggtg gtacaggcct cccttctcta gggttgtgca tctctaccgc | 1560 |
| aacggcaaag atcaggatgg agatcaagct cctgaatatc ggggccggac tgagctgctc | 1620 |
| aaggacgcga tcgcgagggg taaggtgacc ttgcgcatcc gaaatgttag attcagcgat | 1680 |
| gaaggcggat ttacgtgctt ctttcgggac cactcatacc aggaggaagc cgcaatggaa | 1740 |

```
ctgaaggtgg aggacccctt ctattgggta tccccagcta gctga              1785
```

<210> SEQ ID NO 26
<211> LENGTH: 575
<212> TYPE: PRT
<213> ORGANISM: Artificial Sequence
<220> FEATURE:
<223> OTHER INFORMATION: Synthetic sequence

<400> SEQUENCE: 26

```
Gln Val Gln Leu Gln Gln Ser Gly Ala Glu Leu Val Arg Pro Gly Thr
 1               5                  10                  15

Ser Val Lys Met Ser Cys Glu Ala Ala Arg Phe Thr Phe Ser Asn Tyr
            20                  25                  30

Trp Ile Gly Trp Val Lys Gln Arg Pro Gly His Gly Leu Glu Trp Ile
        35                  40                  45

Gly Asp Ile Phe Pro Gly Gly Asp Tyr Thr Asn Tyr Asn Lys Lys Phe
    50                  55                  60

Lys Asp Lys Ala Thr Leu Thr Ala Asp Thr Ser Ser Thr Ala Tyr
 65                  70                  75                  80

Met Gln Leu Ser Ser Leu Thr Ser Glu Asp Ser Ala Ile Tyr Tyr Cys
                85                  90                  95

Ala Arg Ser Asp Tyr Gly Gly Tyr Tyr Val Phe Asp Tyr Trp Gly Gln
            100                 105                 110

Gly Thr Thr Leu Thr Val Ser Ser Ala Lys Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350
```

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys Ala
                435                 440                 445

Ser Gly Gln Phe Arg Val Ile Gly Pro Arg His Pro Ile Arg Ala Leu
    450                 455                 460

Val Gly Asp Glu Val Glu Leu Pro Cys Arg Ile Ser Pro Gly Lys Asn
465                 470                 475                 480

Ala Thr Gly Met Glu Val Gly Trp Tyr Arg Pro Pro Phe Ser Arg Val
                485                 490                 495

Val His Leu Tyr Arg Asn Gly Lys Asp Gln Asp Gly Asp Gln Ala Pro
                500                 505                 510

Glu Tyr Arg Gly Arg Thr Glu Leu Leu Lys Asp Ala Ile Gly Glu Gly
    515                 520                 525

Lys Val Thr Leu Arg Ile Arg Asn Val Arg Phe Ser Asp Glu Gly Gly
530                 535                 540

Phe Thr Cys Phe Phe Arg Asp His Ser Tyr Gln Glu Glu Ala Ala Met
545                 550                 555                 560

Glu Leu Lys Val Glu Asp Pro Phe Tyr Trp Val Ser Pro Ala Ser
                565                 570                 575

<210> SEQ ID NO 27
<211> LENGTH: 729
<212> TYPE: DNA
<213> ORGANISM: Artificial Sequence
<220> FEATURE:
<223> OTHER INFORMATION: Synthetic sequence

<400> SEQUENCE: 27
atggattcac aggcccaggt tcttatgtta ctgctgctat gggtatctgg tacctgtggg      60
gacattgtga tgtcacagtc tccatcctcc ctagctgtgt cagttggaga aaggttact     120 atgagctgca agtccagtca gaaccttta tatagtagca tcaaaagaa ctacttggcc      180 tggtaccagc agaaaccagg gcagtctcct aaactgctga tttactgggc atccactagg     240
gaatctgggg tccctgatcg cttcacaggc agtggatctg ggacagattt cactctcacc     300
atcagcagtg tgaaggctga agacctggca gtctattact gtcagcaata ttatagctat     360
ccttacacgt tcggaggggg gaccaagctc gagatcaaac gaactgtggc tgcaccatct     420
gtcttcatct tcccgccatc tgatgagcag ttgaaatctg gaactgcctc tgttgtgtgc     480
ctgctgaata acttctatcc cagagaggcc aaagtacagt ggaaggtgga taacgccctc     540
caatcgggta actcccagga gagtgtcaca gagcaggaca gcaaggacag cacctacagc     600
ctcagcagca ccctgacgct gagcaaagca gactacgaga acacaaagt ctatgcctgc     660 gaagtcaccc atcagggcct gagctcgccc gtcacaaaga gcttcaacag gggagagtgt     720
gctagctga                                                            729

<210> SEQ ID NO 28
<211> LENGTH: 222
<212> TYPE: PRT
<213> ORGANISM: Artificial Sequence
<220> FEATURE:
<223> OTHER INFORMATION: Synthetic sequence

<400> SEQUENCE: 28

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Asn Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Ala Ser
    210                 215                 220
```

<210> SEQ ID NO 29
<211> LENGTH: 1776
<212> TYPE: DNA
<213> ORGANISM: Artificial Sequence
<220> FEATURE:
<223> OTHER INFORMATION: Synthetic sequence

<400> SEQUENCE: 29

```
atggcttggg tgtggacctt gctattcctg atggcagccg cccaaagtat ccaagcacag     60
atccagttgg tgcagtctgg acctgagctg aagaagcctg agagacagt caagatctcc    120 tgcaaggctt ctggttatac cttcacagac tattcagtgc actgggtgaa gcaggctcca    180
ggaaagggtt taaagtggat gggctggata aatactgaga ctggtgagcc aacatatgca    240
gatgacctca gggacggtt tgccttctct ttggaaacct ctgccagcac tgcctatttg    300
cagatcaaca acctcaaaaa tgaggacacg gctacatatt tctgtgctaa acctacctat    360 agatttttg actactgggg ccaaggcacc actctcacag cctcctcagc caaaacgaag    420
ggcccatccg tcttcccccct ggcgccctgc tccaggagca cctccgagag cacagccgcc    480
ctgggctgcc tggtcaagga ctacttcccc gaaccggtga cggtgtcgtg gaactcaggc    540
```

```
gccctgacca gcggcgtgca caccttcccg gctgtcctac agtcctcagg actctactcc      600
ctcagcagcg tggtgaccgt gccctccagc agcttgggca cgaagaccta cacctgcaac      660
gtagatcaca agcccagcaa caccaaggtg gacaagagag ttgagtccaa atatggtccc      720
ccatgcccac cctgcccagc acctgagttc aaggggggac catcagtctt cctgttcccc      780
ccaaaaccca aggacactct catgatctcc cggacccctg aggtcacgtg cgtggtggtg      840
gacgtgagcc aggaagaccc cgaggtccag ttcaactggt acgtggatgg cgtggaggtg      900
cataatgcca agacaaagcc gcgggaggag cagttcaaca gcacgtaccg tgtggtcagc      960
gtcctcaccg tcctgcacca ggactggctg aacggcaagg agtacaagtg caaggtctcc     1020
aacaaaggcc tcccgtcctc catcgagaaa accatctcca aagccaaagg gcagccccga     1080
gagccacagg tgtacaccct gcccccatcc caggaggaga tgaccaagaa ccaggtcagc     1140
ctgacctgcc tggtcaaagg cttctacccc agcgacatcg ccgtggagtg ggagagcaat     1200
gggcagccgg agaacaacta caagaccacg cctcccgtgc tggactccga cggctccttc     1260
ttcctctaca gcaggctaac cgtggacaag agcaggtggc aggaggggaa tgtcttctca     1320
tgctccgtga tgcatgaggc tctgcacaac cactacacac agaagagcct ctccctgtct     1380
ctgggtaaag ctagtggtca gtttagagtc attgggccca gacaccctat aagggctctt     1440
gtgggagacg aggtcgagct gccgtgtcgc attagtccag gcaaaaacgc cacagggatg     1500
gaagtggggt ggtacaggcc tcccttctct agggttgtgc atctctaccg caacggcaaa     1560
gatcaggatg gagatcaagc tcctgaatat cggggccgga ctgagctgct caaggacgcg     1620
atcggcgagg taaggtgtac cttgcgcatc cgaaatgtta gattcagcga tgaaggcgga     1680
tttacgtgct tctttcggga ccactcatac caggaggaag ccgcaatgga actgaaggtg     1740
gaggacccct tctattgggt atccccagct agctga                              1776
```

<210> SEQ ID NO 30
<211> LENGTH: 573
<212> TYPE: PRT
<213> ORGANISM: Artificial Sequence
<220> FEATURE:
<223> OTHER INFORMATION: Synthetic sequence

<400> SEQUENCE: 30

```
Ala Gln Ile Gln Leu Val Gln Ser Gly Pro Glu Leu Lys Lys Pro Gly
1               5                   10                  15

Glu Thr Val Lys Ile Ser Cys Lys Ala Ser Gly Tyr Thr Phe Thr Asp
            20                  25                  30

Tyr Ser Val His Trp Val Lys Gln Ala Pro Gly Lys Gly Leu Lys Trp
        35                  40                  45

Met Gly Trp Ile Asn Thr Glu Thr Gly Glu Pro Thr Tyr Ala Asp Asp
    50                  55                  60

Leu Lys Gly Arg Phe Ala Phe Ser Leu Glu Thr Ser Ala Ser Thr Ala
65                  70                  75                  80

Tyr Leu Gln Ile Asn Asn Leu Lys Asn Glu Asp Thr Ala Thr Tyr Phe
                85                  90                  95

Cys Ala Lys Pro Thr Tyr Arg Phe Phe Asp Tyr Trp Gly Gln Gly Thr
            100                 105                 110

Thr Leu Thr Ala Ser Ser Ala Lys Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140
```

-continued

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
            210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys Ala Ser Gly
            435                 440                 445

Gln Phe Arg Val Ile Gly Pro Arg His Pro Ile Arg Ala Leu Val Gly
    450                 455                 460

Asp Glu Val Glu Leu Pro Cys Arg Ile Ser Pro Gly Lys Asn Ala Thr
465                 470                 475                 480

Gly Met Glu Val Gly Trp Tyr Arg Pro Pro Phe Ser Arg Val Val His
            485                 490                 495

Leu Tyr Arg Asn Gly Lys Asp Gln Asp Gly Asp Gln Ala Pro Glu Tyr
            500                 505                 510

Arg Gly Arg Thr Glu Leu Leu Lys Asp Ala Ile Gly Glu Gly Lys Val
            515                 520                 525

Thr Leu Arg Ile Arg Asn Val Arg Phe Ser Asp Glu Gly Gly Phe Thr
            530                 535                 540

Cys Phe Phe Arg Asp His Ser Tyr Gln Glu Glu Ala Ala Met Glu Leu
545                 550                 555                 560

Lys Val Glu Asp Pro Phe Tyr Trp Val Ser Pro Ala Ser

<210> SEQ ID NO 31
<211> LENGTH: 726
<212> TYPE: DNA
<213> ORGANISM: Artificial Sequence
<220> FEATURE:
<223> OTHER INFORMATION: Synthetic sequence

<400> SEQUENCE: 31

```
atggattcac aggcccaggt tcttatattg ctgctgctat gggtatctgg ttcctgtggg      60
gacattgtga tgtcacagtc tccatcctcc ctggctgtgt cagcaggaga aaggtcact     120
atgagctgca atccagtca gagtctgctc aacagtagaa cccgaaagaa ctacttggct     180
tggtaccagc agaaaccagg gcagtctcct aaactgctga tctactgggc atccactagg     240
gaatctgggg tccctgatcg cttcacaggc agtggatctg gacagattt cactctcacc     300
atcagcagtg tgcaggctga ggacctggca gtttattact gcaagcaatc ttataatctg     360
tggacgttcg gtggaggcac caagctcgag atcaaacgaa ctgtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta tgcctgcgaa     660
gtcacccatc agggcctgag ctcgcccgtc acaaagagct tcaacagggg agagtgtgct     720
agctga                                                                726
```

<210> SEQ ID NO 32
<211> LENGTH: 221
<212> TYPE: PRT
<213> ORGANISM: Artificial Sequence
<220> FEATURE:
<223> OTHER INFORMATION: Synthetic sequence

<400> SEQUENCE: 32

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser

```
                       165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Ala Ser
    210                 215                 220

<210> SEQ ID NO 33
<211> LENGTH: 27
<212> TYPE: PRT
<213> ORGANISM: Artificial Sequence
<220> FEATURE:
<223> OTHER INFORMATION: Synthetic sequence

<400> SEQUENCE: 33

Gln Thr Pro Thr Asn Thr Ile Ser Val Thr Pro Thr Asn Asn Ser Thr
1               5                   10                  15

Pro Thr Asn Asn Ser Asn Pro Lys Pro Asn Pro
            20                  25

<210> SEQ ID NO 34
<211> LENGTH: 123
<212> TYPE: PRT
<213> ORGANISM: Artificial Sequence
<220> FEATURE:
<223> OTHER INFORMATION: Synthetic sequence

<400> SEQUENCE: 34

Pro Ser Glu Thr Pro Glu Glu Pro Ile Pro Thr Asp Thr Pro Ser Asp
1               5                   10                  15

Glu Pro Thr Pro Ser Asp Glu Pro Thr Pro Ser Asp Glu Pro Thr Pro
            20                  25                  30

Ser Asp Glu Pro Thr Pro Ser Asp Glu Pro Thr Pro Ser Asp Glu Pro
        35                  40                  45

Thr Pro Ser Asp Glu Pro Thr Pro Ser Glu Thr Pro Glu Glu Pro Thr
    50                  55                  60

Pro Thr Thr Thr Pro Thr Pro Thr Pro Ser Thr Thr Pro Thr Ser Gly
65                  70                  75                  80

Ser Gly Gly Ser Gly Gly Ser Gly Gly Gly Gly Gly Gly Gly Gly Gly
                85                  90                  95

Thr Val Pro Thr Ser Pro Thr Pro Thr Pro Thr Ser Lys Pro Thr Ser
            100                 105                 110

Thr Pro Ala Pro Thr Glu Ile Glu Glu Pro Thr
        115                 120

<210> SEQ ID NO 35
<211> LENGTH: 124
<212> TYPE: PRT
<213> ORGANISM: Artificial Sequence
<220> FEATURE:
<223> OTHER INFORMATION: Synthetic sequence

<400> SEQUENCE: 35

Asp Glu Pro Ile Pro Thr Asp Thr Pro Ser Asp Glu Pro Thr Pro Ser
1               5                   10                  15

Asp Glu Pro Thr Pro Ser Asp Glu Pro Thr Pro Ser Asp Glu Pro Thr
            20                  25                  30

Pro Ser Asp Glu Pro Thr Pro Ser Glu Thr Pro Glu Glu Pro Ile Pro
        35                  40                  45
```

```
Thr Asp Thr Pro Ser Asp Glu Pro Thr Pro Ser Asp Glu Pro Thr Pro
        50                  55                  60

Ser Asp Glu Pro Thr Pro Ser Asp Glu Pro Thr Pro Ser Asp Glu Pro
65                  70                  75                  80

Thr Pro Ser Glu Thr Pro Glu Glu Pro Ile Pro Thr Asp Thr Pro Ser
                85                  90                  95

Asp Glu Pro Thr Pro Ser Asp Glu Pro Thr Pro Ser Asp Glu Pro Thr
            100                 105                 110

Pro Ser Asp Glu Pro Thr Pro Ser Asp Glu Pro Thr
            115                 120

<210> SEQ ID NO 36
<211> LENGTH: 168
<212> TYPE: PRT
<213> ORGANISM: Artificial Sequence
<220> FEATURE:
<223> OTHER INFORMATION: Synthetic sequence

<400> SEQUENCE: 36

Gln Lys Arg Pro Ser Gln Arg His Gly Ser Lys Tyr Leu Ala Thr Ala
1               5                   10                  15

Ser Thr Met Asp His Ala Arg His Gly Phe Leu Pro Arg His Arg Asp
            20                  25                  30

Thr Gly Ile Leu Asp Ser Ile Gly Arg Phe Phe Gly Gly Asp Arg Gly
        35                  40                  45

Ala Pro Lys Arg Gly Ser Gly Lys Asp Ser His His Pro Ala Arg Thr
    50                  55                  60

Ala His Tyr Gly Ser Leu Pro Gln Lys Ser His Gly Arg Thr Gln Asp
65              70                  75                  80

Glu Asn Pro Val Val His Phe Phe Lys Asn Ile Val Thr Pro Arg Thr
                85                  90                  95

Pro Pro Pro Ser Gln Gly Lys Gly Arg Gly Leu Ser Leu Ser Arg Phe
            100                 105                 110

Ser Trp Gly Ala Glu Gly Gln Arg Pro Gly Phe Gly Tyr Gly Gly Arg
        115                 120                 125

Ala Ser Asp Tyr Lys Ser Ala His Lys Gly Phe Lys Gly Val Asp Ala
    130                 135                 140

Gln Gly Thr Leu Ser Lys Ile Phe Lys Leu Gly Gly Arg Asp Ser Arg
145                 150                 155                 160

Ser Gly Ser Pro Met Ala Arg Arg
                165

<210> SEQ ID NO 37
<211> LENGTH: 124
<212> TYPE: PRT
<213> ORGANISM: Artificial Sequence
<220> FEATURE:
<223> OTHER INFORMATION: Synthetic sequence

<400> SEQUENCE: 37

Gly Gln Phe Arg Val Ile Gly Pro Arg His Pro Ile Arg Ala Leu Val
1               5                   10                  15

Gly Asp Glu Val Glu Leu Pro Cys Arg Ile Ser Pro Gly Lys Asn Ala
            20                  25                  30

Thr Gly Met Glu Val Gly Trp Tyr Arg Pro Pro Phe Ser Arg Val Val
        35                  40                  45

His Leu Tyr Arg Asn Gly Lys Asp Gln Asp Gly Asp Gln Ala Pro Glu
```

```
            50                  55                  60
Tyr Arg Gly Arg Thr Glu Leu Leu Lys Asp Ala Ile Gly Glu Gly Lys
 65                  70                  75                  80

Val Thr Leu Arg Ile Arg Asn Val Arg Phe Ser Asp Glu Gly Gly Phe
                 85                  90                  95

Thr Cys Phe Phe Arg Asp His Ser Tyr Gln Glu Glu Ala Ala Met Glu
            100                 105                 110

Leu Lys Val Glu Asp Pro Phe Tyr Trp Val Ser Pro
        115                 120
```

<210> SEQ ID NO 38
<211> LENGTH: 169
<212> TYPE: PRT
<213> ORGANISM: Artificial Sequence
<220> FEATURE:
<223> OTHER INFORMATION: Synthetic sequence

<400> SEQUENCE: 38

```
Asp Leu Asp Ala Val Arg Ile Lys Val Asp Thr Val Asn Ala Lys Pro
 1               5                  10                  15

Gly Asp Thr Val Arg Ile Pro Val Arg Phe Ser Gly Ile Pro Ser Lys
                20                  25                  30

Gly Ile Ala Asn Cys Asp Phe Val Tyr Ser Tyr Asp Pro Asn Val Leu
            35                  40                  45

Glu Ile Ile Glu Ile Glu Pro Gly Asp Ile Ile Val Asp Pro Asn Pro
     50                  55                  60

Asp Lys Ser Phe Asp Thr Ala Val Tyr Pro Asp Arg Lys Ile Ile Val
 65                  70                  75                  80

Phe Leu Phe Ala Glu Asp Ser Gly Thr Gly Ala Tyr Ala Ile Thr Lys
                 85                  90                  95

Asp Gly Val Phe Ala Thr Ile Val Ala Lys Val Lys Glu Gly Ala Pro
            100                 105                 110

Asn Gly Leu Ser Val Ile Lys Phe Val Glu Val Gly Gly Phe Ala Asn
        115                 120                 125

Asn Asp Leu Val Glu Gln Lys Thr Gln Phe Phe Asp Gly Gly Val Asn
    130                 135                 140

Val Gly Asp Thr Thr Glu Pro Ala Thr Pro Thr Thr Pro Val Thr Thr
145                 150                 155                 160

Pro Thr Thr Thr Asp Asp Leu Asp Ala
                165
```

<210> SEQ ID NO 39
<211> LENGTH: 63
<212> TYPE: PRT
<213> ORGANISM: Artificial Sequence
<220> FEATURE:
<223> OTHER INFORMATION: Synthetic sequence

<400> SEQUENCE: 39

```
Gly Asp Val Asn Asp Asp Gly Lys Val Asn Ser Thr Asp Leu Thr Leu
 1               5                  10                  15

Leu Lys Arg Tyr Val Leu Lys Ala Val Ser Thr Leu Pro Ser Ser Lys
                20                  25                  30

Ala Glu Lys Asn Ala Asp Val Asn Arg Asp Gly Arg Val Asp Val Thr
            35                  40                  45

Ile Leu Ser Arg Tyr Leu Ile Arg Val Ile Glu Lys Leu Pro Ile
     50                  55                  60
```

```
<210> SEQ ID NO 40
<211> LENGTH: 230
<212> TYPE: PRT
<213> ORGANISM: Artificial Sequence
<220> FEATURE:
<223> OTHER INFORMATION: Synthetic sequence

<400> SEQUENCE: 40

Ile Glu Arg Leu Ser Ser Gly Leu Arg Ile Asn Ser Ala Lys Asp Asp
1               5                   10                  15

Ala Ala Gly Gln Ala Ile Ala Asn Arg Phe Thr Ala Asn Ile Lys Gly
                20                  25                  30

Leu Thr Gln Ala Ser Arg Asn Ala Asn Asp Gly Ile Ser Ile Ala Gln
            35                  40                  45

Thr Thr Glu Gly Ala Leu Asn Glu Ile Asn Asn Leu Gln Arg Val
    50                  55                  60

Arg Glu Leu Ala Val Gln Ser Ala Asn Ser Thr Asn Ser Gln Ser Asp
65                  70                  75                  80

Leu Asp Ser Ile Gln Ala Glu Ile Thr Gln Arg Leu Asn Glu Ile Asp
                85                  90                  95

Arg Val Ser Gly Gln Thr Gln Phe Asn Gly Val Lys Val Leu Ala Gln
            100                 105                 110

Asp Asn Thr Leu Thr Ile Gln Val Gly Ala Asn Asp Gly Glu Thr Ile
        115                 120                 125

Asp Ile Asp Leu Lys Gln Ile Asn Ser Gln Thr Leu Gly Leu Asp Ser
130                 135                 140

Leu Asn Val Gln Ala Ser Gln Pro Glu Leu Ala Glu Ala Ala Lys
145                 150                 155                 160

Thr Thr Glu Asn Pro Leu Gln Lys Ile Asp Ala Ala Leu Ala Gln Val
                165                 170                 175

Asp Ala Leu Arg Ser Asp Leu Gly Ala Val Gln Asn Arg Phe Asn Ser
            180                 185                 190

Ala Ile Thr Asn Leu Gly Asn Thr Val Asn Asn Leu Ser Glu Ala Arg
        195                 200                 205

Ser Arg Ile Glu Asp Ser Asp Tyr Ala Thr Glu Val Ser Asn Met Ser
    210                 215                 220

Arg Ala Gln Ile Leu Gln
225                 230

<210> SEQ ID NO 41
<211> LENGTH: 159
<212> TYPE: PRT
<213> ORGANISM: Artificial Sequence
<220> FEATURE:
<223> OTHER INFORMATION: Synthetic sequence

<400> SEQUENCE: 41

Pro Gly Gln Gly Thr Gln Ser Glu Asn Ser Cys Thr His Phe Pro Gly
1               5                   10                  15

Asn Leu Pro Asn Met Leu Arg Asp Leu Arg Asp Ala Phe Ser Arg Val
                20                  25                  30

Lys Thr Phe Phe Gln Met Lys Asp Gln Leu Asp Asn Leu Leu Leu Lys
            35                  40                  45

Glu Ser Leu Leu Glu Asp Phe Lys Gly Tyr Leu Gly Cys Gln Ala Leu
        50                  55                  60

Ser Glu Met Ile Gln Phe Tyr Leu Glu Glu Val Met Pro Gln Ala Glu
65                  70                  75                  80
```

```
Asn Gln Asp Pro Asp Ile Lys Ala His Val Asn Ser Leu Gly Glu Asn
                85                  90                  95

Leu Lys Thr Leu Arg Leu Arg Leu Arg Arg Cys His Arg Phe Leu Pro
            100                 105                 110

Cys Glu Asn Lys Ser Lys Ala Val Glu Gln Val Lys Asn Ala Phe Asn
        115                 120                 125

Lys Leu Gln Glu Lys Gly Ile Tyr Lys Ala Met Ser Glu Phe Asp Ile
    130                 135                 140

Phe Ile Asn Tyr Ile Glu Ala Tyr Met Thr Met Lys Ile Arg Asn
145                 150                 155

<210> SEQ ID NO 42
<211> LENGTH: 446
<212> TYPE: PRT
<213> ORGANISM: Artificial Sequence
<220> FEATURE:
<223> OTHER INFORMATION: Synthetic sequence

<400> SEQUENCE: 42

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile Leu Phe Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Phe Cys
                85                  90                  95

Ala Arg Ser Asn Tyr Gly Ser Phe Ala Ser Trp Gly Gln Gly Thr Leu
            100                 105                 110

Val Thr Val Ser Ala Ala Lys Thr Thr Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285
```

```
Arg Glu Glu Gln Phe Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys Ala Ser
            435                 440                 445

<210> SEQ ID NO 43
<211> LENGTH: 213
<212> TYPE: PRT
<213> ORGANISM: Artificial Sequence
<220> FEATURE:
<223> OTHER INFORMATION: Synthetic sequence

<400> SEQUENCE: 43

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser His Met
            20                  25                  30

His Trp Tyr Gln Gln Lys Ser Gly Thr Ser Pro Lys Arg Trp Ile Tyr
        35                  40                  45

Asp Thr Ser Arg Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser His Pro Trp Ser
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205
```

Asn Arg Gly Glu Cys
    210

<210> SEQ ID NO 44
<211> LENGTH: 446
<212> TYPE: PRT
<213> ORGANISM: Artificial Sequence
<220> FEATURE:
<223> OTHER INFORMATION: Synthetic sequence

<400> SEQUENCE: 44

Val Gln Leu Gln Gln Ser Gly Ala Glu Leu Val Arg Pro Gly Thr Ser
1               5                   10                  15

Val Lys Met Ser Cys Glu Ala Ala Arg Phe Thr Phe Ser Asn Tyr Trp
            20                  25                  30

Ile Gly Trp Val Lys Gln Arg Pro Gly His Gly Leu Glu Trp Ile Gly
        35                  40                  45

Asp Ile Phe Pro Gly Gly Asp Tyr Thr Asn Tyr Asn Lys Lys Phe Lys
    50                  55                  60

Asp Lys Ala Thr Leu Thr Ala Asp Thr Ser Ser Thr Ala Tyr Met
65                  70                  75                  80

Gln Leu Ser Ser Leu Thr Ser Glu Asp Ser Ala Ile Tyr Tyr Cys Ala
                85                  90                  95

Arg Ser Asp Tyr Gly Gly Tyr Tyr Val Phe Asp Tyr Trp Gly Gln Gly
            100                 105                 110

Thr Thr Leu Thr Val Ser Ser Ala Lys Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

```
Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
                435                 440                 445

<210> SEQ ID NO 45
<211> LENGTH: 220
<212> TYPE: PRT
<213> ORGANISM: Artificial Sequence
<220> FEATURE:
<223> OTHER INFORMATION: Synthetic sequence

<400> SEQUENCE: 45

Asp Ile Val Met Ser Gln Ser Pro Ser Ser Leu Ala Val Ser Val Gly
1               5                   10                  15

Glu Lys Val Thr Met Ser Cys Lys Ser Ser Gln Asn Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Tyr Thr Phe Gly Gly Gly Thr Lys Leu Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 46
<211> LENGTH: 445
<212> TYPE: PRT
<213> ORGANISM: Artificial Sequence
<220> FEATURE:
<223> OTHER INFORMATION: Synthetic sequence
```

```
<400> SEQUENCE: 46

Ala Gln Ile Gln Leu Val Gln Ser Gly Pro Glu Leu Lys Lys Pro Gly
1               5                   10                  15

Glu Thr Val Lys Ile Ser Cys Lys Ala Ser Gly Tyr Thr Phe Thr Asp
            20                  25                  30

Tyr Ser Val His Trp Val Lys Gln Ala Pro Gly Lys Gly Leu Lys Trp
        35                  40                  45

Met Gly Trp Ile Asn Thr Glu Thr Gly Glu Pro Thr Tyr Ala Asp Asp
    50                  55                  60

Leu Lys Gly Arg Phe Ala Phe Ser Leu Glu Thr Ser Ala Ser Thr Ala
65                  70                  75                  80

Tyr Leu Gln Ile Asn Asn Leu Lys Asn Glu Asp Thr Ala Thr Tyr Phe
                85                  90                  95

Cys Ala Lys Pro Thr Tyr Arg Phe Phe Asp Tyr Trp Gly Gln Gly Thr
            100                 105                 110

Thr Leu Thr Ala Ser Ser Ala Lys Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415
```

```
Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 47
<211> LENGTH: 219
<212> TYPE: PRT
<213> ORGANISM: Artificial Sequence
<220> FEATURE:
<223> OTHER INFORMATION: Synthetic sequence

<400> SEQUENCE: 47

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 48
<211> LENGTH: 449
<212> TYPE: PRT
<213> ORGANISM: Artificial Sequence
<220> FEATURE:
<223> OTHER INFORMATION: Synthetic sequence

<400> SEQUENCE: 48

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Val Pro Gly Lys Gly Leu Arg Trp Met
        35                  40                  45

Gly Trp Met Asp Thr Phe Thr Gly Glu Pro Thr Tyr Ala Asp Asp Phe
```

```
                50              55              60
Lys Gly Arg Phe Ala Phe Ser Leu Glu Thr Ser Ala Ser Thr Ala Tyr
 65              70              75              80
Leu Gln Ile Asn Ser Leu Lys Asn Glu Asp Thr Ala Thr Tyr Phe Cys
                85              90              95
Ala Arg Gly Gly Ile Leu Arg Leu Asn Tyr Phe Asp Tyr Trp Gly Gln
                100             105             110
Gly Thr Thr Leu Thr Val Ser Ser Ala Lys Thr Lys Gly Pro Ser Val
                115             120             125
Phe Pro Leu Ala Pro Cys Ser Arg Ser Thr Ser Glu Ser Thr Ala Ala
                130             135             140
Leu Gly Cys Leu Val Lys Asp Tyr Phe Pro Glu Pro Val Thr Val Ser
145             150             155             160
Trp Asn Ser Gly Ala Leu Thr Ser Gly Val His Thr Phe Pro Ala Val
                165             170             175
Leu Gln Ser Ser Gly Leu Tyr Ser Leu Ser Ser Val Val Thr Val Pro
                180             185             190
Ser Ser Ser Leu Gly Thr Lys Thr Tyr Thr Cys Asn Val Asp His Lys
                195             200             205
Pro Ser Asn Thr Lys Val Asp Lys Arg Val Glu Ser Lys Tyr Gly Pro
210             215             220
Pro Cys Pro Pro Cys Pro Ala Pro Glu Phe Glu Gly Gly Pro Ser Val
225             230             235             240
Phe Leu Phe Pro Pro Lys Pro Lys Asp Thr Leu Met Ile Ser Arg Thr
                245             250             255
Pro Glu Val Thr Cys Val Val Val Asp Val Ser Gln Glu Asp Pro Glu
                260             265             270
Val Gln Phe Asn Trp Tyr Val Asp Gly Val Glu Val His Asn Ala Lys
                275             280             285
Thr Lys Pro Arg Glu Glu Gln Phe Asn Ser Thr Tyr Arg Val Val Ser
290             295             300
Val Leu Thr Val Leu His Gln Asp Trp Leu Asn Gly Lys Glu Tyr Lys
305             310             315             320
Cys Lys Val Ser Asn Lys Gly Leu Pro Ser Ser Ile Glu Lys Thr Ile
                325             330             335
Ser Lys Ala Lys Gly Gln Pro Arg Glu Pro Gln Val Tyr Thr Leu Pro
                340             345             350
Pro Ser Gln Glu Glu Met Thr Lys Asn Gln Val Ser Leu Thr Cys Leu
                355             360             365
Val Lys Gly Phe Tyr Pro Ser Asp Ile Ala Val Glu Trp Glu Ser Asn
370             375             380
Gly Gln Pro Glu Asn Asn Tyr Lys Thr Thr Pro Pro Val Leu Asp Ser
385             390             395             400
Asp Gly Ser Phe Phe Leu Tyr Ser Arg Leu Thr Val Asp Lys Ser Arg
                405             410             415
Trp Gln Glu Gly Asn Val Phe Ser Cys Ser Val Met His Glu Ala Leu
                420             425             430
His Asn His Tyr Thr Gln Lys Ser Leu Ser Leu Ser Leu Gly Lys Ala
                435             440             445
Ser

<210> SEQ ID NO 49
<211> LENGTH: 214
```

```
<212> TYPE: PRT
<213> ORGANISM: Artificial Sequence
<220> FEATURE:
<223> OTHER INFORMATION: Synthetic sequence

<400> SEQUENCE: 49

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Gly Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
50                  55                  60

Ser Gly Ser Gly Lys Asp Tyr Ala Leu Ser Ile Thr Ser Leu Gln Thr
65                  70                  75                  80

Glu Asp Leu Ala Thr Tyr Tyr Cys Gln Gln Cys Trp Thr Ser Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 50
<211> LENGTH: 445
<212> TYPE: PRT
<213> ORGANISM: Artificial Sequence
<220> FEATURE:
<223> OTHER INFORMATION: Synthetic sequence

<400> SEQUENCE: 50

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Ile Asn Pro Asn Tyr Gly Asp Thr Phe Tyr Asn Gln Lys Phe
50                  55                  60

Glu Gly Lys Ala Thr Leu Thr Val Asp Lys Ser Ser Arg Thr Ala Tyr
65                  70                  75                  80

Met Gln Leu Asn Ser Leu Thr Ser Glu Asp Ser Ala Val Tyr Tyr Cys
                85                  90                  95

Gly Arg Gly Asp Tyr Gly Tyr Phe Asp Val Trp Gly Ala Gly Thr Thr
            100                 105                 110
```

Val Thr Val Ser Ser Ala Lys Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
        210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Gly Lys Ala Ser
            435                 440                 445

<210> SEQ ID NO 51
<211> LENGTH: 214
<212> TYPE: PRT
<213> ORGANISM: Artificial Sequence
<220> FEATURE:
<223> OTHER INFORMATION: Synthetic sequence

<400> SEQUENCE: 51

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
 50                  55                  60

Ser Gly Ser Gly Thr Asp Phe Thr Leu Thr Ile Asn Asn Val Gln Ser
 65                  70                  75                  80

Glu Asp Leu Ala Asp Tyr Phe Cys Gln Gln Tyr Ser Ser Asn Pro Tyr
                 85                  90                  95

Met Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 52
<211> LENGTH: 447
<212> TYPE: PRT
<213> ORGANISM: Artificial Sequence
<220> FEATURE:
<223> OTHER INFORMATION: Synthetic sequence

<400> SEQUENCE: 52

Gln Leu Gln Gln Ser Gly Pro Glu Leu Val Lys Pro Gly Ala Ser Val
 1               5                  10                  15

Lys Ile Ser Cys Lys Thr Ser Gly Tyr Thr Phe Thr Glu Tyr Thr Met
                20                  25                  30

His Trp Val Arg Gln Ser His Gly Lys Ser Leu Glu Trp Ile Gly Gly
            35                  40                  45

Ile Asn Pro Ile Asn Gly Gly Pro Thr Tyr Asn Gln Lys Phe Lys Gly
 50                  55                  60

Lys Ala Thr Leu Thr Val Asp Lys Ser Ser Ser Thr Ala Tyr Met Glu
65                   70                  75                  80

Leu Arg Ser Leu Thr Ser Glu Asp Ser Ala Val Tyr Tyr Cys Ala Arg
                 85                  90                  95

Trp Asp Tyr Gly Ser Arg Asp Val Met Asp Tyr Trp Gly Gln Gly Thr
            100                 105                 110

Ser Val Thr Val Ser Ser Ala Lys Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

```
Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys Ala Ser
            435                 440                 445

<210> SEQ ID NO 53
<211> LENGTH: 214
<212> TYPE: PRT
<213> ORGANISM: Artificial Sequence
<220> FEATURE:
<223> OTHER INFORMATION: Synthetic sequence

<400> SEQUENCE: 53

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Arg Pro Glu Gln Ser Pro Lys Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Thr Tyr Ser Tyr Ile Phe
            85                  90                  95
```

```
Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```